(12) United States Patent
Plucienniczak et al.

(10) Patent No.: US 8,158,382 B2
(45) Date of Patent: *Apr. 17, 2012

(54) UBP1 PROTEASE MUTANT AND ITS CODING SEQUENCE, THEIR APPLICATIONS AND HETEROGONOUS PROTEIN EXPRESSION SYSTEM

(75) Inventors: Andrzej Plucienniczak, Warszawa (PL); Anna Wojtowicz, Warszawa (PL); Anna Mazurkiewicz, Radom (PL); Luiza Chojnacka, Pultusk (PL)

(73) Assignee: Instytut Biotechnologii I Antybiotykow, Warszawa (PL)

( * ) Notice: Subject to any disclaimer, the term of this patent is extended or adjusted under 35 U.S.C. 154(b) by 1021 days.

This patent is subject to a terminal disclaimer.

(21) Appl. No.: 11/795,055

(22) PCT Filed: Jan. 10, 2005

(86) PCT No.: PCT/PL2005/000002
§ 371 (c)(1),
(2), (4) Date: Jul. 9, 2007

(87) PCT Pub. No.: WO2006/073320
PCT Pub. Date: Jul. 13, 2006

(65) Prior Publication Data
US 2008/0153130 A1 Jun. 26, 2008

(51) Int. Cl.
*C12P 21/06* (2006.01)
*C12N 9/48* (2006.01)
*C12N 1/20* (2006.01)
*C07H 21/04* (2006.01)

(52) U.S. Cl. .......... 435/69.1; 435/212; 435/252.33; 435/320.1; 536/23.2; 536/23.1

(58) Field of Classification Search .......... None
See application file for complete search history.

(56) References Cited

FOREIGN PATENT DOCUMENTS
| WO | WO 91/17245 | 11/2001 |
| WO | WO 2004/097011 | 11/2004 |
| WO | WO 2005/066208 | 7/2005 |

OTHER PUBLICATIONS

Schmitz, C. et al. (2005) "The Deubiquitinating Enzyme Ubp1 Affects Sorting of the ATP-binding Cassette-Transporter Ste6 in the Endocytic Pathway," Molecular Biology of the Cell, vol. 16, pp. 1319-1329.
Examination Report issued Mar. 26, 2008 in connection with European Patent Application No. 05704662.5.
Oct. 25, 2008 Reply to the Examination Report issued Mar. 26, 2008 in connection with European Patent Application No. 05704662.5.
Examination Report issued Apr. 27, 2009 in connection with European Patent Application No. 05704662.5.
Nov. 11, 2009 Reply to the Examination Report issued Apr. 27, 2009 in connection with European Patent Application No. 05704662.5.
Examination Report issued Mar. 2, 2010 in connection with European Patent Application No. 05704662.5.
Database UniProt [Online] May 1, 1999, "RecName: Full=Ubiquitin carboxyl-terminal hydrolase 1; EC=3.1.2.15; AltName: Full=Ubiquitin thioesterase 1; AltName: Full=Ubiquitin-specific-processing protease 1; AltName: Full=Deubiquitinating enzyme 1; Short=hUB" retrieved from EBI accession No. UNIPROT:O94782 Database accession No. O94782.
Potter, J.L. et al (1999) "Precursor processing of Pro-ISG15/UCRP, an interferon-beta-induced ubiquitin-like protein" *Journal of Biological Chemistry* 274:25061-25068.

*Primary Examiner* — Nashaat Nashed
(74) *Attorney, Agent, or Firm* — Gary J. Gershik; Cooper & Dunham LLP

(57) ABSTRACT

Invention relates to novel and improved UBP1 protease mutants with a substitution at position (754), a deletion of amino-acids at position (1-54) and at least a portion of the amino-acids found at position (55-98) and their coding sequence as well as their applications and heterogonous protein expression system comprising thereof.

24 Claims, 10 Drawing Sheets

```
     +1  MetGlnIlePhe ValLysThr LeuThrGly LysThrIleThr LeuGluVal GluSerSer
      1  ATGCAGATTT TCGTCAAAAC TTTGACCGGT AAAACCATAA CATTGGAAGT GAATCTTCC
         TACGTCTAAA AGCAGTTTTG AAACTGGCCA TTTTGGTATT GTAACCTTCA CTTAGAAGG

+1  AspThrIleAsp AsnValLys SerLysIle GlnAspLysGlu GlyIlePro ProAspGln
     61  GATACCATCG ACAACGTTAA GTCGAAAATT CAAGACAAGG AAGGTATCCC TCCAGATCAA
         CTATGGTAGC TGTTGCAATT CAGCTTTTAA GTTCTGTTCC TTCCATAGGG AGGTCTAGTT

+1  GlnArgLeuIle PheAlaGly LysGlnLeu GluAspGlyArg ThrLeuSer AspTyrAsn
    121  CAAAGATTGA TCTTTGCCGG TAAGCAGCTA GAAGACGGTA GAACGCTGTC TGATTACAAC
         GTTTCTAACT AGAAACGGCC ATTCGTCGAT CTTCTGCCAT CTTGCGACAG ACTAATGTTG

+1  IleGlnLysGlu SerThrLeu HisLeuVal LeuArgLeuArg GlyGlyAsp HisLeuAsn
                                                      AflII       SacII
    181  ATTCAGAAGG AGTCCACCTT ACATCTTGTC TTAAGACTCC GCGGTGGTGA CCATCTAAAC
         TAAGTCTTCC TCAGGTGGAA TGTAGAACAG AATTCTGAGG CGCCACCACT GGTAGATTTG

+1  TyrIleValGlu SerValSer GluMetThr ThrAsnPheArg AsnAsnAsn SerLeuSer
    241  TACATTGTTG AGAGCGTTAG TGAAATGACA ACAAACTTCA GAAATAATAA TAGCCTTAGC
         ATGTAACAAC TCTCGCAATC ACTTTACTGT TGTTTGAAGT CTTTATTATT ATCGGAATCG

+1  ArgTrpLeuPro ArgSerLys PheThrHis LeuAspGluGlu IleLeuLys ArgGlyGly
                                                                  BglII
    301  CGTTGGTTGC CCAGAAGTAA GTTTACCCAC TTAGACGAAG AGATCTTGAA ACGTGGTGGT
         GCAACCAACG GGTCTTCATT CAAATGGGTG AATCTGCTTC TCTAGAACTT TGCACCACCA

+1  PheIleAlaGly LeuValAsn AspGlyAsn ThrCysPheMet AsnSerVal LeuGlnSer
    361  TTCATTGCTG GTTTAGTTAA TGATGGTAAC ACTTGTTTTA TGAACTCTGT TTTGCAATCA
         AAGTAACGAC CAAATCAATT ACTACCATTG TGAACAAAAT ACTTGAGACA AAACGTTAGT

+1  LeuAlaSerSer ArgGluLeu MetGluPhe LeuAspAsnAsn ValIleArg ThrTyrGlu
    421  TTGGCATCAT CCAGAGAATT AATGGAGTTC TTGGACAATA ATGTCATAAG GACCTATGAG
         AACCGTAGTA GGTCTCTTAA TTACCTCAAG AACCTGTTAT TACAGTATTC CTGGATACTC

+1  GluIleGluGln AsnGluHis AsnGluGlu GlyAsnGlyGln GluSerAla GlnAspGlu
    481  GAGATAGAAC AAAATGAACA CAATGAAGAA GGAAACGGGC AAGAATCTGC TCAAGATGAA
         CTCTATCTTG TTTTACTTGT GTTACTTCTT CCTTTGCCCG TTCTTAGACG AGTTCTACTT

+1  AlaThrHisLys LysAsnThr ArgLysGly GlyLysValTyr GlyLysHis LysLysLys
    541  GCCACTCATA AGAAAAACAC TCGTAAGGGT GGCAAAGTTT ATGGTAAGCA TAAGAAGAAA
         CGGTGAGTAT TCTTTTTGTG AGCATTCCCA CCGTTTCAAA TACCATTCGT ATTCTTCTTT

+1  LeuAsnArgLys SerSerSer LysGluAsp GluGluLysSer GlnGluPro AspIleThr
    601  TTGAATAGGA AGTCAAGTTC GAAAGAAGAC GAAGAAAAGA GCCAGGAGCC AGATATCACT
         AACTTATCCT TCAGTTCAAG CTTTCTTCTG CTTCTTTTCT CGGTCCTCGG TCTATAGTGA

+1  PheSerValAla LeuArgAsp LeuLeuSer AlaLeuAsnAla LysTyrTyr ArgAspLys
                     AflII
    661  TTCAGTGTCG CCTTAAGGGA TCTACTTTCT GCCTTAAATG CGAAGTATTA TCGGGATAAA
         AAGTCACAGC GGAATTCCCT AGATGAAAGA CGGAATTTAC GCTTCATAAT AGCCCTATTT

+1  ProTyrPheLys ThrAsnSer LeuLeuLys AlaMetSerLys SerProArg LysAsnIle
    721  CCCTATTTCA AAACCAATAG TTATTGAAA GCAATGTCCA AATCTCCAAG AAAAAATATT
         GGGATAAAGT TTTGGTTATC AATAACTTT CGTTACAGGT TTAGAGGTTC TTTTTTATAA
```

```
     +1 LeuLeuGlyTyr AspGlnGlu AspAlaGln GluPhePheGln AsnIleLeu AlaGluLeu
                                            EcoRI
    781 CTTCTTGGCT ACGACCAAGA GGACGCGCAA GAATTCTTCC AGAACATACT AGCCGAGTTG
        GAAGAACCGA TGCTGGTTCT CCTGCGCGTT CTTAAGAAGG TCTTGTATGA TCGGCTCAAC

+1 GluSerAsnVal LysSerLeu AsnThrGlu LysLeuAspThr ThrProVal AlaLysSer
    841 GAAAGTAACG TTAAATCATT GAATACTGAA AAACTAGATA CCACTCCAGT TGCGAAATCA
        CTTTCATTGC AATTTAGTAA CTTATGACTT TTTGATCTAT GGTGAGGTCA ACGCTTTAGT

+1 GluLeuProAsp AspAlaLeu ValGlyGln LeuAsnLeuGly GluValGly ThrValTyr
    901 GAATTACCCG ATGATGCTTT AGTAGGTCAA CTTAACCTTG GTGAAGTTGG CACTGTTTAC
        CTTAATGGGC TACTACGAAA TCATCCAGTT GAATTGGAAC CACTTCAACC GTGACAAATG

+1 IleProThrGlu GlnIleAsp ProAsnSer IleLeuHisAsp LysSerIle GlnAsnPhe
    961 ATTCCAACTG AACAGATTGA TCCTAACTCT ATACTACATG ACAAGTCCAT TCAAAATTTC
        TAAGGTTGAC TTGTCTAACT AGGATTGAGA TATGATGTAC TGTTCAGGTA AGTTTTAAAG

+1 ThrProPheLys LeuMetThr ProLeuAsp GlyIleThrAla GluArgIle GlyCysLeu
   1021 ACACCTTTCA AACTAATGAC TCCTTTAGAT GGTATCACGG CAGAACGTAT TGGTTGTTTA
        TGTGGAAAGT TTGATTACTG AGGAAATCTA CCATAGTGCC GTCTTGCATA ACCAACAAAT

+1 GlnCysGlyGlu AsnGlyGly IleArgTyr SerValPheSer GlyLeuSer LeuAsnLeu
   1081 CAGTGTGGTG AGAACGGTGG CATAAGATAT TCCGTATTTT CGGGACTGAG CCTGAATCTG
        GTCACACCAC TCTTGCCACC GTATTCTATA AGGCATAAAA GCCCTGACTC GGACTTAGAC

+1 ProAsnGluAsn IleGlySer ThrLeuLys LeuSerGlnLeu LeuSerAsp TrpSerLys
   1141 CCGAACGAGA ATATTGGTTC CACTCTGAAA CTGTCTCAGC TGCTGAGCGA CTGGAGTAAA
        GGCTTGCTCT TATAACCAAG GTGAGACTTT GACAGAGTCG ACGACTCGCT GACCTCATTT

+1 ProGluIleIle GluGlyVal GluCysAsn ArgCysAlaLeu ThrAlaAla HisSerHis
   1201 CCTGAAATCA TCGAAGGCGT AGAATGTAAC CGTTGTGCCC TCACAGCAGC GCACTCTCAT
        GGACTTTAGT AGCTTCCGCA TCTTACATTG GCAACACGGG AGTGTCGTCG CGTGAGAGTA

+1 LeuPheGlyGln LeuLysGlu PheGluLys LysProGluGly SerIlePro GluLysPro
   1261 TTATTTGGTC AGTTGAAAGA ATTTGAAAAA AAACCTGAGG GTTCGATCCC AGAAAAGCCA
        AATAAACCAG TCAACTTTCT TAAACTTTTT TTTGGACTCC CAAGCTAGGG TCTTTTCGGT

+1 IleAsnAlaVal LysAspArg ValHisGln IleGluGluVal LeuAlaLys ProValIle
   1321 ATTAACGCTG TAAAAGATCG CGTCCATCAA ATCGAAGAAG TTCTTGCCAA ACCAGTTATT
        TAATTGCGAC ATTTTCTAGC GCAGGTAGTT TAGCTTCTTC AAGAACGGTT TGGTCAATAA

+1 AspAspGluAsp TyrLysLys LeuHisThr AlaAsnMetVal ArgLysCys SerLysSer
   1381 GACGATGAAG ATTATAAGAA GTTGCATACA GCAAATATGG TACGTAAATG CTCTAAATCT
        CTGCTACTTC TAATATTCTT CAACGTATGT CGTTTATACC ATGCATTTAC GAGATTTAGA

+1 LysGlnIleLeu IleSerArg ProProPro LeuLeuSerIle HisIleAsn ArgSerVal
   1441 AAGCAGATTT TAATATCAAG ACCTCCACCA CTGCTGTCCA TTCATATCAA CCGTTCCGTA
        TTCGTCTAAA ATTATAGTTC TGGAGGTGGT GACGACAGGT AAGTATAGTT GGCAAGGCAT

+1 PheAspProArg ThrTyrMet IleArgLys AsnAsnSerLys ValLeuPhe LysSerArg
   1501 TTTGATCCAC GCACGTACAT GATTCGTAAA AATAACTCGA AGTATTGTT TAAGTCAAGG
        AAACTAGGTG CGTGCATGTA CTAAGCATTT TTATTGAGCT TCATAACAA ATTCAGTTCC

+1 LeuAsnLeuAla ProTrpCys CysAspIle AsnGluIleAsn LeuAspAla ArgLeuPro
   1561 TTGAATCTTG CCCCATGGTG TTGTGATATT AATGAAATCA ATTTGGATGC TCGTTTGCCA
        AACTTAGAAC GGGGTACCAC AACACTATAA TTACTTTAGT TAAACCTACG AGCAAACGGT

+1 MetSerLysLys GluLysAla AlaGlnGln AspSerSerGlu AspGluAsn IleGlyGly
```

```
1621 ATGTCAAAAA AGGAAAAAGC TGCGCAACAA GATTCAAGTG AAGATGAAAA CATTGGCGGT
     TACAGTTTTT TCCTTTTTCG ACGCGTTGTT CTAAGTTCAC TTCTACTTTT GTAACCGCCA

+1 GluTyrTyrThr LysLeuHis GluArgPhe GluGlnGluPhe GluAspSer GluGluGlu
1681 GAATACTATA CGAAATTACA TGAACGCTTC GAGCAGGAAT TTGAAGACAG CGAGGAAGAA
     CTTATGATAT GCTTTAATGT ACTTGCGAAG CTCGTCCTTA AACTTCTGTC GCTCCTTCTT

+1 LysGluTyrAsp AspAlaGlu GlyAsnTyr AlaSerHisTyr AsnHisThr LysAspIle
1741 AAAGAATACG ATGACGCAGA GGGGAACTAT GCGTCTCATT ACAATCATAC CAAGGATATC
     TTTCTTATGC TACTGCGTCT CCCCTTGATA CGCAGAGTAA TGTTAGTATG GTTCCTATAG

+1 SerAsnTyrAsp ProLeuAsn GlyGluVal AspGlyValThr SerAspAsp GluAspGlu
1801 AGTAACTATG ATCCCCTAAA CGGTGAAGTC GATGGCGTGA CATCCGATGA TGAAGATGAG
     TCATTGATAC TAGGGGATTT GCCACTTCAG CTACCGCACT GTAGGCTACT ACTTCTACTC

+1 TyrIleGluGlu ThrAspAla LeuGlyAsn ThrIleLysLys ArgIleIle GluHisSer
1861 TACATTGAAG AAACCGATGC TTTAGGGAAT ACAATCAAAA AACGTATCAT AGAACATTCT
     ATGTAACTTC TTTGGCTACG AAATCCCTTA TGTTAGTTTT TTGCATAGTA TCTTGTAAGA

+1 AspValGluAsn GluAsnVal LysAspAsn GluGluLeuGln GluIleAsp AsnValSer
1921 GATGTTGAAA ACGAGAATGT AAAAGATAAT GAAGAACTGC AAGAAATCGA CAATGTGAGC
     CTACAACTTT TGCTCTTACA TTTTCTATTA CTTCTTGACG TTCTTTAGCT GTTACACTCG

+1 LeuAspGluPro LysIleAsn ValGluAsp GlnLeuGluThr SerSerAsp GluGluAsp
1981 CTTGACGAAC CAAAGATCAA TGTTGAAGAT CAACTAGAAA CATCATCTGA TGAGGAAGAT
     GAACTGCTTG GTTTCTAGTT ACAACTTCTA GTTGATCTTT GTAGTAGACT ACTCCTTCTA

+1 ValIleProAla ProProIle AsnTyrAla ArgSerPheSer ThrValPro AlaThrPro
2041 GTTATACCAG CTCCACCTAT CAATTATGCT AGGTCATTTT CCACAGTTCC AGCCACTCCA
     CAATATGGTC GAGGTGGATA GTTAATACGA TCCAGTAAAA GGTGTCAAGG TCGGTGAGGT

+1 LeuThrTyrSer LeuArgSer ValIleVal HisTyrGlyThr HisAsnTyr GlyHisTyr
2101 TTGACATATT CATTGCGCTC TGTCATTGTT CACTACGGTA CCCATAATTA TGGTCATTAC
     AACTGTATAA GTAACGCGAG ACAGTAACAA GTGATGCCAT GGGTATTAAT ACCAGTAATG

+1 IleAlaPheArg LysTyrArg GlyCysTrp TrpArgIleSer AspGluThr ValTyrVal
2161 ATTGCATTTC GTAAATACCG TGGTTGTTGG TGGCGTATAT CTGATGAGAC TGTGTACGTT
     TAACGTAAAG CATTTATGGC ACCAACAACC ACCGCATATA GACTACTCTG ACACATGCAA

+1 ValAspGluAla GluValLeu SerThrPro GlyValPheMet LeuPheTyr GluTyrAsp
2221 GTGGACGAAG CTGAAGTCCT TCAACACCC GGTGTATTTA TGTTATTTTA CGAATATGAC
     CACCTGCTTC GACTTCAGGA AGTTGTGGG CCACATAAAT ACAATAAAAT GCTTATACTG

+1 PheAspGluGlu ThrGlyLys MetLysAsp AspLeuGluAla IleLeuSer AsnAsnGlu
2281 TTTGATGAAG AAACTGGGAA GATGAAGGAT GATTTGGAAG CTATTCTGAG TAATAATGAA
     AAACTACTTC TTTGACCCTT CTACTTCCTA CTAAACCTTC GATAAGACTC ATTATTACTT

+1 GluAspAspGlu LysGluGln GluGlnLys GlyValGlnGlu ProLysGlu SerGlnGlu
2341 GAAGATGATG AAAAAGAGCA GGAGCAAAAA GGAGTCCAGG AGCCAAAGGA AAGCCAAGAG
     CTTCTACTAC TTTTTCTCGT CCTCGTTTTT CCTCAGGTCC TCGGTTTCCT TTCGGTTCTC

+1 GlnGlyGluGly GluGluGln GluGluGly GlnGluGlnMet LysPheGlu ArgThrGlu
2401 CAAGGAGAAG GTGAAGAGCA AGAGGAAGGT CAAGAGCAGA TGAAGTTCGA GCGTACAGAA
     GTTCCTCTTC CACTTCTCGT TCTCCTTCCA GTTCTCGTCT ACTTCAAGCT CGCATGTCTT

+1 AspHisArgAsp IleSerGly LysAspVal AsnGlySerHis HisHisHis HisHis***
2461 GACCATCGCG ATATTTCTGG TAAAGATGTA AACGGATCCC ATCATCACCA TCACCATTAA
     CTGGTAGCGC TATAAAGACC ATTTCTACAT TTGCCTAGGG TAGTAGTGGT AGTGGTAATT
```

Fig. 2a

```
   1 ggtggtttca ttgctggttt agttaatgat ggtaacactt gttttatgaa ctctgttttg
  61 caatcattgg catcatccag agaattaatg gagttcttgg acaataatgt cataaggacc
 121 tatgaggaga tagaacaaaa tgaacacaat gaagaaggaa acgggcaaga atctgctcaa
 181 gatgaagcca ctcataagaa aaacactcgt aagggtggca aagtttatgg taagcataag
 241 aagaaattga ataggaagtc aagttcgaaa gaagacgaag aaaagagcca ggagccagat
 301 atcactttca gtgtcgcctt aagggatcta ctttctgcct taaatgcgaa gtattatcgg
 361 gataaaccct atttcaaaac caatagttta ttgaaagcaa tgtccaaatc tccaagaaaa
 421 aatattcttc ttggctacga ccaagaggac gcgcaagaat tcttccagaa catactagcc
 481 gagttggaaa gtaacgttaa atcattgaat actgaaaaac tagataccac tccagttgcg
 541 aaatcagaat tacccgatga tgctttagta ggtcaactta accttggtga agttggcact
 601 gtttacattc caactgaaca gattgatcct aactctatac tacatgacaa gtccattcaa
 661 aatttcacac ctttcaaact aatgactcct ttagatggta tcacggcaga acgtattggt
 721 tgtttacagt gtggtgagaa cggtggcata agatattccg tattttcggg actgagcctg
 781 aatctgccga acgagaatat tggttccact ctgaaactgt ctcagctgct gagcgactgg
 841 agtaaacctg aaatcatcga aggcgtagaa tgtaaccgtt gtgccctcac agcagcgcac
 901 tctcatttat ttggtcagtt gaaagaattt gaaaaaaaac ctgagggttc gatcccagaa
 961 aagccaatta acgctgtaaa agatcgcgtc catcaaatcg aagaagttct tgccaaacca
1021 gttattgacg atgaagatta taagaagttg catacagcaa atatggtacg taaatgctct
1081 aaatctaagc agattttaat atcaagacct ccaccactgc tgtccattca tatcaaccgt
1141 tccgtatttg atccacgcac gtacatgatt cgtaaaaata actcgaaagt attgtttaag
1201 tcaaggttga atcttccccc atggtgttgt gatattaatg aaatcaattt ggatgctcgt
1261 ttgccaatgt caaaaaagga aaaagctgcg caacaagatt caagtgaaga tgaaaacatt
1321 ggcggtgaat actatacgaa attacatgaa cgcttcgagc aggaatttga agacagcgag
1381 gaagaaaaag aatacgatga cgcagagggg aactatgcgt ctcattacaa tcataccaag
1441 gatatcagta actatgatcc cctaaacggt gaagtcgatg gcgtgacatc cgatgatgaa
1501 gatgagtaca ttgaagaaac cgatgcttta gggaatacaa tcaaaaaacg tatcatagaa
1561 cattctgatg ttgaaaacga gaatgtaaaa gataatgaag aactgcaaga aatcgacaat
1621 gtgagccttg acgaaccaaa gatcaatgtt gaagatcaac tagaaacatc atctgatgag
1681 gaagatgtta taccagctcc acctatcaat tatgctaggt catttttccac agttccagcc
1741 actccattga catattcatt gcgctctgtc attgttcact acggtaccca taattatggt
1801 cattacattg catttcgtaa ataccgtggt tgttggtggc gtatatctga tgagactgtg
1861 tacgttgtgg acgaagctga agtcctttca cacccggtg tatttatgtt attttacgaa
1921 tatgactttg atgaagaaac tgggaagatg aaggatgatt tggaagctat tctgagtaat
1981 aatgaagaag atgatgaaaa agagcaggag caaaaggag tccaggagcc aaaggaaagc
2041 caagagcaag gagaaggtga agagcaagag gaaggtcaag agcagatgaa gttcgagcgt
2101 acagaagacc atcgcgatat ttctggtaaa gatgtaaacg gatcccatca tcaccatcac
2161 cattaa
```

Fig. 2b

```
1    mdlfieskin sllqflfgsr qdflrnfktw snnnnnlsiy llifgivvff ykkpdhlnyi
61   vesvsemttn frnnnslsrw lprskfthld eeilkrggfi ag*lvndgntc fmnsvlqsl*a
121  ssrelmefld nnvirtyeei eqnehneegn gqesaqdeat hkkntrkggk vygkhkkkln
181  rkssskedee ksqepditfs valrdllsal nakyyrdkpy fktnsllkam sksprknill
241  gydqedaqef fqnilaeles nvkslntekl dttpvaksel pddalvgqln lgevgtvyip
301  teqidpnsil hdksiqnftp fklmtpldgi taerigclqc genggirysv fsglslnlpn
361  enigstlkls qllsdwskpe iiegvecnrc altaahshlf gqlkefekkp egsipekpin
421  avkdrvhqie evlakpvidd edykklhtan mvrkcskskq ilisrpppll sihinrsvfd
481  prtymirknn skvlfksrln lapwccdine inldarlpms kkekaaqqds sedeniggey
541  ytklherfeq efedseeeke yddaegnyas hynhtkdisn ydplngevdg vtsddedeyi
601  eetdalgnti kkriiehsdv enenvkdnee lqeidnvsld epkinvedql etssdeedvi
661  pappinyars fstvpatplt *yslrsvivhy gthnyghyia frkyrgcwwr isdetvyvvd*
721  *eaevlstpgv fmlfy*eydfd eetgkmkddl eai*l*snneed dekeqeqkgv qepkesqeqg
781  egeeqeegqe qmkfertedh rdisgkdvng *shhhhhh*
```

Fig. 6

```
 +1  MetAlaHisHis HisHisHis HisSerGly SerGluPheGln IlePheVal LysThrLeu
                                          EcoRI
  1  ATGGCACATC ATCACCATCA CCACTCTGGT TCTGAATTCC AAATTTTTGT TAAAACTTTA
     TACCGTGTAG TAGTGGTAGT GGTGAGACCA AGACTTAAGG TTTAAAAACA ATTTTGAAAT

+1  ThrGlyLysThr IleThrLeu GluValGlu SerSerAspThr IleAspAsn ValLysSer
 61  ACTGGTAAAA CCATTACCTT AGAAGTTGAA TCTTCAGATA CCATTGATAA TGTTAAATCT
     TGACCATTTT GGTAATGGAA TCTTCAACTT AGAAGTCTAT GGTAACTATT ACAATTTAGA

+1  LysIleGlnAsp LysGluGly IleProPro AspGlnGlnArg LeuIlePhe AlaGlyLys
121  AAAATTCAAG ATAAAGAAGG TATTCCTCCA GATCAACAAC GTCTAATATT TGCAGGTAAA
     TTTTAAGTTC TATTTCTTCC ATAAGGAGGT CTAGTTGTTG CAGATTATAA ACGTCCATTT

+1  GlnLeuGluAsp GlyArgThr LeuSerAsp TyrAsnIleGln LysGluSer ThrLeuHis
181  CAGTTAGAAG ATGGTCGTAC CCTGTCTGAT TATAACATTC AGAAAGAATC TACCTTACAT
     GTCAATCTTC TACCAGCATG GGACAGACTA ATATTGTAAG TCTTTCTTAG ATGGAATGTA

+1  LeuValLeuArg LeuArg
                         SacII
241  CTGGTCTTAC GTCTCCGCGG
     GACCAGAATG CAGAGGCGCC
```

Fig. 8

```
 +1 MetAlaHisHis HisHisHis HisSerGly SerGluPheGln IlePheVal LysThrLeu
                                         EcoRI
  1 ATGGCACATC ATCACCATCA CCACTCTGGT TCTGAATTCC AAATTTTTGT TAAAACTTTA
    TACCGTGTAG TAGTGGTAGT GGTGAGACCA AGACTTAAGG TTTAAAAACA ATTTTGAAAT

+1 ThrGlyLysThr IleThrLeu GluValGlu SerSerAspThr IleAspAsn ValLysSer
 61 ACTGGTAAAA CCATTACCTT AGAAGTTGAA TCTTCAGATA CCATTGATAA TGTTAAATCT
    TGACCATTTT GGTAATGGAA TCTTCAACTT AGAAGTCTAT GGTAACTATT ACAATTTAGA

+1 LysIleGlnAsp LysGluGly IleProPro AspGlnGlnArg LeuIlePhe AlaGlyLys
121 AAAATTCAAG ATAAAGAAGG TATTCCTCCA GATCAACAAC GTCTAATATT TGCAGGTAAA
    TTTTAAGTTC TATTTCTTCC ATAAGGAGGT CTAGTTGTTG CAGATTATAA ACGTCCATTT

+1 GlnLeuGluAsp GlyArgThr LeuSerAsp TyrAsnIleGln LysGluSer ThrLeuHis
181 CAGTTAGAAG ATGGTCGTAC CCTGTCTGAT TATAACATTC AGAAAGAATC TACCTTACAT
    GTCAATCTTC TACCAGCATG GGACAGACTA ATATTGTAAG TCTTTCTTAG ATGGAATGTA

+1 LeuValLeuArg LeuArgGly GlyThrHis AsnTyrGlyHis TyrIleAla PheArgLys
                 SacII     Asp718
241 CTGGTCTTAC GTCTCCGCGG TGGTACCCAT AATTATGGTC ATTACATTGC ATTTCGTAAA
    GACCAGAATG CAGAGGCGCC ACCATGGGTA TTAATACCAG TAATGTAACG TAAAGCATTT

+1 TyrArgGlyCys TrpTrpArg IleSerAsp GluThrValTyr ValValAsp GluAlaGlu
301 TACCGTGGTT GTTGGTGGCG TATATCTGAT GAGACTGTGT ACGTTGTGGA CGAAGCTGAA
    ATGGCACCAA CAACCACCGC ATATAGACTA CTCTGACACA TGCAACACCT GCTTCGACTT

+1 ValLeuSerThr ProGlyVal PheMetLeu PheTyrGluTyr AspPheAsp GluGluThr
361 GTCCTTTCAA CACCCGGTGT ATTTATGTTA TTTTACGAAT ATGACTTTGA TGAAGAAACT
    CAGGAAAGTT GTGGGCCACA TAAATACAAT AAAAATGCTTA TACTGAAACT ACTTCTTTGA

+1 GlyLysMetLys AspAspLeu GluAlaIle LeuSerAsnAsn GluGluAsp AspGluLys
421 GGGAAGATGA AGGATGATTT GGAAGCTATT CTGAGTAATA ATGAAGAAGA TGATGAAAAA
    CCCTTCTACT TCCTACTAAA CCTTCGATAA GACTCATTAT TACTTCTTCT ACTACTTTTT

+1 GluGlnGluGln LysGlyVal GlnGluPro LysGluSerGln GluGlnGly GluGlyGlu
481 GAGCAGGAGC AAAAAGGAGT CCAGGAGCCA AAGGAAAGCC AAGAGCAAGG AGAAGGTGAA
    CTCGTCCTCG TTTTTCCTCA GGTCCTCGGT TTCCTTTCGG TTCTCGTTCC TCTTCCACTT

+1 GluGlnGluGlu GlyGlnGlu GlnMetLys PheGluArgThr GluAspHis ArgAspIle
541 GAGCAAGAGG AAGGTCAAGA GCAGATGAAG TTCGAGCGTA CAGAAGACCA TCGCGATATT
    CTCGTTCTCC TTCCAGTTCT CGTCTACTTC AAGCTCGCAT GTCTTCTGGT AGCGCTATAA

+1 SerGlyLysAsp ValAsn***
601 TCTGGTAAAG ATGTAAACTA A
    AGACCATTTC TACATTTGAT T
``` under the invention entitled "UBP1 Protease Mutant and its coding sequence, their applications and heterogonous protein expression system"

SEQUENCE LISTING

<160> NUMBER OF SEQ ID NOS: 26

<210> SEQ ID NO 1
<211> LENGTH: 260
<212> TYPE: DNA
<213> ORGANISM: artificial sequence
<220> FEATURE:
<223> OTHER INFORMATION: 6Hisubi, based on yeast source

<400> SEQUENCE: 1
atggcacatc atcaccatca ccactctggt tctgaattcc aaattttgt taaaacttta    60 actggtaaaa ccattacctt agaagttgaa tcttcagata ccattgataa tgttaaatct   120
aaaattcaag ataaagaagg tattcctcca gatcaacaac gtctaatatt tgcaggtaaa   180
cagttagaag atggtcgtac cctgtctgat tataacattc agaaagaatc taccttacat   240
ctggtcttac gtctccgcgg                                               260

<210> SEQ ID NO 2
<211> LENGTH: 86
<212> TYPE: PRT
<213> ORGANISM: artificial sequence
<220> FEATURE:
<223> OTHER INFORMATION: 6HisUbi, based on yeast source

<400> SEQUENCE: 2

Met Ala His His His His His His Ser Gly Ser Glu Phe Gln Ile Phe
1               5                   10                  15

Val Lys Thr Leu Thr Gly Lys Thr Ile Thr Leu Glu Val Glu Ser Ser
            20                  25                  30

Asp Thr Ile Asp Asn Val Lys Ser Lys Ile Gln Asp Lys Glu Gly Ile
        35                  40                  45

Pro Pro Asp Gln Gln Arg Leu Ile Phe Ala Gly Lys Gln Leu Glu Asp
    50                  55                  60

Gly Arg Thr Leu Ser Asp Tyr Asn Ile Gln Lys Glu Ser Thr Leu His
65                  70                  75                  80

Leu Val Leu Arg Leu Arg
                85

<210> SEQ ID NO 3
<211> LENGTH: 2520
<212> TYPE: DNA
<213> ORGANISM: artificial sequence
<220> FEATURE:
<223> OTHER INFORMATION: UBI::UBP1deltaC, based on yeast source
<220> FEATURE:
<221> NAME/KEY: CDS
<222> LOCATION: (1)..(2520)
<223> OTHER INFORMATION:

<400> SEQUENCE: 3 atg cag att ttc gtc aaa act ttg acc ggt aaa acc ata aca ttg gaa    48
Met Gln Ile Phe Val Lys Thr Leu Thr Gly Lys Thr Ile Thr Leu Glu
1               5                   10                  15 gtt gaa tct tcc gat acc atc gac aac gtt aag tcg aaa att caa gac    96
Val Glu Ser Ser Asp Thr Ile Asp Asn Val Lys Ser Lys Ile Gln Asp
            20                  25                  30 aag gaa ggt atc cct cca gat caa caa aga ttg atc ttt gcc ggt aag   144
Lys Glu Gly Ile Pro Pro Asp Gln Gln Arg Leu Ile Phe Ala Gly Lys
        35                  40                  45 cag cta gaa gac ggt aga acg ctg tct gat tac aac att cag aag gag   192
Gln Leu Glu Asp Gly Arg Thr Leu Ser Asp Tyr Asn Ile Gln Lys Glu

```
            50                  55                   60
tcc acc tta cat ctt gtc tta aga ctc cgc ggt ggt gac cat cta aac    240
Ser Thr Leu His Leu Val Leu Arg Leu Arg Gly Gly Asp His Leu Asn
 65                  70                  75                  80 tac att gtt gag agc gtt agt gaa atg aca aca aac ttc aga aat aat    288
Tyr Ile Val Glu Ser Val Ser Glu Met Thr Thr Asn Phe Arg Asn Asn
                     85                  90                  95 aat agc ctt agc cgt tgg ttg ccc aga agt aag ttt acc cac tta gac    336
Asn Ser Leu Ser Arg Trp Leu Pro Arg Ser Lys Phe Thr His Leu Asp
                100                 105                 110 gaa gag atc ttg aaa cgt ggt ggt ttc att gct ggt tta gtt aat gat    384
Glu Glu Ile Leu Lys Arg Gly Gly Phe Ile Ala Gly Leu Val Asn Asp
                115                 120                 125 ggt aac act tgt ttt atg aac tct gtt ttg caa tca ttg gca tca tcc    432
Gly Asn Thr Cys Phe Met Asn Ser Val Leu Gln Ser Leu Ala Ser Ser
130                 135                 140 aga gaa tta atg gag ttc ttg gac aat aat gtc ata agg acc tat gag    480
Arg Glu Leu Met Glu Phe Leu Asp Asn Asn Val Ile Arg Thr Tyr Glu
145                 150                 155                 160 gag ata gaa caa aat gaa cac aat gaa gaa gga aac ggg caa gaa tct    528
Glu Ile Glu Gln Asn Glu His Asn Glu Glu Gly Asn Gly Gln Glu Ser
                165                 170                 175 gct caa gat gaa gcc act cat aag aaa aac act cgt aag ggt ggc aaa    576
Ala Gln Asp Glu Ala Thr His Lys Lys Asn Thr Arg Lys Gly Gly Lys
                180                 185                 190 gtt tat ggt aag cat aag aag aaa ttg aat agg aag tca agt tcg aaa    624
Val Tyr Gly Lys His Lys Lys Lys Leu Asn Arg Lys Ser Ser Ser Lys
                195                 200                 205 gaa gac gaa gaa aag agc cag gag cca gat atc act ttc agt gtc gcc    672
Glu Asp Glu Glu Lys Ser Gln Glu Pro Asp Ile Thr Phe Ser Val Ala
210                 215                 220 tta agg gat cta ctt tct gcc tta aat gcg aag tat tat cgg gat aaa    720
Leu Arg Asp Leu Leu Ser Ala Leu Asn Ala Lys Tyr Tyr Arg Asp Lys
225                 230                 235                 240 ccc tat ttc aaa acc aat agt tta ttg aaa gca atg tcc aaa tct cca    768
Pro Tyr Phe Lys Thr Asn Ser Leu Leu Lys Ala Met Ser Lys Ser Pro
                245                 250                 255 aga aaa aat att ctt ctt ggc tac gac caa gag gac gcg caa gaa ttc    816
Arg Lys Asn Ile Leu Leu Gly Tyr Asp Gln Glu Asp Ala Gln Glu Phe
                260                 265                 270 ttc cag aac ata cta gcc gag ttg gaa agt aac gtt aaa tca ttg aat    864
Phe Gln Asn Ile Leu Ala Glu Leu Glu Ser Asn Val Lys Ser Leu Asn
                275                 280                 285 act gaa aaa cta gat acc act cca gtt gcg aaa tca gaa tta ccc gat    912
Thr Glu Lys Leu Asp Thr Thr Pro Val Ala Lys Ser Glu Leu Pro Asp
                290                 295                 300 gat gct tta gta ggt caa ctt aac ctt ggt gaa gtt ggc act gtt tac    960
Asp Ala Leu Val Gly Gln Leu Asn Leu Gly Glu Val Gly Thr Val Tyr
305                 310                 315                 320 att cca act gaa cag att gat cct aac tct ata cta cat gac aag tcc   1008
Ile Pro Thr Glu Gln Ile Asp Pro Asn Ser Ile Leu His Asp Lys Ser
                325                 330                 335 att caa aat ttc aca cct ttc aaa cta atg act cct tta gat ggt atc   1056
Ile Gln Asn Phe Thr Pro Phe Lys Leu Met Thr Pro Leu Asp Gly Ile
                340                 345                 350 acg gca gaa cgt att ggt tgt tta cag tgt ggt gag aac ggt ggc ata   1104
Thr Ala Glu Arg Ile Gly Cys Leu Gln Cys Gly Glu Asn Gly Gly Ile
                355                 360                 365 aga tat tcc gta ttt tcg gga ctg agc ctg aat ctg ccg aac gag aat   1152
Arg Tyr Ser Val Phe Ser Gly Leu Ser Leu Asn Leu Pro Asn Glu Asn
```

```
                    370                    375                    380
att gly tcc act ctg aaa ctg tct cag ctg ctg agc gac tgg agt aaa      1200
Ile Gly Ser Thr Leu Lys Leu Ser Gln Leu Leu Ser Asp Trp Ser Lys
385                    390                    395                    400 cct gaa atc atc gaa ggc gta gaa tgt aac cgt tgt gcc ctc aca gca      1248
Pro Glu Ile Ile Glu Gly Val Glu Cys Asn Arg Cys Ala Leu Thr Ala
                    405                    410                    415 gcg cac tct cat tta ttt ggt cag ttg aaa gaa ttt gaa aaa aaa cct      1296
Ala His Ser His Leu Phe Gly Gln Leu Lys Glu Phe Glu Lys Lys Pro
                420                    425                    430 gag ggt tcg atc cca gaa aag cca att aac gct gta aaa gat cgc gtc      1344
Glu Gly Ser Ile Pro Glu Lys Pro Ile Asn Ala Val Lys Asp Arg Val
                435                    440                    445 cat caa atc gaa gaa gtt ctt gcc aaa cca gtt att gac gat gaa gat      1392
His Gln Ile Glu Glu Val Leu Ala Lys Pro Val Ile Asp Asp Glu Asp
        450                    455                    460 tat aag aag ttg cat aca gca aat atg gta cgt aaa tgc tct aaa tct      1440
Tyr Lys Lys Leu His Thr Ala Asn Met Val Arg Lys Cys Ser Lys Ser
465                    470                    475                    480 aag cag att tta ata tca aga cct cca cca ctg ctg tcc att cat atc      1488
Lys Gln Ile Leu Ile Ser Arg Pro Pro Pro Leu Leu Ser Ile His Ile
                    485                    490                    495 aac cgt tcc gta ttt gat cca cgc acg tac atg att cgt aaa aat aac      1536
Asn Arg Ser Val Phe Asp Pro Arg Thr Tyr Met Ile Arg Lys Asn Asn
                500                    505                    510 tcg aaa gta ttg ttt aag tca agg ttg aat ctt gcc cca tgg tgt tgt      1584
Ser Lys Val Leu Phe Lys Ser Arg Leu Asn Leu Ala Pro Trp Cys Cys
            515                    520                    525 gat att aat gaa atc aat ttg gat gct cgt ttg cca atg tca aaa aag      1632
Asp Ile Asn Glu Ile Asn Leu Asp Ala Arg Leu Pro Met Ser Lys Lys
530                    535                    540 gaa aaa gct gcg caa caa gat tca agt gaa gat gaa aac att ggc ggt      1680
Glu Lys Ala Ala Gln Gln Asp Ser Ser Glu Asp Glu Asn Ile Gly Gly
545                    550                    555                    560 gaa tac tat acg aaa tta cat gaa cgc ttc gag cag gaa ttt gaa gac      1728
Glu Tyr Tyr Thr Lys Leu His Glu Arg Phe Glu Gln Glu Phe Glu Asp
                565                    570                    575 agc gag gaa gaa aaa gaa tac gat gac gca gag ggg aac tat gcg tct      1776
Ser Glu Glu Glu Lys Glu Tyr Asp Asp Ala Glu Gly Asn Tyr Ala Ser
                580                    585                    590 cat tac aat cat acc aag gat atc agt aac tat gat ccc cta aac ggt      1824
His Tyr Asn His Thr Lys Asp Ile Ser Asn Tyr Asp Pro Leu Asn Gly
            595                    600                    605 gaa gtc gat ggc gtg aca tcc gat gat gaa gat gag tac att gaa gaa      1872
Glu Val Asp Gly Val Thr Ser Asp Asp Glu Asp Glu Tyr Ile Glu Glu
610                    615                    620 acc gat gct tta ggg aat aca atc aaa aaa cgt atc ata gaa cat tct      1920
Thr Asp Ala Leu Gly Asn Thr Ile Lys Lys Arg Ile Ile Glu His Ser
625                    630                    635                    640 gat gtt gaa aac gag aat gta aaa gat aat gaa gaa ctg caa gaa atc      1968
Asp Val Glu Asn Glu Asn Val Lys Asp Asn Glu Glu Leu Gln Glu Ile
                645                    650                    655 gac aat gtg agc ctt gac gaa cca aag atc aat gtt gaa gat caa cta      2016
Asp Asn Val Ser Leu Asp Glu Pro Lys Ile Asn Val Glu Asp Gln Leu
                660                    665                    670 gaa aca tca tct gat gag gaa gat gtt ata cca gct cca cct atc aat      2064
Glu Thr Ser Ser Asp Glu Glu Asp Val Ile Pro Ala Pro Pro Ile Asn
            675                    680                    685 tat gct agg tca ttt tcc aca gtt cca gcc act cca ttg aca tat tca      2112
Tyr Ala Arg Ser Phe Ser Thr Val Pro Ala Thr Pro Leu Thr Tyr Ser
```

-continued

```
              690                 695                 700
ttg cgc tct gtc att gtt cac tac ggt acc cat aat tat ggt cat tac        2160
Leu Arg Ser Val Ile Val His Tyr Gly Thr His Asn Tyr Gly His Tyr
705                 710                 715                 720 att gca ttt cgt aaa tac cgt ggt tgt tgg tgg cgt ata tct gat gag        2208
Ile Ala Phe Arg Lys Tyr Arg Gly Cys Trp Trp Arg Ile Ser Asp Glu
            725                 730                 735 act gtg tac gtt gtg gac gaa gct gaa gtc ctt tca aca ccc ggt gta        2256
Thr Val Tyr Val Val Asp Glu Ala Glu Val Leu Ser Thr Pro Gly Val
        740                 745                 750 ttt atg tta ttt tac gaa tat gac ttt gat gaa gaa act ggg aag atg        2304
Phe Met Leu Phe Tyr Glu Tyr Asp Phe Asp Glu Glu Thr Gly Lys Met
    755                 760                 765 aag gat gat ttg gaa gct att ctg agt aat aat gaa gaa gat gat gaa        2352
Lys Asp Asp Leu Glu Ala Ile Leu Ser Asn Asn Glu Glu Asp Asp Glu
770                 775                 780 aaa gag cag gag caa aaa gga gtc cag gag cca aag gaa agc caa gag        2400
Lys Glu Gln Glu Gln Lys Gly Val Gln Glu Pro Lys Glu Ser Gln Glu
785                 790                 795                 800 caa gga gaa ggt gaa gag caa gag gaa ggt caa gag cag atg aag ttc        2448
Gln Gly Glu Gly Glu Glu Gln Glu Glu Gly Gln Glu Gln Met Lys Phe
                805                 810                 815 gag cgt aca gaa gac cat cgc gat att tct ggt aaa gat gta aac gga        2496
Glu Arg Thr Glu Asp His Arg Asp Ile Ser Gly Lys Asp Val Asn Gly
            820                 825                 830 tcc cat cat cac cat cac cat taa                                        2520
Ser His His His His His His
        835
```

<210> SEQ ID NO 4
<211> LENGTH: 839
<212> TYPE: PRT
<213> ORGANISM: artificial sequence
<220> FEATURE:
<223> OTHER INFORMATION: UBI::UBP1deltaC, based on yeast source

<400> SEQUENCE: 4

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Asp His Leu Asn
65                  70                  75                  80

Tyr Ile Val Glu Ser Val Ser Glu Met Thr Thr Asn Phe Arg Asn Asn
                85                  90                  95

Asn Ser Leu Ser Arg Trp Leu Pro Arg Ser Lys Phe Thr His Leu Asp
            100                 105                 110

Glu Glu Ile Leu Lys Arg Gly Gly Phe Ile Ala Gly Leu Val Asn Asp
        115                 120                 125

Gly Asn Thr Cys Phe Met Asn Ser Val Leu Gln Ser Leu Ala Ser Ser
    130                 135                 140

Arg Glu Leu Met Glu Phe Leu Asp Asn Asn Val Ile Arg Thr Tyr Glu
145                 150                 155                 160

Glu Ile Glu Gln Asn Glu His Asn Glu Glu Gly Asn Gly Gln Glu Ser
                165                 170                 175
```

```
Ala Gln Asp Glu Ala Thr His Lys Lys Asn Thr Arg Lys Gly Gly Lys
            180                 185                 190

Val Tyr Gly Lys His Lys Lys Leu Asn Arg Lys Ser Ser Ser Lys
        195                 200                 205

Glu Asp Glu Glu Lys Ser Gln Glu Pro Asp Ile Thr Phe Ser Val Ala
    210                 215                 220

Leu Arg Asp Leu Leu Ser Ala Leu Asn Ala Lys Tyr Tyr Arg Asp Lys
225                 230                 235                 240

Pro Tyr Phe Lys Thr Asn Ser Leu Leu Lys Ala Met Ser Lys Ser Pro
                245                 250                 255

Arg Lys Asn Ile Leu Leu Gly Tyr Asp Gln Glu Asp Ala Gln Glu Phe
            260                 265                 270

Phe Gln Asn Ile Leu Ala Glu Leu Glu Ser Asn Val Lys Ser Leu Asn
        275                 280                 285

Thr Glu Lys Leu Asp Thr Thr Pro Val Ala Lys Ser Glu Leu Pro Asp
    290                 295                 300

Asp Ala Leu Val Gly Gln Leu Asn Leu Gly Glu Val Gly Thr Val Tyr
305                 310                 315                 320

Ile Pro Thr Glu Gln Ile Asp Pro Asn Ser Ile Leu His Asp Lys Ser
                325                 330                 335

Ile Gln Asn Phe Thr Pro Phe Lys Leu Met Thr Pro Leu Asp Gly Ile
            340                 345                 350

Thr Ala Glu Arg Ile Gly Cys Leu Gln Cys Gly Glu Asn Gly Gly Ile
        355                 360                 365

Arg Tyr Ser Val Phe Ser Gly Leu Ser Leu Asn Leu Pro Asn Glu Asn
    370                 375                 380

Ile Gly Ser Thr Leu Lys Leu Ser Gln Leu Leu Ser Asp Trp Ser Lys
385                 390                 395                 400

Pro Glu Ile Ile Glu Gly Val Glu Cys Asn Arg Cys Ala Leu Thr Ala
                405                 410                 415

Ala His Ser His Leu Phe Gly Gln Leu Lys Glu Phe Glu Lys Lys Pro
            420                 425                 430

Glu Gly Ser Ile Pro Glu Lys Pro Ile Asn Ala Val Lys Asp Arg Val
        435                 440                 445

His Gln Ile Glu Glu Val Leu Ala Lys Pro Val Ile Asp Asp Glu Asp
    450                 455                 460

Tyr Lys Lys Leu His Thr Ala Asn Met Val Arg Lys Cys Ser Lys Ser
465                 470                 475                 480

Lys Gln Ile Leu Ile Ser Arg Pro Pro Leu Leu Ser Ile His Ile
                485                 490                 495

Asn Arg Ser Val Phe Asp Pro Arg Thr Tyr Met Ile Arg Lys Asn Asn
            500                 505                 510

Ser Lys Val Leu Phe Lys Ser Arg Leu Asn Leu Ala Pro Trp Cys Cys
        515                 520                 525

Asp Ile Asn Glu Ile Asn Leu Asp Ala Arg Leu Pro Met Ser Lys Lys
    530                 535                 540

Glu Lys Ala Ala Gln Gln Asp Ser Ser Glu Asp Asn Ile Gly Gly
545                 550                 555                 560

Glu Tyr Tyr Thr Lys Leu His Glu Arg Phe Gln Glu Phe Glu Asp
                565                 570                 575

Ser Glu Glu Glu Lys Glu Tyr Asp Asp Ala Glu Gly Asn Tyr Ala Ser
            580                 585                 590

His Tyr Asn His Thr Lys Asp Ile Ser Asn Tyr Asp Pro Leu Asn Gly
```

```
                595                 600                 605
Glu Val Asp Gly Val Thr Ser Asp Asp Glu Asp Tyr Ile Glu Glu
        610                 615                 620

Thr Asp Ala Leu Gly Asn Thr Ile Lys Lys Arg Ile Glu His Ser
625                 630                 635                 640

Asp Val Glu Asn Glu Asn Val Lys Asp Asn Glu Leu Gln Glu Ile
                645                 650                 655

Asp Asn Val Ser Leu Asp Glu Pro Lys Ile Asn Val Glu Asp Gln Leu
            660                 665                 670

Glu Thr Ser Ser Asp Glu Glu Asp Val Ile Pro Ala Pro Pro Ile Asn
        675                 680                 685

Tyr Ala Arg Ser Phe Ser Thr Val Pro Ala Thr Pro Leu Thr Tyr Ser
    690                 695                 700

Leu Arg Ser Val Ile Val His Tyr Gly Thr His Asn Tyr Gly His Tyr
705                 710                 715                 720

Ile Ala Phe Arg Lys Tyr Arg Gly Cys Trp Trp Arg Ile Ser Asp Glu
                725                 730                 735

Thr Val Tyr Val Val Asp Glu Ala Glu Val Leu Ser Thr Pro Gly Val
            740                 745                 750

Phe Met Leu Phe Tyr Glu Tyr Asp Phe Asp Glu Glu Thr Gly Lys Met
        755                 760                 765

Lys Asp Asp Leu Glu Ala Ile Leu Ser Asn Asn Glu Asp Asp Glu
770                 775                 780

Lys Glu Gln Glu Gln Lys Gly Val Gln Glu Pro Lys Glu Ser Gln Glu
785                 790                 795                 800

Gln Gly Glu Gly Glu Glu Gln Glu Gly Gln Glu Gln Met Lys Phe
            805                 810                 815

Glu Arg Thr Glu Asp His Arg Asp Ile Ser Gly Lys Asp Val Asn Gly
        820                 825                 830

Ser His His His His His His
        835

<210> SEQ ID NO 5
<211> LENGTH: 2166
<212> TYPE: DNA
<213> ORGANISM: artificial sequence
<220> FEATURE:
<223> OTHER INFORMATION: UBP1deltaC2, based on yeast source
<220> FEATURE:
<221> NAME/KEY: CDS
<222> LOCATION: (1)..(2166)
<223> OTHER INFORMATION:

<400> SEQUENCE: 5 ggt ggt ttc att gct ggt tta gtt aat gat ggt aac act tgt ttt atg     48
Gly Gly Phe Ile Ala Gly Leu Val Asn Asp Gly Asn Thr Cys Phe Met
1               5                   10                  15 aac tct gtt ttg caa tca ttg gca tca tcc aga gaa tta atg gag ttc     96
Asn Ser Val Leu Gln Ser Leu Ala Ser Ser Arg Glu Leu Met Glu Phe
            20                  25                  30 ttg gac aat aat gtc ata agg acc tat gag gag ata gaa caa aat gaa    144
Leu Asp Asn Asn Val Ile Arg Thr Tyr Glu Glu Ile Glu Gln Asn Glu
        35                  40                  45 cac aat gaa gaa gga aac ggg caa gaa tct gct caa gat gaa gcc act    192
His Asn Glu Glu Gly Asn Gly Gln Glu Ser Ala Gln Asp Glu Ala Thr
    50                  55                  60 cat aag aaa aac act cgt aag ggt ggc aaa gtt tat ggt aag cat aag    240
His Lys Lys Asn Thr Arg Lys Gly Gly Lys Val Tyr Gly Lys His Lys
65                  70                  75                  80
```

| | | |
|---|---|---|
| aag aaa ttg aat agg aag tca agt tcg aaa gaa gac gaa gaa aag agc<br>Lys Lys Leu Asn Arg Lys Ser Ser Ser Lys Glu Asp Glu Glu Lys Ser<br>                85                    90                  95 | 288 |
| cag gag cca gat atc act ttc agt gtc gcc tta agg gat cta ctt tct<br>Gln Glu Pro Asp Ile Thr Phe Ser Val Ala Leu Arg Asp Leu Leu Ser<br>100                         105                       110 | 336 |
| gcc tta aat gcg aag tat tat cgg gat aaa ccc tat ttc aaa acc aat<br>Ala Leu Asn Ala Lys Tyr Tyr Arg Asp Lys Pro Tyr Phe Lys Thr Asn<br>         115                     120                   125 | 384 |
| agt tta ttg aaa gca atg tcc aaa tct cca aga aaa aat att ctt ctt<br>Ser Leu Leu Lys Ala Met Ser Lys Ser Pro Arg Lys Asn Ile Leu Leu<br>130                       135                     140 | 432 |
| ggc tac gac caa gag gac gcg caa gaa ttc ttc cag aac ata cta gcc<br>Gly Tyr Asp Gln Glu Asp Ala Gln Glu Phe Phe Gln Asn Ile Leu Ala<br>145                     150                    155                 160 | 480 |
| gag ttg gaa agt aac gtt aaa tca ttg aat act gaa aaa cta gat acc<br>Glu Leu Glu Ser Asn Val Lys Ser Leu Asn Thr Glu Lys Leu Asp Thr<br>                165                   170                   175 | 528 |
| act cca gtt gcg aaa tca gaa tta ccc gat gat gct tta gta ggt caa<br>Thr Pro Val Ala Lys Ser Glu Leu Pro Asp Asp Ala Leu Val Gly Gln<br>                   180                     185                 190 | 576 |
| ctt aac ctt ggt gaa gtt ggc act gtt tac att cca act gaa cag att<br>Leu Asn Leu Gly Glu Val Gly Thr Val Tyr Ile Pro Thr Glu Gln Ile<br>        195                     200                     205 | 624 |
| gat cct aac tct ata cta cat gac aag tcc att caa aat ttc aca cct<br>Asp Pro Asn Ser Ile Leu His Asp Lys Ser Ile Gln Asn Phe Thr Pro<br>210                     215                     220 | 672 |
| ttc aaa cta atg act cct tta gat ggt atc acg gca gaa cgt att ggt<br>Phe Lys Leu Met Thr Pro Leu Asp Gly Ile Thr Ala Glu Arg Ile Gly<br>225                     230                    235                 240 | 720 |
| tgt tta cag tgt ggt gag aac ggt ggc ata aga tat tcc gta ttt tcg<br>Cys Leu Gln Cys Gly Glu Asn Gly Gly Ile Arg Tyr Ser Val Phe Ser<br>                   245                     250                 255 | 768 |
| gga ctg agc ctg aat ctg ccg aac gag aat att ggt tcc act ctg aaa<br>Gly Leu Ser Leu Asn Leu Pro Asn Glu Asn Ile Gly Ser Thr Leu Lys<br>        260                     265                     270 | 816 |
| ctg tct cag ctg ctg agc gac tgg agt aaa cct gaa atc atc gaa ggc<br>Leu Ser Gln Leu Leu Ser Asp Trp Ser Lys Pro Glu Ile Ile Glu Gly<br>         275                     280                   285 | 864 |
| gta gaa tgt aac cgt tgt gcc ctc aca gca gcg cac tct cat tta ttt<br>Val Glu Cys Asn Arg Cys Ala Leu Thr Ala Ala His Ser His Leu Phe<br>290                     295                     300 | 912 |
| ggt cag ttg aaa gaa ttt gaa aaa aaa cct gag ggt tcg atc cca gaa<br>Gly Gln Leu Lys Glu Phe Glu Lys Lys Pro Glu Gly Ser Ile Pro Glu<br>305                     310                    315                 320 | 960 |
| aag cca att aac gct gta aaa gat cgc gtc cat caa atc gaa gaa gtt<br>Lys Pro Ile Asn Ala Val Lys Asp Arg Val His Gln Ile Glu Glu Val<br>                   325                     330                   335 | 1008 |
| ctt gcc aaa cca gtt att gac gat gaa gat tat aag aag ttg cat aca<br>Leu Ala Lys Pro Val Ile Asp Asp Glu Asp Tyr Lys Lys Leu His Thr<br>                 340                     345                   350 | 1056 |
| gca aat atg gta cgt aaa tgc tct aaa tct aag cag att tta ata tca<br>Ala Asn Met Val Arg Lys Cys Ser Lys Ser Lys Gln Ile Leu Ile Ser<br>        355                     360                     365 | 1104 |
| aga cct cca cca ctg ctg tcc att cat atc aac cgt tcc gta ttt gat<br>Arg Pro Pro Pro Leu Leu Ser Ile His Ile Asn Arg Ser Val Phe Asp<br>        370                     375                     380 | 1152 |
| cca cgc acg tac atg att cgt aaa aat aac tcg aaa gta ttg ttt aag<br>Pro Arg Thr Tyr Met Ile Arg Lys Asn Asn Ser Lys Val Leu Phe Lys<br>385                     390                    395                 400 | 1200 |

| | | |
|---|---|---|
| tca agg ttg aat ctt gcc cca tgg tgt tgt gat att aat gaa atc aat<br>Ser Arg Leu Asn Leu Ala Pro Trp Cys Cys Asp Ile Asn Glu Ile Asn<br>405 410 415 | | 1248 |
| ttg gat gct cgt ttg cca atg tca aaa aag gaa aaa gct gcg caa caa<br>Leu Asp Ala Arg Leu Pro Met Ser Lys Lys Glu Lys Ala Ala Gln Gln<br>420 425 430 | | 1296 |
| gat tca agt gaa gat gaa aac att ggc ggt gaa tac tat acg aaa tta<br>Asp Ser Ser Glu Asp Glu Asn Ile Gly Gly Glu Tyr Tyr Thr Lys Leu<br>435 440 445 | | 1344 |
| cat gaa cgc ttc gag cag gaa ttt gaa gac agc gag gaa gaa aaa gaa<br>His Glu Arg Phe Glu Gln Glu Phe Glu Asp Ser Glu Glu Glu Lys Glu<br>450 455 460 | | 1392 |
| tac gat gac gca gag ggg aac tat gcg tct cat tac aat cat acc aag<br>Tyr Asp Asp Ala Glu Gly Asn Tyr Ala Ser His Tyr Asn His Thr Lys<br>465 470 475 480 | | 1440 |
| gat atc agt aac tat gat ccc cta aac ggt gaa gtc gat ggc gtg aca<br>Asp Ile Ser Asn Tyr Asp Pro Leu Asn Gly Glu Val Asp Gly Val Thr<br>485 490 495 | | 1488 |
| tcc gat gat gaa gat gag tac att gaa gaa acc gat gct tta ggg aat<br>Ser Asp Asp Glu Asp Glu Tyr Ile Glu Glu Thr Asp Ala Leu Gly Asn<br>500 505 510 | | 1536 |
| aca atc aaa aaa cgt atc ata gaa cat tct gat gtt gaa aac gag aat<br>Thr Ile Lys Lys Arg Ile Ile Glu His Ser Asp Val Glu Asn Glu Asn<br>515 520 525 | | 1584 |
| gta aaa gat aat gaa gaa ctg caa gaa atc gac aat gtg agc ctt gac<br>Val Lys Asp Asn Glu Glu Leu Gln Glu Ile Asp Asn Val Ser Leu Asp<br>530 535 540 | | 1632 |
| gaa cca aag atc aat gtt gaa gat caa cta gaa aca tca tct gat gag<br>Glu Pro Lys Ile Asn Val Glu Asp Gln Leu Glu Thr Ser Ser Asp Glu<br>545 550 555 560 | | 1680 |
| gaa gat gtt ata cca gct cca cct atc aat tat gct agg tca ttt tcc<br>Glu Asp Val Ile Pro Ala Pro Pro Ile Asn Tyr Ala Arg Ser Phe Ser<br>565 570 575 | | 1728 |
| aca gtt cca gcc act cca ttg aca tat tca ttg cgc tct gtc att gtt<br>Thr Val Pro Ala Thr Pro Leu Thr Tyr Ser Leu Arg Ser Val Ile Val<br>580 585 590 | | 1776 |
| cac tac ggt acc cat aat tat ggt cat tac att gca ttt cgt aaa tac<br>His Tyr Gly Thr His Asn Tyr Gly His Tyr Ile Ala Phe Arg Lys Tyr<br>595 600 605 | | 1824 |
| cgt ggt tgt tgg tgg cgt ata tct gat gag act gtg tac gtt gtg gac<br>Arg Gly Cys Trp Trp Arg Ile Ser Asp Glu Thr Val Tyr Val Val Asp<br>610 615 620 | | 1872 |
| gaa gct gaa gtc ctt tca aca ccc ggt gta ttt atg tta ttt tac gaa<br>Glu Ala Glu Val Leu Ser Thr Pro Gly Val Phe Met Leu Phe Tyr Glu<br>625 630 635 640 | | 1920 |
| tat gac ttt gat gaa gaa act ggg aag atg aag gat gat ttg gaa gct<br>Tyr Asp Phe Asp Glu Glu Thr Gly Lys Met Lys Asp Asp Leu Glu Ala<br>645 650 655 | | 1968 |
| att ctg agt aat aat gaa gaa gat gat gaa aaa gag cag gag caa aaa<br>Ile Leu Ser Asn Asn Glu Glu Asp Asp Glu Lys Glu Gln Glu Gln Lys<br>660 665 670 | | 2016 |
| gga gtc cag gag cca aag gaa agc caa gag caa gga gaa ggt gaa gag<br>Gly Val Gln Glu Pro Lys Glu Ser Gln Glu Gln Gly Glu Gly Glu Glu<br>675 680 685 | | 2064 |
| caa gag gaa ggt caa gag cag atg aag ttc gag cgt aca gaa gac cat<br>Gln Glu Glu Gly Gln Glu Gln Met Lys Phe Glu Arg Thr Glu Asp His<br>690 695 700 | | 2112 |
| cgc gat att tct ggt aaa gat gta aac gga tcc cat cat cac cat cac<br>Arg Asp Ile Ser Gly Lys Asp Val Asn Gly Ser His His His His His<br>705 710 715 720 | | 2160 | cat taa　　　　　　　　　　　　　　　　　　　　　　　　　　　　　　　　　　　　　　　　　2166
His

<210> SEQ ID NO 6
<211> LENGTH: 719
<212> TYPE: PRT
<213> ORGANISM: artificial sequence
<220> FEATURE:
<223> OTHER INFORMATION: UBP1deltaC2,based on yeast source

<400> SEQUENCE: 6

```
Phe Ile Ala Gly Leu Val Asn Asp Gly Asn Thr Cys Phe Met Asn Ser
 1               5                  10                  15

Val Leu Gln Ser Leu Ala Ser Ser Arg Glu Leu Met Glu Phe Leu Asp
            20                  25                  30

Asn Asn Val Ile Arg Thr Tyr Glu Glu Ile Glu Gln Asn Glu His Asn
        35                  40                  45

Glu Glu Gly Asn Gly Gln Glu Ser Ala Gln Asp Glu Ala Thr His Lys
    50                  55                  60

Lys Asn Thr Arg Lys Gly Gly Lys Val Tyr Gly Lys His Lys Lys Lys
65                  70                  75                  80

Leu Asn Arg Lys Ser Ser Lys Glu Asp Glu Glu Lys Ser Gln Glu
                85                  90                  95

Pro Asp Ile Thr Phe Ser Val Ala Leu Arg Asp Leu Leu Ser Ala Leu
            100                 105                 110

Asn Ala Lys Tyr Tyr Arg Asp Lys Pro Tyr Phe Lys Thr Asn Ser Leu
        115                 120                 125

Leu Lys Ala Met Ser Lys Ser Pro Arg Lys Asn Ile Leu Leu Gly Tyr
    130                 135                 140

Asp Gln Glu Asp Ala Gln Glu Phe Phe Gln Asn Ile Leu Ala Glu Leu
145                 150                 155                 160

Glu Ser Asn Val Lys Ser Leu Asn Thr Glu Lys Leu Asp Thr Thr Pro
                165                 170                 175

Val Ala Lys Ser Glu Leu Pro Asp Asp Ala Leu Val Gly Gln Leu Asn
            180                 185                 190

Leu Gly Glu Val Gly Thr Val Tyr Ile Pro Thr Glu Gln Ile Asp Pro
        195                 200                 205

Asn Ser Ile Leu His Asp Lys Ser Ile Gln Asn Phe Thr Pro Phe Lys
    210                 215                 220

Leu Met Thr Pro Leu Asp Gly Ile Thr Ala Glu Arg Ile Gly Cys Leu
225                 230                 235                 240

Gln Cys Gly Glu Asn Gly Gly Ile Arg Tyr Ser Val Phe Ser Gly Leu
                245                 250                 255

Ser Leu Asn Leu Pro Asn Glu Asn Ile Gly Ser Thr Leu Lys Leu Ser
            260                 265                 270

Gln Leu Leu Ser Asp Trp Ser Lys Pro Glu Ile Ile Glu Gly Val Glu
        275                 280                 285

Cys Asn Arg Cys Ala Leu Thr Ala Ala His Ser His Leu Phe Gly Gln
    290                 295                 300

Leu Lys Glu Phe Glu Lys Pro Glu Gly Ser Ile Pro Glu Lys Pro
305                 310                 315                 320

Ile Asn Ala Val Lys Asp Arg Val His Gln Ile Glu Glu Val Leu Ala
                325                 330                 335

Lys Pro Val Ile Asp Asp Glu Asp Tyr Lys Lys Leu His Thr Ala Asn
            340                 345                 350
```

```
Met Val Arg Lys Cys Ser Lys Ser Lys Gln Ile Leu Ile Ser Arg Pro
        355                 360                 365

Pro Pro Leu Leu Ser Ile His Ile Asn Arg Ser Val Phe Asp Pro Arg
        370                 375                 380

Thr Tyr Met Ile Arg Lys Asn Asn Ser Lys Val Leu Phe Lys Ser Arg
385                 390                 395                 400

Leu Asn Leu Ala Pro Trp Cys Cys Asp Ile Asn Glu Ile Asn Leu Asp
                405                 410                 415

Ala Arg Leu Pro Met Ser Lys Lys Glu Lys Ala Ala Gln Gln Asp Ser
                420                 425                 430

Ser Glu Asp Glu Asn Ile Gly Gly Glu Tyr Tyr Thr Lys Leu His Glu
            435                 440                 445

Arg Phe Glu Gln Glu Phe Glu Asp Ser Glu Glu Lys Glu Tyr Asp
        450                 455                 460

Asp Ala Glu Gly Asn Tyr Ala Ser His Tyr Asn His Thr Lys Asp Ile
465                 470                 475                 480

Ser Asn Tyr Asp Pro Leu Asn Gly Glu Val Asp Gly Val Thr Ser Asp
                485                 490                 495

Asp Glu Asp Glu Tyr Ile Glu Glu Thr Asp Ala Leu Gly Asn Thr Ile
            500                 505                 510

Lys Lys Arg Ile Ile Glu His Ser Asp Val Glu Asn Glu Asn Val Lys
        515                 520                 525

Asp Asn Glu Glu Leu Gln Glu Ile Asp Asn Val Ser Leu Asp Glu Pro
        530                 535                 540

Lys Ile Asn Val Glu Asp Gln Leu Glu Thr Ser Ser Asp Glu Glu Asp
545                 550                 555                 560

Val Ile Pro Ala Pro Pro Ile Asn Tyr Ala Arg Ser Phe Ser Thr Val
                565                 570                 575

Pro Ala Thr Pro Leu Thr Tyr Ser Leu Arg Ser Val Ile Val His Tyr
            580                 585                 590

Gly Thr His Asn Tyr Gly His Tyr Ile Ala Phe Arg Lys Tyr Arg Gly
        595                 600                 605

Cys Trp Trp Arg Ile Ser Asp Glu Thr Val Tyr Val Val Asp Glu Ala
        610                 615                 620

Glu Val Leu Ser Thr Pro Gly Val Phe Met Leu Phe Tyr Glu Tyr Asp
625                 630                 635                 640

Phe Asp Glu Glu Thr Gly Lys Met Lys Asp Asp Leu Glu Ala Ile Leu
                645                 650                 655

Ser Asn Asn Glu Glu Asp Asp Glu Lys Glu Gln Glu Lys Gly Val
            660                 665                 670

Gln Glu Pro Lys Glu Ser Gln Glu Gln Gly Gly Glu Gln Glu
        675                 680                 685

Glu Gly Gln Glu Gln Met Lys Phe Glu Arg Thr Glu Asp His Arg Asp
        690                 695                 700

Ile Ser Gly Lys Asp Val Asn Gly Ser His His His His His
705                 710                 715

<210> SEQ ID NO 7
<211> LENGTH: 621
<212> TYPE: DNA
<213> ORGANISM: artificial sequence
<220> FEATURE:
<223> OTHER INFORMATION: 6HisUbi::ElisaC, based on yeast source
<220> FEATURE:
<221> NAME/KEY: CDS
<222> LOCATION: (1)..(621)
<223> OTHER INFORMATION:
```

<400> SEQUENCE: 7

```
atg gca cat cat cac cat cac cac tct ggt tct gaa ttc caa att ttt      48
Met Ala His His His His His His Ser Gly Ser Glu Phe Gln Ile Phe
1               5                   10                  15 gtt aaa act tta act ggt aaa acc att acc tta gaa gtt gaa tct tca      96
Val Lys Thr Leu Thr Gly Lys Thr Ile Thr Leu Glu Val Glu Ser Ser
            20                  25                  30 gat acc att gat aat gtt aaa tct aaa att caa gat aaa gaa ggt att     144
Asp Thr Ile Asp Asn Val Lys Ser Lys Ile Gln Asp Lys Glu Gly Ile
        35                  40                  45 cct cca gat caa caa cgt cta ata ttt gca ggt aaa cag tta gaa gat     192
Pro Pro Asp Gln Gln Arg Leu Ile Phe Ala Gly Lys Gln Leu Glu Asp
    50                  55                  60 ggt cgt acc ctg tct gat tat aac att cag aaa gaa tct acc tta cat     240
Gly Arg Thr Leu Ser Asp Tyr Asn Ile Gln Lys Glu Ser Thr Leu His
65                  70                  75                  80 ctg gtc tta cgt ctc cgc ggt ggt acc cat aat tat ggt cat tac att     288
Leu Val Leu Arg Leu Arg Gly Gly Thr His Asn Tyr Gly His Tyr Ile
                85                  90                  95 gca ttt cgt aaa tac cgt ggt tgt tgg tgg cgt ata tct gat gag act     336
Ala Phe Arg Lys Tyr Arg Gly Cys Trp Trp Arg Ile Ser Asp Glu Thr
            100                 105                 110 gtg tac gtt gtg gac gaa gct gaa gtc ctt tca aca ccc ggt gta ttt     384
Val Tyr Val Val Asp Glu Ala Glu Val Leu Ser Thr Pro Gly Val Phe
        115                 120                 125 atg tta ttt tac gaa tat gac ttt gat gaa gaa act ggg aag atg aag     432
Met Leu Phe Tyr Glu Tyr Asp Phe Asp Glu Glu Thr Gly Lys Met Lys
    130                 135                 140 gat gat ttg gaa gct att ctg agt aat aat gaa gaa gat gat gaa aaa     480
Asp Asp Leu Glu Ala Ile Leu Ser Asn Asn Glu Glu Asp Asp Glu Lys
145                 150                 155                 160 gag cag gag caa aaa gga gtc cag gag cca aag gaa agc caa gag caa     528
Glu Gln Glu Gln Lys Gly Val Gln Glu Pro Lys Glu Ser Gln Glu Gln
                165                 170                 175 gga gaa ggt gaa gag caa gag gaa ggt caa gag cag atg aag ttc gag     576
Gly Glu Gly Glu Glu Gln Glu Glu Gly Gln Glu Gln Met Lys Phe Glu
            180                 185                 190 cgt aca gaa gac cat cgc gat att tct ggt aaa gat gta aac taa        621
Arg Thr Glu Asp His Arg Asp Ile Ser Gly Lys Asp Val Asn
        195                 200                 205
```

<210> SEQ ID NO 8
<211> LENGTH: 206
<212> TYPE: PRT
<213> ORGANISM: artificial sequence
<220> FEATURE:
<223> OTHER INFORMATION: 6HisUbi::ElisaC, based on yeast source

<400> SEQUENCE: 8

```
Met Ala His His His His His His Ser Gly Ser Glu Phe Gln Ile Phe
1               5                   10                  15

Val Lys Thr Leu Thr Gly Lys Thr Ile Thr Leu Glu Val Glu Ser Ser
            20                  25                  30

Asp Thr Ile Asp Asn Val Lys Ser Lys Ile Gln Asp Lys Glu Gly Ile
        35                  40                  45

Pro Pro Asp Gln Gln Arg Leu Ile Phe Ala Gly Lys Gln Leu Glu Asp
    50                  55                  60

Gly Arg Thr Leu Ser Asp Tyr Asn Ile Gln Lys Glu Ser Thr Leu His
65                  70                  75                  80
```

```
Leu Val Leu Arg Leu Arg Gly Gly Thr His Asn Tyr Gly His Tyr Ile
             85                  90                  95

Ala Phe Arg Lys Tyr Arg Gly Cys Trp Trp Arg Ile Ser Asp Glu Thr
            100                 105                 110

Val Tyr Val Val Asp Glu Ala Glu Val Leu Ser Thr Pro Gly Val Phe
            115                 120                 125

Met Leu Phe Tyr Glu Tyr Asp Phe Asp Glu Glu Thr Gly Lys Met Lys
            130                 135                 140

Asp Asp Leu Glu Ala Ile Leu Ser Asn Asn Glu Glu Asp Asp Glu Lys
145                 150                 155                 160

Glu Gln Glu Gln Lys Gly Val Gln Glu Pro Lys Glu Ser Gln Glu Gln
                165                 170                 175

Gly Glu Gly Glu Glu Gln Glu Glu Gly Gln Glu Gln Met Lys Phe Glu
            180                 185                 190

Arg Thr Glu Asp His Arg Asp Ile Ser Gly Lys Asp Val Asn
            195                 200                 205

<210> SEQ ID NO 9
<211> LENGTH: 2388
<212> TYPE: DNA
<213> ORGANISM: artificial sequence
<220> FEATURE:
<223> OTHER INFORMATION: UBI::UBP1deltaC2, based on yeast source
<220> FEATURE:
<221> NAME/KEY: CDS
<222> LOCATION: (1)..(2388)
<223> OTHER INFORMATION:

<400> SEQUENCE: 9 atg cag att ttc gtc aaa act ttg acc ggt aaa acc ata aca ttg gaa      48
Met Gln Ile Phe Val Lys Thr Leu Thr Gly Lys Thr Ile Thr Leu Glu
1               5                   10                  15 gtt gaa tct tcc gat acc atc gac aac gtt aag tcg aaa att caa gac      96
Val Glu Ser Ser Asp Thr Ile Asp Asn Val Lys Ser Lys Ile Gln Asp
                20                  25                  30 aag gaa ggt atc cct cca gat caa caa aga ttg atc ttt gcc ggt aag     144
Lys Glu Gly Ile Pro Pro Asp Gln Gln Arg Leu Ile Phe Ala Gly Lys
            35                  40                  45 cag cta gaa gac ggt aga acg ctg tct gat tac aac att cag aag gag     192
Gln Leu Glu Asp Gly Arg Thr Leu Ser Asp Tyr Asn Ile Gln Lys Glu
        50                  55                  60 tcc acc tta cat ctt gtc tta aga ctc cgc ggt ggt ttc att gct ggt     240
Ser Thr Leu His Leu Val Leu Arg Leu Arg Gly Gly Phe Ile Ala Gly
65                  70                  75                  80 tta gtt aat gat ggt aac act tgt ttt atg aac tct gtt ttg caa tca     288
Leu Val Asn Asp Gly Asn Thr Cys Phe Met Asn Ser Val Leu Gln Ser
                85                  90                  95 ttg gca tca tcc aga gaa tta atg gag ttc ttg gac aat aat gtc ata     336
Leu Ala Ser Ser Arg Glu Leu Met Glu Phe Leu Asp Asn Asn Val Ile
            100                 105                 110 agg acc tat gag gag ata gaa caa aat gaa cac aat gaa gaa gga aac     384
Arg Thr Tyr Glu Glu Ile Glu Gln Asn Glu His Asn Glu Glu Gly Asn
        115                 120                 125 ggg caa gaa tct gct caa gat gaa gcc act cat aag aaa aac act cgt     432
Gly Gln Glu Ser Ala Gln Asp Glu Ala Thr His Lys Lys Asn Thr Arg
    130                 135                 140 aag ggt ggc aaa gtt tat ggt aag cat aag aag aaa ttg aat agg aag     480
Lys Gly Gly Lys Val Tyr Gly Lys His Lys Lys Lys Leu Asn Arg Lys
145                 150                 155                 160 tca agt tcg aaa gaa gac gaa gaa aag agc cag gag cca gat atc act     528
Ser Ser Ser Lys Glu Asp Glu Glu Lys Ser Gln Glu Pro Asp Ile Thr
```

```
                        165                 170                 175
ttc agt gtc gcc tta agg gat cta ctt tct gcc tta aat gcg aag tat    576
Phe Ser Val Ala Leu Arg Asp Leu Leu Ser Ala Leu Asn Ala Lys Tyr
        180                 185                 190 tat cgg gat aaa ccc tat ttc aaa acc aat agt tta ttg aaa gca atg    624
Tyr Arg Asp Lys Pro Tyr Phe Lys Thr Asn Ser Leu Leu Lys Ala Met
195                 200                 205 tcc aaa tct cca aga aaa aat att ctt ctt ggc tac gac caa gag gac    672
Ser Lys Ser Pro Arg Lys Asn Ile Leu Leu Gly Tyr Asp Gln Glu Asp
    210                 215                 220 gcg caa gaa ttc ttc cag aac ata cta gcc gag ttg gaa agt aac gtt    720
Ala Gln Glu Phe Phe Gln Asn Ile Leu Ala Glu Leu Glu Ser Asn Val
225                 230                 235                 240 aaa tca ttg aat act gaa aaa cta gat acc act cca gtt gcg aaa tca    768
Lys Ser Leu Asn Thr Glu Lys Leu Asp Thr Thr Pro Val Ala Lys Ser
            245                 250                 255 gaa tta ccc gat gat gct tta gta ggt caa ctt aac ctt ggt gaa gtt    816
Glu Leu Pro Asp Asp Ala Leu Val Gly Gln Leu Asn Leu Gly Glu Val
                260                 265                 270 ggc act gtt tac att cca act gaa cag att gat cct aac tct ata cta    864
Gly Thr Val Tyr Ile Pro Thr Glu Gln Ile Asp Pro Asn Ser Ile Leu
                    275                 280                 285 cat gac aag tcc att caa aat ttc aca cct ttc aaa cta atg act cct    912
His Asp Lys Ser Ile Gln Asn Phe Thr Pro Phe Lys Leu Met Thr Pro
290                 295                 300 tta gat ggt atc acg gca gaa cgt att ggt tgt tta cag tgt ggt gag    960
Leu Asp Gly Ile Thr Ala Glu Arg Ile Gly Cys Leu Gln Cys Gly Glu
305                 310                 315                 320 aac ggt ggc ata aga tat tcc gta ttt tcg gga ctg agc ctg aat ctg   1008
Asn Gly Gly Ile Arg Tyr Ser Val Phe Ser Gly Leu Ser Leu Asn Leu
                325                 330                 335 ccg aac gag aat att ggt tcc act ctg aaa ctg tct cag ctg ctg agc   1056
Pro Asn Glu Asn Ile Gly Ser Thr Leu Lys Leu Ser Gln Leu Leu Ser
            340                 345                 350 gac tgg agt aaa cct gaa atc atc gaa ggc gta gaa tgt aac cgt tgt   1104
Asp Trp Ser Lys Pro Glu Ile Ile Glu Gly Val Glu Cys Asn Arg Cys
                355                 360                 365 gcc ctc aca gca gcg cac tct cat tta ttt ggt cag ttg aaa gaa ttt   1152
Ala Leu Thr Ala Ala His Ser His Leu Phe Gly Gln Leu Lys Glu Phe
370                 375                 380 gaa aaa aaa cct gag ggt tcg atc cca gaa aag cca att aac gct gta   1200
Glu Lys Lys Pro Glu Gly Ser Ile Pro Glu Lys Pro Ile Asn Ala Val
385                 390                 395                 400 aaa gat cgc gtc cat caa atc gaa gaa gtt ctt gcc aaa cca gtt att   1248
Lys Asp Arg Val His Gln Ile Glu Glu Val Leu Ala Lys Pro Val Ile
                405                 410                 415 gac gat gaa gat tat aag aag ttg cat aca gca aat atg gta cgt aaa   1296
Asp Asp Glu Asp Tyr Lys Lys Leu His Thr Ala Asn Met Val Arg Lys
            420                 425                 430 tgc tct aaa tct aag cag att tta ata tca aga cct cca cca ctg ctg   1344
Cys Ser Lys Ser Lys Gln Ile Leu Ile Ser Arg Pro Pro Pro Leu Leu
                435                 440                 445 tcc att cat atc aac cgt tcc gta ttt gat cca cgc acg tac atg att   1392
Ser Ile His Ile Asn Arg Ser Val Phe Asp Pro Arg Thr Tyr Met Ile
450                 455                 460 cgt aaa aat aac tcg aaa gta ttg ttt aag tca agg ttg aat ctt gcc   1440
Arg Lys Asn Asn Ser Lys Val Leu Phe Lys Ser Arg Leu Asn Leu Ala
465                 470                 475                 480 cca tgg tgt tgt gat att aat gaa atc aat ttg gat gct cgt ttg cca   1488
Pro Trp Cys Cys Asp Ile Asn Glu Ile Asn Leu Asp Ala Arg Leu Pro
```

-continued

```
                         485                 490                 495
atg tca aaa aag gaa aaa gct gcg caa caa gat tca agt gaa gat gaa    1536
Met Ser Lys Lys Glu Lys Ala Ala Gln Gln Asp Ser Ser Glu Asp Glu
        500                 505                 510 aac att ggc ggt gaa tac tat acg aaa tta cat gaa cgc ttc gag cag    1584
Asn Ile Gly Gly Glu Tyr Tyr Thr Lys Leu His Glu Arg Phe Glu Gln
            515                 520                 525 gaa ttt gaa gac agc gag gaa gaa aaa gaa tac gat gac gca gag ggg    1632
Glu Phe Glu Asp Ser Glu Glu Glu Lys Glu Tyr Asp Asp Ala Glu Gly
        530                 535                 540 aac tat gcg tct cat tac aat cat acc aag gat atc agt aac tat gat    1680
Asn Tyr Ala Ser His Tyr Asn His Thr Lys Asp Ile Ser Asn Tyr Asp
545                 550                 555                 560 ccc cta aac ggt gaa gtc gat ggc gtg aca tcc gat gat gaa gat gag    1728
Pro Leu Asn Gly Glu Val Asp Gly Val Thr Ser Asp Asp Glu Asp Glu
                565                 570                 575 tac att gaa gaa acc gat gct tta ggg aat aca atc aaa aaa cgt atc    1776
Tyr Ile Glu Glu Thr Asp Ala Leu Gly Asn Thr Ile Lys Lys Arg Ile
            580                 585                 590 ata gaa cat tct gat gtt gaa aac gag aat gta aaa gat aat gaa gaa    1824
Ile Glu His Ser Asp Val Glu Asn Glu Asn Val Lys Asp Asn Glu Glu
        595                 600                 605 ctg caa gaa atc gac aat gtg agc ctt gac gaa cca aag atc aat gtt    1872
Leu Gln Glu Ile Asp Asn Val Ser Leu Asp Glu Pro Lys Ile Asn Val
    610                 615                 620 gaa gat caa cta gaa aca tca tct gat gag gaa gat gtt ata cca gct    1920
Glu Asp Gln Leu Glu Thr Ser Ser Asp Glu Glu Asp Val Ile Pro Ala
625                 630                 635                 640 cca cct atc aat tat gct agg tca ttt tcc aca gtt cca gcc act cca    1968
Pro Pro Ile Asn Tyr Ala Arg Ser Phe Ser Thr Val Pro Ala Thr Pro
                645                 650                 655 ttg aca tat tca ttg cgc tct gtc att gtt cac tac ggt acc cat aat    2016
Leu Thr Tyr Ser Leu Arg Ser Val Ile Val His Tyr Gly Thr His Asn
            660                 665                 670 tat ggt cat tac att gca ttt cgt aaa tac cgt ggt tgt tgg tgg cgt    2064
Tyr Gly His Tyr Ile Ala Phe Arg Lys Tyr Arg Gly Cys Trp Trp Arg
        675                 680                 685 ata tct gat gag act gtg tac gtt gtg gac gaa gct gaa gtc ctt tca    2112
Ile Ser Asp Glu Thr Val Tyr Val Val Asp Glu Ala Glu Val Leu Ser
    690                 695                 700 aca ccc ggt gta ttt atg tta ttt tac gaa tat gac ttt gat gaa gaa    2160
Thr Pro Gly Val Phe Met Leu Phe Tyr Glu Tyr Asp Phe Asp Glu Glu
705                 710                 715                 720 act ggg aag atg aag gat gat ttg gaa gct att ctg agt aat aat gaa    2208
Thr Gly Lys Met Lys Asp Asp Leu Glu Ala Ile Leu Ser Asn Asn Glu
                725                 730                 735 gaa gat gat gaa aaa gag cag gag caa aaa gga gtc cag gag cca aag    2256
Glu Asp Asp Glu Lys Glu Gln Glu Gln Lys Gly Val Gln Glu Pro Lys
            740                 745                 750 gaa agc caa gag caa gga gaa ggt gaa gag caa gag gaa ggt caa gag    2304
Glu Ser Gln Glu Gln Gly Glu Gly Glu Glu Gln Glu Glu Gly Gln Glu
        755                 760                 765 cag atg aag ttc gag cgt aca gaa gac cat cgc gat att tct ggt aaa    2352
Gln Met Lys Phe Glu Arg Thr Glu Asp His Arg Asp Ile Ser Gly Lys
    770                 775                 780 gat gta aac gga tcc cat cat cac cat cac cat taa                    2388
Asp Val Asn Gly Ser His His His His His His
785                 790                 795
```

<210> SEQ ID NO 10

```
<211> LENGTH: 795
<212> TYPE: PRT
<213> ORGANISM: artificial sequence
<220> FEATURE:
<223> OTHER INFORMATION: UBI::UBP1deltaC2, based on yeast source

<400> SEQUENCE: 10
```

| | | | | | | | | | | | | | | |
|---|---|---|---|---|---|---|---|---|---|---|---|---|---|---|
|Met|Gln|Ile|Phe|Val|Lys|Thr|Leu|Thr|Gly|Lys|Thr|Ile|Thr|Leu|Glu|
|1| | | |5| | | |10| | | |15| | |

| | | | | | | | | | | | |
|---|---|---|---|---|---|---|---|---|---|---|---|
|Val|Glu|Ser|Ser|Asp|Thr|Ile|Asp|Asn|Val|Lys|Ser|Lys|Ile|Gln|Asp|
| | | |20| | | |25| | | |30| | | | |

|Lys|Glu|Gly|Ile|Pro|Pro|Asp|Gln|Gln|Arg|Leu|Ile|Phe|Ala|Gly|Lys|
| | | |35| | | |40| | | |45| | | | |

|Gln|Leu|Glu|Asp|Gly|Arg|Thr|Leu|Ser|Asp|Tyr|Asn|Ile|Gln|Lys|Glu|
| |50| | | |55| | | |60| | | | | | |

|Ser|Thr|Leu|His|Leu|Val|Leu|Arg|Leu|Arg|Gly|Gly|Phe|Ile|Ala|Gly|
|65| | | |70| | | |75| | | | | |80| |

|Leu|Val|Asn|Asp|Gly|Asn|Thr|Cys|Phe|Met|Asn|Ser|Val|Leu|Gln|Ser|
| | | | |85| | | |90| | | |95| | | |

|Leu|Ala|Ser|Ser|Arg|Glu|Leu|Met|Glu|Phe|Leu|Asp|Asn|Asn|Val|Ile|
| | | |100| | | |105| | | |110| | | | |

|Arg|Thr|Tyr|Glu|Glu|Ile|Glu|Gln|Asn|Glu|His|Asn|Glu|Glu|Gly|Asn|
| | | |115| | | |120| | | |125| | | | |

|Gly|Gln|Glu|Ser|Ala|Gln|Asp|Glu|Ala|Thr|His|Lys|Lys|Asn|Thr|Arg|
|130| | | | |135| | | |140| | | | | | |

|Lys|Gly|Gly|Lys|Val|Tyr|Gly|Lys|His|Lys|Lys|Leu|Asn|Arg|Lys|
|145| | | |150| | | |155| | | |160| | |

|Ser|Ser|Ser|Lys|Glu|Asp|Glu|Glu|Lys|Ser|Gln|Glu|Pro|Asp|Ile|Thr|
| | | |165| | | |170| | | |175| | | | |

|Phe|Ser|Val|Ala|Leu|Arg|Asp|Leu|Leu|Ser|Ala|Leu|Asn|Ala|Lys|Tyr|
| | | |180| | | |185| | | |190| | | | |

|Tyr|Arg|Asp|Lys|Pro|Tyr|Phe|Lys|Thr|Asn|Ser|Leu|Leu|Lys|Ala|Met|
| | |195| | | |200| | | |205| | | | | |

|Ser|Lys|Ser|Pro|Arg|Lys|Asn|Ile|Leu|Leu|Gly|Tyr|Asp|Gln|Glu|Asp|
| |210| | | |215| | | |220| | | | | | |

|Ala|Gln|Glu|Phe|Phe|Gln|Asn|Ile|Leu|Ala|Glu|Leu|Glu|Ser|Asn|Val|
|225| | | |230| | | |235| | | |240| | | |

|Lys|Ser|Leu|Asn|Thr|Glu|Lys|Leu|Asp|Thr|Thr|Pro|Val|Ala|Lys|Ser|
| | | |245| | | |250| | | |255| | | | |

|Glu|Leu|Pro|Asp|Asp|Ala|Leu|Val|Gly|Gln|Leu|Asn|Leu|Gly|Glu|Val|
| | |260| | | |265| | | |270| | | | | |

|Gly|Thr|Val|Tyr|Ile|Pro|Thr|Glu|Gln|Ile|Asp|Pro|Asn|Ser|Ile|Leu|
| | |275| | | |280| | | |285| | | | | |

|His|Asp|Lys|Ser|Ile|Gln|Asn|Phe|Thr|Pro|Phe|Lys|Leu|Met|Thr|Pro|
|290| | | | |295| | | |300| | | | | | |

|Leu|Asp|Gly|Ile|Thr|Ala|Glu|Arg|Ile|Gly|Cys|Leu|Gln|Cys|Gly|Glu|
|305| | | |310| | | |315| | | |320| | | |

|Asn|Gly|Gly|Ile|Arg|Tyr|Ser|Val|Phe|Ser|Gly|Leu|Ser|Leu|Asn|Leu|
| | | |325| | | |330| | | |335| | | | |

|Pro|Asn|Glu|Asn|Ile|Gly|Ser|Thr|Leu|Lys|Leu|Ser|Gln|Leu|Leu|Ser|
| | |340| | | |345| | | |350| | | | | |

|Asp|Trp|Ser|Lys|Pro|Glu|Ile|Ile|Glu|Gly|Val|Glu|Cys|Asn|Arg|Cys|
| | |355| | | |360| | | |365| | | | | |

|Ala|Leu|Thr|Ala|Ala|His|Ser|His|Leu|Phe|Gly|Gln|Leu|Lys|Glu|Phe|
|370| | | | |375| | | |380| | | | | | |

-continued

```
Glu Lys Lys Pro Glu Gly Ser Ile Pro Glu Lys Pro Ile Asn Ala Val
385                 390                 395                 400

Lys Asp Arg Val His Gln Ile Glu Glu Val Leu Ala Lys Pro Val Ile
            405                 410                 415

Asp Asp Glu Asp Tyr Lys Lys Leu His Thr Ala Asn Met Val Arg Lys
        420                 425                 430

Cys Ser Lys Ser Lys Gln Ile Leu Ile Ser Arg Pro Pro Leu Leu
    435                 440                 445

Ser Ile His Ile Asn Arg Ser Val Phe Asp Pro Arg Thr Tyr Met Ile
    450                 455                 460

Arg Lys Asn Asn Ser Lys Val Leu Phe Lys Ser Arg Leu Asn Leu Ala
465                 470                 475                 480

Pro Trp Cys Cys Asp Ile Asn Glu Ile Asn Leu Asp Ala Arg Leu Pro
                485                 490                 495

Met Ser Lys Lys Glu Lys Ala Ala Gln Gln Asp Ser Ser Glu Asp Glu
                500                 505                 510

Asn Ile Gly Gly Glu Tyr Tyr Thr Lys Leu His Glu Arg Phe Glu Gln
            515                 520                 525

Glu Phe Glu Asp Ser Glu Glu Lys Glu Tyr Asp Asp Ala Glu Gly
530                 535                 540

Asn Tyr Ala Ser His Tyr Asn His Thr Lys Asp Ile Ser Asn Tyr Asp
545                 550                 555                 560

Pro Leu Asn Gly Glu Val Asp Gly Val Thr Ser Asp Glu Asp Glu
                565                 570                 575

Tyr Ile Glu Glu Thr Asp Ala Leu Gly Asn Thr Ile Lys Lys Arg Ile
                580                 585                 590

Ile Glu His Ser Asp Val Glu Asn Glu Asn Val Lys Asp Asn Glu Glu
                595                 600                 605

Leu Gln Glu Ile Asp Asn Val Ser Leu Asp Glu Pro Lys Ile Asn Val
            610                 615                 620

Glu Asp Gln Leu Glu Thr Ser Ser Asp Glu Glu Asp Val Ile Pro Ala
625                 630                 635                 640

Pro Pro Ile Asn Tyr Ala Arg Ser Phe Ser Thr Val Pro Ala Thr Pro
                645                 650                 655

Leu Thr Tyr Ser Leu Arg Ser Val Ile Val His Tyr Gly Thr His Asn
                660                 665                 670

Tyr Gly His Tyr Ile Ala Phe Arg Lys Tyr Arg Gly Cys Trp Trp Arg
            675                 680                 685

Ile Ser Asp Glu Thr Val Tyr Val Asp Glu Ala Glu Val Leu Ser
                690                 695                 700

Thr Pro Gly Val Phe Met Leu Phe Tyr Glu Tyr Asp Phe Asp Glu Glu
705                 710                 715                 720

Thr Gly Lys Met Lys Asp Asp Leu Glu Ala Ile Leu Ser Asn Glu
            725                 730                 735

Glu Asp Asp Glu Lys Glu Gln Glu Gln Lys Gly Val Gln Glu Pro Lys
        740                 745                 750

Glu Ser Gln Glu Gln Gly Glu Gly Glu Gln Glu Glu Gly Gln Glu
    755                 760                 765

Gln Met Lys Phe Glu Arg Thr Glu Asp His Arg Asp Ile Ser Gly Lys
770                 775                 780

Asp Val Asn Gly Ser His His His His
785                 790                 795

<210> SEQ ID NO 11
```

<211> LENGTH: 2166
<212> TYPE: DNA
<213> ORGANISM: artificial sequence
<220> FEATURE:
<223> OTHER INFORMATION: UBP1delta2, based on yeast source
<220> FEATURE:
<221> NAME/KEY: CDS
<222> LOCATION: (1)..(2166)
<223> OTHER INFORMATION:

<400> SEQUENCE: 11

```
ggt ggt ttc att gct ggt tta gtt aat gat ggt aac act tgt ttt atg      48
Gly Gly Phe Ile Ala Gly Leu Val Asn Asp Gly Asn Thr Cys Phe Met
1               5                  10                  15 aac tct gtt ttg caa tca ttg gca tca tcc aga gaa tta atg gag ttc      96
Asn Ser Val Leu Gln Ser Leu Ala Ser Ser Arg Glu Leu Met Glu Phe
            20                  25                  30 ttg gac aat aat gtc ata agg acc tat gag gag ata gaa caa aat gaa     144
Leu Asp Asn Asn Val Ile Arg Thr Tyr Glu Glu Ile Glu Gln Asn Glu
        35                  40                  45 cac aat gaa gaa gga aac ggg caa gaa tct gct caa gat gaa gcc act     192
His Asn Glu Glu Gly Asn Gly Gln Glu Ser Ala Gln Asp Glu Ala Thr
    50                  55                  60 cat aag aaa aac act cgt aag ggt ggc aaa gtt tat ggt aag cat aag     240
His Lys Lys Asn Thr Arg Lys Gly Gly Lys Val Tyr Gly Lys His Lys
65                  70                  75                  80 aag aaa ttg aat agg aag tca agt tcg aaa gaa gac gaa gaa aag agc     288
Lys Lys Leu Asn Arg Lys Ser Ser Ser Lys Glu Asp Glu Glu Lys Ser
                85                  90                  95 cag gag cca gat atc act ttc agt gtc gcc tta agg gat cta ctt tct     336
Gln Glu Pro Asp Ile Thr Phe Ser Val Ala Leu Arg Asp Leu Leu Ser
            100                 105                 110 gcc tta aat gcg aag tat tat cgg gat aaa ccc tat ttc aaa acc aat     384
Ala Leu Asn Ala Lys Tyr Tyr Arg Asp Lys Pro Tyr Phe Lys Thr Asn
        115                 120                 125 agt tta ttg aaa gca atg tcc aaa tct cca aga aaa aat att ctt ctt     432
Ser Leu Leu Lys Ala Met Ser Lys Ser Pro Arg Lys Asn Ile Leu Leu
    130                 135                 140 ggc tac gac caa gag gac gcg caa gaa ttc ttc cag aac ata cta gcc     480
Gly Tyr Asp Gln Glu Asp Ala Gln Glu Phe Phe Gln Asn Ile Leu Ala
145                 150                 155                 160 gag ttg gaa agt aac gtt aaa tca ttg aat act gaa aaa cta gat acc     528
Glu Leu Glu Ser Asn Val Lys Ser Leu Asn Thr Glu Lys Leu Asp Thr
                165                 170                 175 act cca gtt gcg aaa tca gaa tta ccc gat gat gct tta gta ggt caa     576
Thr Pro Val Ala Lys Ser Glu Leu Pro Asp Asp Ala Leu Val Gly Gln
            180                 185                 190 ctt aac ctt ggt gaa gtt ggc act gtt tac att cca act gaa cag att     624
Leu Asn Leu Gly Glu Val Gly Thr Val Tyr Ile Pro Thr Glu Gln Ile
        195                 200                 205 gat cct aac tct ata cta cat gac aag tcc att caa aat ttc aca cct     672
Asp Pro Asn Ser Ile Leu His Asp Lys Ser Ile Gln Asn Phe Thr Pro
    210                 215                 220 ttc aaa cta atg act cct tta gat ggt atc acg gca gaa cgt att ggt     720
Phe Lys Leu Met Thr Pro Leu Asp Gly Ile Thr Ala Glu Arg Ile Gly
225                 230                 235                 240 tgt tta cag tgt ggt gag aac ggt ggc ata aga tat tcc gta ttt tcg     768
Cys Leu Gln Cys Gly Glu Asn Gly Gly Ile Arg Tyr Ser Val Phe Ser
                245                 250                 255 gga ctg agc ctg aat ctg ccg aac gag aat att ggt tcc act ctg aaa     816
Gly Leu Ser Leu Asn Leu Pro Asn Glu Asn Ile Gly Ser Thr Leu Lys
            260                 265                 270
```

| | |
|---|---|
| ctg tct cag ctg ctg agc gac tgg agt aaa cct gaa atc atc gaa ggc<br>Leu Ser Gln Leu Leu Ser Asp Trp Ser Lys Pro Glu Ile Ile Glu Gly<br>275 280 285 | 864 |
| gta gaa tgt aac cgt tgt gcc ctc aca gca gcg cac tct cat tta ttt<br>Val Glu Cys Asn Arg Cys Ala Leu Thr Ala Ala His Ser His Leu Phe<br>290 295 300 | 912 |
| ggt cag ttg aaa gaa ttt gaa aaa aaa cct gag ggt tcg atc cca gaa<br>Gly Gln Leu Lys Glu Phe Glu Lys Lys Pro Glu Gly Ser Ile Pro Glu<br>305 310 315 320 | 960 |
| aag cca att aac gct gta aaa gat cgc gtc cat caa atc gaa gaa gtt<br>Lys Pro Ile Asn Ala Val Lys Asp Arg Val His Gln Ile Glu Glu Val<br>325 330 335 | 1008 |
| ctt gcc aaa cca gtt att gac gat gaa gat tat aag aag ttg cat aca<br>Leu Ala Lys Pro Val Ile Asp Asp Glu Asp Tyr Lys Lys Leu His Thr<br>340 345 350 | 1056 |
| gca aat atg gta cgt aaa tgc tct aaa tct aag cag att tta ata tca<br>Ala Asn Met Val Arg Lys Cys Ser Lys Ser Lys Gln Ile Leu Ile Ser<br>355 360 365 | 1104 |
| aga cct cca cca ctg ctg tcc att cat atc aac cgt tcc gta ttt gat<br>Arg Pro Pro Pro Leu Leu Ser Ile His Ile Asn Arg Ser Val Phe Asp<br>370 375 380 | 1152 |
| cca cgc acg tac atg att cgt aaa aat aac tcg aaa gta ttg ttt aag<br>Pro Arg Thr Tyr Met Ile Arg Lys Asn Asn Ser Lys Val Leu Phe Lys<br>385 390 395 400 | 1200 |
| tca agg ttg aat ctt gcc cca tgg tgt tgt gat att aat gaa atc aat<br>Ser Arg Leu Asn Leu Ala Pro Trp Cys Cys Asp Ile Asn Glu Ile Asn<br>405 410 415 | 1248 |
| ttg gat gct cgt ttg cca atg tca aaa aag gaa aaa gct gcg caa caa<br>Leu Asp Ala Arg Leu Pro Met Ser Lys Lys Glu Lys Ala Ala Gln Gln<br>420 425 430 | 1296 |
| gat tca agt gaa gat gaa aac att ggc ggt gaa tac tat acg aaa tta<br>Asp Ser Ser Glu Asp Glu Asn Ile Gly Gly Glu Tyr Tyr Thr Lys Leu<br>435 440 445 | 1344 |
| cat gaa cgc ttc gag cag gaa ttt gaa gac agc gag gaa gaa aaa gaa<br>His Glu Arg Phe Glu Gln Glu Phe Glu Asp Ser Glu Glu Glu Lys Glu<br>450 455 460 | 1392 |
| tac gat gac gca gag ggg aac tat gcg tct cat tac aat cat acc aag<br>Tyr Asp Asp Ala Glu Gly Asn Tyr Ala Ser His Tyr Asn His Thr Lys<br>465 470 475 480 | 1440 |
| gat atc agt aac tat gat ccc cta aac ggt gaa gtc gat ggc gtg aca<br>Asp Ile Ser Asn Tyr Asp Pro Leu Asn Gly Glu Val Asp Gly Val Thr<br>485 490 495 | 1488 |
| tcc gat gat gaa gat gag tac att gaa gaa acc gat gct tta ggg aat<br>Ser Asp Asp Glu Asp Glu Tyr Ile Glu Glu Thr Asp Ala Leu Gly Asn<br>500 505 510 | 1536 |
| aca atc aaa aaa cgt atc ata gaa cat tct gat gtt gaa aac gag aat<br>Thr Ile Lys Lys Arg Ile Ile Glu His Ser Asp Val Glu Asn Glu Asn<br>515 520 525 | 1584 |
| gta aaa gat aat gaa gaa ctg caa gaa atc gac aat gtg agc ctt gac<br>Val Lys Asp Asn Glu Glu Leu Gln Glu Ile Asp Asn Val Ser Leu Asp<br>530 535 540 | 1632 |
| gaa cca aag atc aat gtt gaa gat caa cta gaa aca tca tct gat gag<br>Glu Pro Lys Ile Asn Val Glu Asp Gln Leu Glu Thr Ser Ser Asp Glu<br>545 550 555 560 | 1680 |
| gaa gat gtt ata cca gct cca cct atc aat tat gct agg tca ttt tcc<br>Glu Asp Val Ile Pro Ala Pro Pro Ile Asn Tyr Ala Arg Ser Phe Ser<br>565 570 575 | 1728 |
| aca gtt cca gcc act cca ttg aca tat tca ttg cgc tct gtc att gtt<br>Thr Val Pro Ala Thr Pro Leu Thr Tyr Ser Leu Arg Ser Val Ile Val<br>580 585 590 | 1776 |

```
cac tac ggt acc cat aat tat ggt cat tac att gca ttt cgt aaa tac    1824
His Tyr Gly Thr His Asn Tyr Gly His Tyr Ile Ala Phe Arg Lys Tyr
        595                 600                 605 cgt ggt tgt tgg tgg cgt ata tct gat gag act gtg tac gtt gtg gac    1872
Arg Gly Cys Trp Trp Arg Ile Ser Asp Glu Thr Val Tyr Val Val Asp
610                 615                 620 gaa gct gaa gtc ctt tca aca ccc ggt gta ttt atg tta ttt tac gaa    1920
Glu Ala Glu Val Leu Ser Thr Pro Gly Val Phe Met Leu Phe Tyr Glu
625                 630                 635                 640 tat gac ttt gat gaa gaa act ggg aag atg aag gat gat ttg gaa gct    1968
Tyr Asp Phe Asp Glu Glu Thr Gly Lys Met Lys Asp Asp Leu Glu Ala
                645                 650                 655 att cag agt aat aat gaa gaa gat gat gaa aaa gag cag gag caa aaa    2016
Ile Gln Ser Asn Asn Glu Glu Asp Asp Glu Lys Glu Gln Glu Gln Lys
            660                 665                 670 gga gtc cag gag cca aag gaa agc caa gag caa gga gaa ggt gaa gag    2064
Gly Val Gln Glu Pro Lys Glu Ser Gln Glu Gln Gly Glu Gly Glu Glu
        675                 680                 685 caa gag gaa ggt caa gag cag atg aag ttc gag cgt aca gaa gac cat    2112
Gln Glu Glu Gly Gln Glu Gln Met Lys Phe Glu Arg Thr Glu Asp His
690                 695                 700 cgc gat att tct ggt aaa gat gta aac gga tcc cat cat cac cat cac    2160
Arg Asp Ile Ser Gly Lys Asp Val Asn Gly Ser His His His His His
705                 710                 715                 720 cat taa                                                             2166
His

<210> SEQ ID NO 12
<211> LENGTH: 721
<212> TYPE: PRT
<213> ORGANISM: artificial sequence
<220> FEATURE:
<223> OTHER INFORMATION: UBP1delta2, based on yeast source

<400> SEQUENCE: 12

Gly Gly Phe Ile Ala Gly Leu Val Asn Asp Gly Asn Thr Cys Phe Met
1               5                   10                  15

Asn Ser Val Leu Gln Ser Leu Ala Ser Ser Arg Glu Leu Met Glu Phe
            20                  25                  30

Leu Asp Asn Asn Val Ile Arg Thr Tyr Glu Glu Ile Glu Gln Asn Glu
        35                  40                  45

His Asn Glu Glu Gly Asn Gly Gln Glu Ser Ala Gln Asp Glu Ala Thr
    50                  55                  60

His Lys Lys Asn Thr Arg Lys Gly Gly Lys Val Tyr Gly Lys His Lys
65                  70                  75                  80

Lys Lys Leu Asn Arg Lys Ser Ser Ser Lys Glu Asp Glu Glu Lys Ser
                85                  90                  95

Gln Glu Pro Asp Ile Thr Phe Ser Val Ala Leu Arg Asp Leu Leu Ser
            100                 105                 110

Ala Leu Asn Ala Lys Tyr Tyr Arg Asp Lys Pro Tyr Phe Lys Thr Asn
        115                 120                 125

Ser Leu Leu Lys Ala Met Ser Lys Ser Pro Arg Lys Asn Ile Leu Leu
    130                 135                 140

Gly Tyr Asp Gln Glu Asp Ala Gln Glu Phe Phe Gln Asn Ile Leu Ala
145                 150                 155                 160

Glu Leu Glu Ser Asn Val Lys Ser Leu Asn Thr Glu Lys Leu Asp Thr
                165                 170                 175

Thr Pro Val Ala Lys Ser Glu Leu Pro Asp Asp Ala Leu Val Gly Gln
            180                 185                 190
```

```
Leu Asn Leu Gly Glu Val Gly Thr Val Tyr Ile Pro Thr Glu Gln Ile
        195                 200                 205
Asp Pro Asn Ser Ile Leu His Asp Lys Ser Ile Gln Asn Phe Thr Pro
        210                 215                 220
Phe Lys Leu Met Thr Pro Leu Asp Gly Ile Thr Ala Glu Arg Ile Gly
225                 230                 235                 240
Cys Leu Gln Cys Gly Glu Asn Gly Gly Ile Arg Tyr Ser Val Phe Ser
                245                 250                 255
Gly Leu Ser Leu Asn Leu Pro Asn Glu Asn Ile Gly Ser Thr Leu Lys
                260                 265                 270
Leu Ser Gln Leu Leu Ser Asp Trp Ser Lys Pro Glu Ile Ile Glu Gly
            275                 280                 285
Val Glu Cys Asn Arg Cys Ala Leu Thr Ala Ala His Ser His Leu Phe
        290                 295                 300
Gly Gln Leu Lys Glu Phe Glu Lys Lys Pro Glu Gly Ser Ile Pro Glu
305                 310                 315                 320
Lys Pro Ile Asn Ala Val Lys Asp Arg Val His Gln Ile Glu Glu Val
                325                 330                 335
Leu Ala Lys Pro Val Ile Asp Asp Glu Asp Tyr Lys Lys Leu His Thr
                340                 345                 350
Ala Asn Met Val Arg Lys Cys Ser Lys Ser Lys Gln Ile Leu Ile Ser
            355                 360                 365
Arg Pro Pro Leu Leu Ser Ile His Ile Asn Arg Ser Val Phe Asp
        370                 375                 380
Pro Arg Thr Tyr Met Ile Arg Lys Asn Asn Ser Lys Val Leu Phe Lys
385                 390                 395                 400
Ser Arg Leu Asn Leu Ala Pro Trp Cys Cys Asp Ile Asn Glu Ile Asn
                405                 410                 415
Leu Asp Ala Arg Leu Pro Met Ser Lys Lys Glu Lys Ala Ala Gln Gln
                420                 425                 430
Asp Ser Ser Glu Asp Glu Asn Ile Gly Gly Glu Tyr Tyr Thr Lys Leu
        435                 440                 445
His Glu Arg Phe Glu Gln Glu Phe Glu Asp Ser Glu Glu Lys Glu
        450                 455                 460
Tyr Asp Asp Ala Glu Gly Asn Tyr Ala Ser His Tyr Asn His Thr Lys
465                 470                 475                 480
Asp Ile Ser Asn Tyr Asp Pro Leu Asn Gly Glu Val Asp Gly Val Thr
                485                 490                 495
Ser Asp Asp Glu Asp Glu Tyr Ile Glu Glu Thr Asp Ala Leu Gly Asn
                500                 505                 510
Thr Ile Lys Lys Arg Ile Ile Glu His Ser Asp Val Glu Asn Glu Asn
                515                 520                 525
Val Lys Asp Asn Glu Glu Leu Gln Glu Ile Asp Asn Val Ser Leu Asp
        530                 535                 540
Glu Pro Lys Ile Asn Val Glu Asp Gln Leu Glu Thr Ser Ser Asp Glu
545                 550                 555                 560
Glu Asp Val Ile Pro Ala Pro Pro Ile Asn Tyr Ala Arg Ser Phe Ser
                565                 570                 575
Thr Val Pro Ala Thr Pro Leu Thr Tyr Ser Leu Arg Ser Val Ile Val
                580                 585                 590
His Tyr Gly Thr His Asn Tyr Gly His Tyr Ile Ala Phe Arg Lys Tyr
            595                 600                 605
Arg Gly Cys Trp Trp Arg Ile Ser Asp Glu Thr Val Tyr Val Val Asp
```

-continued

```
                  610                 615                 620
Glu Ala Glu Val Leu Ser Thr Pro Gly Val Phe Met Leu Phe Tyr Glu
625                 630                 635                 640

Tyr Asp Phe Asp Glu Glu Thr Gly Lys Met Lys Asp Asp Leu Glu Ala
                    645                 650                 655

Ile Gln Ser Asn Asn Glu Glu Asp Glu Lys Glu Gln Glu Gln Lys
                660                 665                 670

Gly Val Gln Glu Pro Lys Glu Ser Gln Glu Gln Gly Gly Glu Glu
                    675                 680                 685

Gln Glu Glu Gly Gln Gln Met Lys Phe Glu Arg Thr Glu Asp His
                690                 695                 700

Arg Asp Ile Ser Gly Lys Asp Val Asn Gly Ser His His His His
705                 710                 715                 720

His

<210> SEQ ID NO 13
<211> LENGTH: 2298
<212> TYPE: DNA
<213> ORGANISM: artificial sequence
<220> FEATURE:
<223> OTHER INFORMATION: UBP1delta, based on yeast source
<220> FEATURE:
<221> NAME/KEY: CDS
<222> LOCATION: (1)..(2298)
<223> OTHER INFORMATION:

<400> SEQUENCE: 13 ggt ggt gac cat cta aac tac att gtt gag agc gtt agt gaa atg aca        48
Gly Gly Asp His Leu Asn Tyr Ile Val Glu Ser Val Ser Glu Met Thr
1               5                   10                  15 aca aac ttc aga aat aat aat agc ctt agc cgt tgg ttg ccc aga agt       96
Thr Asn Phe Arg Asn Asn Asn Ser Leu Ser Arg Trp Leu Pro Arg Ser
            20                  25                  30 aag ttt acc cac tta gac gaa gag atc ttg aaa cgt ggt ggt ttc att      144
Lys Phe Thr His Leu Asp Glu Glu Ile Leu Lys Arg Gly Gly Phe Ile
        35                  40                  45 gct ggt tta gtt aat gat ggt aac act tgt ttt atg aac tct gtt ttg      192
Ala Gly Leu Val Asn Asp Gly Asn Thr Cys Phe Met Asn Ser Val Leu
50                  55                  60 caa tca ttg gca tca tcc aga gaa tta atg gag ttc ttg gac aat aat      240
Gln Ser Leu Ala Ser Ser Arg Glu Leu Met Glu Phe Leu Asp Asn Asn
65                  70                  75                  80 gtc ata agg acc tat gag gag ata gaa caa aat gaa cac aat gaa gaa      288
Val Ile Arg Thr Tyr Glu Glu Ile Glu Gln Asn Glu His Asn Glu Glu
                85                  90                  95 gga aac ggg caa gaa tct gct caa gat gaa gcc act cat aag aaa aac      336
Gly Asn Gly Gln Glu Ser Ala Gln Asp Glu Ala Thr His Lys Lys Asn
            100                 105                 110 act cgt aag ggt ggc aaa gtt tat ggt aag cat aag aag aaa ttg aat      384
Thr Arg Lys Gly Gly Lys Val Tyr Gly Lys His Lys Lys Lys Leu Asn
        115                 120                 125 agg aag tca agt tcg aaa gaa gac gaa gaa aag agc cag gag cca gat      432
Arg Lys Ser Ser Ser Lys Glu Asp Glu Glu Lys Ser Gln Glu Pro Asp
    130                 135                 140 atc act ttc agt gtc gcc tta agg gat cta ctt tct gcc tta aat gcg      480
Ile Thr Phe Ser Val Ala Leu Arg Asp Leu Leu Ser Ala Leu Asn Ala
145                 150                 155                 160 aag tat tat cgg gat aaa ccc tat ttc aaa acc aat agt tta ttg aaa      528
Lys Tyr Tyr Arg Asp Lys Pro Tyr Phe Lys Thr Asn Ser Leu Leu Lys
                165                 170                 175
```

```
gca atg tcc aaa tct cca aga aaa aat att ctt ctt ggc tac gac caa    576
Ala Met Ser Lys Ser Pro Arg Lys Asn Ile Leu Leu Gly Tyr Asp Gln
        180                 185                 190 gag gac gcg caa gaa ttc ttc cag aac ata cta gcc gag ttg gaa agt    624
Glu Asp Ala Gln Glu Phe Phe Gln Asn Ile Leu Ala Glu Leu Glu Ser
    195                 200                 205 aac gtt aaa tca ttg aat act gaa aaa cta gat acc act cca gtt gcg    672
Asn Val Lys Ser Leu Asn Thr Glu Lys Leu Asp Thr Thr Pro Val Ala
210                 215                 220 aaa tca gaa tta ccc gat gat gct tta gta ggt caa ctt aac ctt ggt    720
Lys Ser Glu Leu Pro Asp Asp Ala Leu Val Gly Gln Leu Asn Leu Gly
225                 230                 235                 240 gaa gtt ggc act gtt tac att cca act gaa cag att gat cct aac tct    768
Glu Val Gly Thr Val Tyr Ile Pro Thr Glu Gln Ile Asp Pro Asn Ser
                245                 250                 255 ata cta cat gac aag tcc att caa aat ttc aca cct ttc aaa cta atg    816
Ile Leu His Asp Lys Ser Ile Gln Asn Phe Thr Pro Phe Lys Leu Met
            260                 265                 270 act cct tta gat ggt atc acg gca gaa cgt att ggt tgt tta cag tgt    864
Thr Pro Leu Asp Gly Ile Thr Ala Glu Arg Ile Gly Cys Leu Gln Cys
        275                 280                 285 ggt gag aac ggt ggc ata aga tat tcc gta ttt tcg gga ctg agc ctg    912
Gly Glu Asn Gly Gly Ile Arg Tyr Ser Val Phe Ser Gly Leu Ser Leu
    290                 295                 300 aat ctg ccg aac gag aat att ggt tcc act ctg aaa ctg tct cag ctg    960
Asn Leu Pro Asn Glu Asn Ile Gly Ser Thr Leu Lys Leu Ser Gln Leu
305                 310                 315                 320 ctg agc gac tgg agt aaa cct gaa atc atc gaa ggc gta gaa tgt aac   1008
Leu Ser Asp Trp Ser Lys Pro Glu Ile Ile Glu Gly Val Glu Cys Asn
                325                 330                 335 cgt tgt gcc ctc aca gca gcg cac tct cat tta ttt ggt cag ttg aaa   1056
Arg Cys Ala Leu Thr Ala Ala His Ser His Leu Phe Gly Gln Leu Lys
            340                 345                 350 gaa ttt gaa aaa aaa cct gag ggt tcg atc cca gaa aag cca att aac   1104
Glu Phe Glu Lys Lys Pro Glu Gly Ser Ile Pro Glu Lys Pro Ile Asn
        355                 360                 365 gct gta aaa gat cgc gtc cat caa atc gaa gaa gtt ctt gcc aaa cca   1152
Ala Val Lys Asp Arg Val His Gln Ile Glu Glu Val Leu Ala Lys Pro
    370                 375                 380 gtt att gac gat gaa gat tat aag aag ttg cat aca gca aat atg gta   1200
Val Ile Asp Asp Glu Asp Tyr Lys Lys Leu His Thr Ala Asn Met Val
385                 390                 395                 400 cgt aaa tgc tct aaa tct aag cag att tta ata tca aga cct cca cca   1248
Arg Lys Cys Ser Lys Ser Lys Gln Ile Leu Ile Ser Arg Pro Pro Pro
                405                 410                 415 ctg ctg tcc att cat atc aac cgt tcc gta ttt gat cca cgc acg tac   1296
Leu Leu Ser Ile His Ile Asn Arg Ser Val Phe Asp Pro Arg Thr Tyr
            420                 425                 430 atg att cgt aaa aat aac tcg aaa gta ttg ttt aag tca agg ttg aat   1344
Met Ile Arg Lys Asn Asn Ser Lys Val Leu Phe Lys Ser Arg Leu Asn
        435                 440                 445 ctt gcc cca tgg tgt tgt gat att aat gaa atc aat ttg gat gct cgt   1392
Leu Ala Pro Trp Cys Cys Asp Ile Asn Glu Ile Asn Leu Asp Ala Arg
    450                 455                 460 ttg cca atg tca aaa aag gaa aaa gct gcg caa caa gat tca agt gaa   1440
Leu Pro Met Ser Lys Lys Glu Lys Ala Ala Gln Gln Asp Ser Ser Glu
465                 470                 475                 480 gat gaa aac att ggc ggt gaa tac tat acg aaa tta cat gaa cgc ttc   1488
Asp Glu Asn Ile Gly Gly Glu Tyr Tyr Thr Lys Leu His Glu Arg Phe
                485                 490                 495
```

```
gag cag gaa ttt gaa gac agc gag gaa gaa aaa gaa tac gat gac gca   1536
Glu Gln Glu Phe Glu Asp Ser Glu Glu Glu Lys Glu Tyr Asp Asp Ala
            500                 505                 510 gag ggg aac tat gcg tct cat tac aat cat acc aag gat atc agt aac   1584
Glu Gly Asn Tyr Ala Ser His Tyr Asn His Thr Lys Asp Ile Ser Asn
        515                 520                 525 tat gat ccc cta aac ggt gaa gtc gat ggc gtg aca tcc gat gat gaa   1632
Tyr Asp Pro Leu Asn Gly Glu Val Asp Gly Val Thr Ser Asp Asp Glu
    530                 535                 540 gat gag tac att gaa gaa acc gat gct tta ggg aat aca atc aaa aaa   1680
Asp Glu Tyr Ile Glu Glu Thr Asp Ala Leu Gly Asn Thr Ile Lys Lys
545                 550                 555                 560 cgt atc ata gaa cat tct gat gtt gaa aac gag aat gta aaa gat aat   1728
Arg Ile Ile Glu His Ser Asp Val Glu Asn Glu Asn Val Lys Asp Asn
                565                 570                 575 gaa gaa ctg caa gaa atc gac aat gtg agc ctt gac gaa cca aag atc   1776
Glu Glu Leu Gln Glu Ile Asp Asn Val Ser Leu Asp Glu Pro Lys Ile
            580                 585                 590 aat gtt gaa gat caa cta gaa aca tca tct gat gag gaa gat gtt ata   1824
Asn Val Glu Asp Gln Leu Glu Thr Ser Ser Asp Glu Glu Asp Val Ile
        595                 600                 605 cca gct cca cct atc aat tat gct agg tca ttt tcc aca gtt cca gcc   1872
Pro Ala Pro Pro Ile Asn Tyr Ala Arg Ser Phe Ser Thr Val Pro Ala
    610                 615                 620 act cca ttg aca tat tca ttg cgc tct gtc att gtt cac tac ggt acc   1920
Thr Pro Leu Thr Tyr Ser Leu Arg Ser Val Ile Val His Tyr Gly Thr
625                 630                 635                 640 cat aat tat ggt cat tac att gca ttt cgt aaa tac cgt ggt tgt tgg   1968
His Asn Tyr Gly His Tyr Ile Ala Phe Arg Lys Tyr Arg Gly Cys Trp
                645                 650                 655 tgg cgt ata tct gat gag act gtg tac gtt gtg gac gaa gct gaa gtc   2016
Trp Arg Ile Ser Asp Glu Thr Val Tyr Val Val Asp Glu Ala Glu Val
            660                 665                 670 ctt tca aca ccc ggt gta ttt atg tta ttt tac gaa tat gac ttt gat   2064
Leu Ser Thr Pro Gly Val Phe Met Leu Phe Tyr Glu Tyr Asp Phe Asp
        675                 680                 685 gaa gaa act ggg aag atg aag gat gat ttg gaa gct att cag agt aat   2112
Glu Glu Thr Gly Lys Met Lys Asp Asp Leu Glu Ala Ile Gln Ser Asn
    690                 695                 700 aat gaa gaa gat gat gaa aaa gag cag gag caa aaa gga gtc cag gag   2160
Asn Glu Glu Asp Asp Glu Lys Glu Gln Glu Gln Lys Gly Val Gln Glu
705                 710                 715                 720 cca aag gaa agc caa gag caa gga gaa ggt gaa gag caa gag gaa ggt   2208
Pro Lys Glu Ser Gln Glu Gln Gly Glu Gly Glu Glu Gln Glu Glu Gly
                725                 730                 735 caa gag cag atg aag ttc gag cgt aca gaa gac cat cgc gat att tct   2256
Gln Glu Gln Met Lys Phe Glu Arg Thr Glu Asp His Arg Asp Ile Ser
            740                 745                 750 ggt aaa gat gta aac gga tcc cat cat cac cat cac cat taa           2298
Gly Lys Asp Val Asn Gly Ser His His His His His His
        755                 760                 765

<210> SEQ ID NO 14
<211> LENGTH: 765
<212> TYPE: PRT
<213> ORGANISM: artificial sequence
<220> FEATURE:
<223> OTHER INFORMATION: UBP1delta, based on yeast source

<400> SEQUENCE: 14

Gly Gly Asp His Leu Asn Tyr Ile Val Glu Ser Val Ser Glu Met Thr
1               5                   10                  15
```

-continued

```
Thr Asn Phe Arg Asn Asn Asn Ser Leu Ser Arg Trp Leu Pro Arg Ser
             20                  25                  30

Lys Phe Thr His Leu Asp Glu Glu Ile Leu Lys Arg Gly Gly Phe Ile
         35                  40                  45

Ala Gly Leu Val Asn Asp Gly Asn Thr Cys Phe Met Asn Ser Val Leu
 50                  55                  60

Gln Ser Leu Ala Ser Ser Arg Glu Leu Met Glu Phe Leu Asp Asn Asn
 65                  70                  75                  80

Val Ile Arg Thr Tyr Glu Glu Ile Glu Gln Asn Glu His Asn Glu Glu
             85                  90                  95

Gly Asn Gly Gln Glu Ser Ala Gln Asp Glu Ala Thr His Lys Lys Asn
         100                 105                 110

Thr Arg Lys Gly Gly Lys Val Tyr Gly Lys His Lys Lys Lys Leu Asn
         115                 120                 125

Arg Lys Ser Ser Lys Glu Asp Glu Glu Lys Ser Gln Glu Pro Asp
130                 135                 140

Ile Thr Phe Ser Val Ala Leu Arg Asp Leu Leu Ser Ala Leu Asn Ala
145                 150                 155                 160

Lys Tyr Tyr Arg Asp Lys Pro Tyr Phe Lys Thr Asn Ser Leu Leu Lys
                 165                 170                 175

Ala Met Ser Lys Ser Pro Arg Lys Asn Ile Leu Leu Gly Tyr Asp Gln
             180                 185                 190

Glu Asp Ala Gln Glu Phe Phe Gln Asn Ile Leu Ala Glu Leu Glu Ser
         195                 200                 205

Asn Val Lys Ser Leu Asn Thr Glu Lys Leu Asp Thr Thr Pro Val Ala
210                 215                 220

Lys Ser Glu Leu Pro Asp Asp Ala Leu Val Gly Gln Leu Asn Leu Gly
225                 230                 235                 240

Glu Val Gly Thr Val Tyr Ile Pro Thr Glu Gln Ile Asp Pro Asn Ser
             245                 250                 255

Ile Leu His Asp Lys Ser Ile Gln Asn Phe Thr Pro Phe Lys Leu Met
             260                 265                 270

Thr Pro Leu Asp Gly Ile Thr Ala Glu Arg Ile Gly Cys Leu Gln Cys
         275                 280                 285

Gly Glu Asn Gly Gly Ile Arg Tyr Ser Val Phe Ser Gly Leu Ser Leu
290                 295                 300

Asn Leu Pro Asn Glu Asn Ile Gly Ser Thr Leu Lys Leu Ser Gln Leu
305                 310                 315                 320

Leu Ser Asp Trp Ser Lys Pro Glu Ile Ile Glu Gly Val Glu Cys Asn
                 325                 330                 335

Arg Cys Ala Leu Thr Ala Ala His Ser His Leu Phe Gly Gln Leu Lys
             340                 345                 350

Glu Phe Glu Lys Lys Pro Glu Gly Ser Ile Pro Glu Lys Pro Ile Asn
         355                 360                 365

Ala Val Lys Asp Arg Val His Gln Ile Glu Glu Val Leu Ala Lys Pro
370                 375                 380

Val Ile Asp Asp Glu Asp Tyr Lys Lys Leu His Thr Ala Asn Met Val
385                 390                 395                 400

Arg Lys Cys Ser Lys Ser Lys Gln Ile Leu Ile Ser Arg Pro Pro
             405                 410                 415

Leu Leu Ser Ile His Ile Asn Arg Ser Val Phe Asp Pro Arg Thr Tyr
             420                 425                 430

Met Ile Arg Lys Asn Asn Ser Lys Val Leu Phe Lys Ser Arg Leu Asn
```

```
                  435                 440                 445
Leu Ala Pro Trp Cys Cys Asp Ile Asn Glu Ile Asn Leu Asp Ala Arg
450                 455                 460
Leu Pro Met Ser Lys Lys Glu Lys Ala Ala Gln Gln Asp Ser Ser Glu
465                 470                 475                 480
Asp Glu Asn Ile Gly Gly Glu Tyr Tyr Thr Lys Leu His Glu Arg Phe
                    485                 490                 495
Glu Gln Glu Phe Glu Asp Ser Glu Glu Lys Glu Tyr Asp Asp Ala
                500                 505                 510
Glu Gly Asn Tyr Ala Ser His Tyr Asn His Thr Lys Asp Ile Ser Asn
                515                 520                 525
Tyr Asp Pro Leu Asn Gly Glu Val Asp Gly Val Thr Ser Asp Asp Glu
530                 535                 540
Asp Glu Tyr Ile Glu Glu Thr Asp Ala Leu Gly Asn Thr Ile Lys Lys
545                 550                 555                 560
Arg Ile Ile Glu His Ser Asp Val Glu Asn Asn Val Lys Asp Asn
                565                 570                 575
Glu Glu Leu Gln Glu Ile Asp Asn Val Ser Leu Asp Glu Pro Lys Ile
                580                 585                 590
Asn Val Glu Asp Gln Leu Glu Thr Ser Ser Asp Glu Asp Val Ile
                595                 600                 605
Pro Ala Pro Pro Ile Asn Tyr Ala Arg Ser Phe Ser Thr Val Pro Ala
610                 615                 620
Thr Pro Leu Thr Tyr Ser Leu Arg Ser Val Ile Val His Tyr Gly Thr
625                 630                 635                 640
His Asn Tyr Gly His Tyr Ile Ala Phe Arg Lys Tyr Arg Gly Cys Trp
                645                 650                 655
Trp Arg Ile Ser Asp Glu Thr Val Tyr Val Asp Glu Ala Glu Val
                660                 665                 670
Leu Ser Thr Pro Gly Val Phe Met Leu Phe Tyr Glu Tyr Asp Phe Asp
                675                 680                 685
Glu Glu Thr Gly Lys Met Lys Asp Asp Leu Glu Ala Ile Gln Ser Asn
690                 695                 700
Asn Glu Glu Asp Asp Glu Lys Glu Gln Glu Gln Lys Gly Val Gln Glu
705                 710                 715                 720
Pro Lys Glu Ser Gln Glu Gly Gly Glu Glu Gln Glu Gly
                    725                 730                 735
Gln Glu Gln Met Lys Phe Glu Arg Thr Glu Asp His Arg Asp Ile Ser
                740                 745                 750
Gly Lys Asp Val Asn Gly Ser His His His His His
            755                 760                 765

<210> SEQ ID NO 15
<211> LENGTH: 2298
<212> TYPE: DNA
<213> ORGANISM: artificial sequence
<220> FEATURE:
<223> OTHER INFORMATION: UBP1deltaC , based on yeast source
<220> FEATURE:
<221> NAME/KEY: CDS
<222> LOCATION: (1)..(2298)
<223> OTHER INFORMATION:

<400> SEQUENCE: 15 ggt ggt gac cat cta aac tac att gtt gag agc gtt agt gaa atg aca    48
Gly Gly Asp His Leu Asn Tyr Ile Val Glu Ser Val Ser Glu Met Thr
1               5                   10                  15
```

| | |
|---|---|
| aca aac ttc aga aat aat aat agc ctt agc cgt tgg ttg ccc aga agt<br>Thr Asn Phe Arg Asn Asn Asn Ser Leu Ser Arg Trp Leu Pro Arg Ser<br>20                        25                 30 | 96 |
| aag ttt acc cac tta gac gaa gag atc ttg aaa cgt ggt ggt ttc att<br>Lys Phe Thr His Leu Asp Glu Glu Ile Leu Lys Arg Gly Gly Phe Ile<br>          35                 40                 45 | 144 |
| gct ggt tta gtt aat gat ggt aac act tgt ttt atg aac tct gtt ttg<br>Ala Gly Leu Val Asn Asp Gly Asn Thr Cys Phe Met Asn Ser Val Leu<br>50                        55                 60 | 192 |
| caa tca ttg gca tca tcc aga gaa tta atg gag ttc ttg gac aat aat<br>Gln Ser Leu Ala Ser Ser Arg Glu Leu Met Glu Phe Leu Asp Asn Asn<br>65                        70               75                 80 | 240 |
| gtc ata agg acc tat gag gag ata gaa caa aat gaa cac aat gaa gaa<br>Val Ile Arg Thr Tyr Glu Glu Ile Glu Gln Asn Glu His Asn Glu Glu<br>                 85                 90                 95 | 288 |
| gga aac ggg caa gaa tct gct caa gat gaa gcc act cat aag aaa aac<br>Gly Asn Gly Gln Glu Ser Ala Gln Asp Glu Ala Thr His Lys Lys Asn<br>                100              105             110 | 336 |
| act cgt aag ggt ggc aaa gtt tat ggt aag cat aag aag aaa ttg aat<br>Thr Arg Lys Gly Gly Lys Val Tyr Gly Lys His Lys Lys Lys Leu Asn<br>          115               120              125 | 384 |
| agg aag tca agt tcg aaa gaa gac gaa gaa aag agc cag gag cca gat<br>Arg Lys Ser Ser Ser Lys Glu Asp Glu Glu Lys Ser Gln Glu Pro Asp<br>130                     135              140 | 432 |
| atc act ttc agt gtc gcc tta agg gat cta ctt tct gcc tta aat gcg<br>Ile Thr Phe Ser Val Ala Leu Arg Asp Leu Leu Ser Ala Leu Asn Ala<br>145                     150              155               160 | 480 |
| aag tat tat cgg gat aaa ccc tat ttc aaa acc aat agt tta ttg aaa<br>Lys Tyr Tyr Arg Asp Lys Pro Tyr Phe Lys Thr Asn Ser Leu Leu Lys<br>                 165              170              175 | 528 |
| gca atg tcc aaa tct cca aga aaa aat att ctt ctt ggc tac gac caa<br>Ala Met Ser Lys Ser Pro Arg Lys Asn Ile Leu Leu Gly Tyr Asp Gln<br>          180               185              190 | 576 |
| gag gac gcg caa gaa ttc ttc cag aac ata cta gcc gag ttg gaa agt<br>Glu Asp Ala Gln Glu Phe Phe Gln Asn Ile Leu Ala Glu Leu Glu Ser<br>195                     200              205 | 624 |
| aac gtt aaa tca ttg aat act gaa aaa cta gat acc act cca gtt gcg<br>Asn Val Lys Ser Leu Asn Thr Glu Lys Leu Asp Thr Thr Pro Val Ala<br>210                     215              220 | 672 |
| aaa tca gaa tta ccc gat gat gct tta gta ggt caa ctt aac ctt ggt<br>Lys Ser Glu Leu Pro Asp Asp Ala Leu Val Gly Gln Leu Asn Leu Gly<br>225                     230              235               240 | 720 |
| gaa gtt ggc act gtt tac att cca act gaa cag att gat cct aac tct<br>Glu Val Gly Thr Val Tyr Ile Pro Thr Glu Gln Ile Asp Pro Asn Ser<br>                 245              250              255 | 768 |
| ata cta cat gac aag tcc att caa aat ttc aca cct ttc aaa cta atg<br>Ile Leu His Asp Lys Ser Ile Gln Asn Phe Thr Pro Phe Lys Leu Met<br>          260               265              270 | 816 |
| act cct tta gat ggt atc acg gca gaa cgt att ggt tgt tta cag tgt<br>Thr Pro Leu Asp Gly Ile Thr Ala Glu Arg Ile Gly Cys Leu Gln Cys<br>275                     280              285 | 864 |
| ggt gag aac ggt ggc ata aga tat tcc gta ttt tcg gga ctg agc ctg<br>Gly Glu Asn Gly Gly Ile Arg Tyr Ser Val Phe Ser Gly Leu Ser Leu<br>290                     295              300 | 912 |
| aat ctg ccg aac gag aat att ggt tcc act ctg aaa ctg tct cag ctg<br>Asn Leu Pro Asn Glu Asn Ile Gly Ser Thr Leu Lys Leu Ser Gln Leu<br>305                     310              315               320 | 960 |
| ctg agc gac tgg agt aaa cct gaa atc atc gaa ggc gta gaa tgt aac<br>Leu Ser Asp Trp Ser Lys Pro Glu Ile Ile Glu Gly Val Glu Cys Asn<br>                 325              330              335 | 1008 |

```
cgt tgt gcc ctc aca gca gcg cac tct cat tta ttt ggt cag ttg aaa    1056
Arg Cys Ala Leu Thr Ala Ala His Ser His Leu Phe Gly Gln Leu Lys
            340                 345                 350 gaa ttt gaa aaa aaa cct gag ggt tcg atc cca gaa aag cca att aac    1104
Glu Phe Glu Lys Lys Pro Glu Gly Ser Ile Pro Glu Lys Pro Ile Asn
355                 360                 365 gct gta aaa gat cgc gtc cat caa atc gaa gaa gtt ctt gcc aaa cca    1152
Ala Val Lys Asp Arg Val His Gln Ile Glu Glu Val Leu Ala Lys Pro
    370                 375                 380 gtt att gac gat gaa gat tat aag aag ttg cat aca gca aat atg gta    1200
Val Ile Asp Asp Glu Asp Tyr Lys Lys Leu His Thr Ala Asn Met Val
385                 390                 395                 400 cgt aaa tgc tct aaa tct aag cag att tta ata tca aga cct cca cca    1248
Arg Lys Cys Ser Lys Ser Lys Gln Ile Leu Ile Ser Arg Pro Pro Pro
                405                 410                 415 ctg ctg tcc att cat atc aac cgt tcc gta ttt gat cca cgc acg tac    1296
Leu Leu Ser Ile His Ile Asn Arg Ser Val Phe Asp Pro Arg Thr Tyr
            420                 425                 430 atg att cgt aaa aat aac tcg aaa gta ttg ttt aag tca agg ttg aat    1344
Met Ile Arg Lys Asn Asn Ser Lys Val Leu Phe Lys Ser Arg Leu Asn
        435                 440                 445 ctt gcc cca tgg tgt tgt gat att aat gaa atc aat ttg gat gct cgt    1392
Leu Ala Pro Trp Cys Cys Asp Ile Asn Glu Ile Asn Leu Asp Ala Arg
    450                 455                 460 ttg cca atg tca aaa aag gaa aaa gct gcg caa caa gat tca agt gaa    1440
Leu Pro Met Ser Lys Lys Glu Lys Ala Ala Gln Gln Asp Ser Ser Glu
465                 470                 475                 480 gat gaa aac att ggc ggt gaa tac tat acg aaa tta cat gaa cgc ttc    1488
Asp Glu Asn Ile Gly Gly Glu Tyr Tyr Thr Lys Leu His Glu Arg Phe
                485                 490                 495 gag cag gaa ttt gaa gac agc gag gaa gaa aaa gaa tac gat gac gca    1536
Glu Gln Glu Phe Glu Asp Ser Glu Glu Glu Lys Glu Tyr Asp Asp Ala
            500                 505                 510 gag ggg aac tat gcg tct cat tac aat cat acc aag gat atc agt aac    1584
Glu Gly Asn Tyr Ala Ser His Tyr Asn His Thr Lys Asp Ile Ser Asn
        515                 520                 525 tat gat ccc cta aac ggt gaa gtc gat ggc gtg aca tcc gat gat gaa    1632
Tyr Asp Pro Leu Asn Gly Glu Val Asp Gly Val Thr Ser Asp Asp Glu
    530                 535                 540 gat gag tac att gaa gaa acc gat gct tta ggg aat aca atc aaa aaa    1680
Asp Glu Tyr Ile Glu Glu Thr Asp Ala Leu Gly Asn Thr Ile Lys Lys
545                 550                 555                 560 cgt atc ata gaa cat tct gat gtt gaa aac gag aat gta aaa gat aat    1728
Arg Ile Ile Glu His Ser Asp Val Glu Asn Glu Asn Val Lys Asp Asn
                565                 570                 575 gaa gaa ctg caa gaa atc gac aat gtg agc ctt gac gaa cca aag atc    1776
Glu Glu Leu Gln Glu Ile Asp Asn Val Ser Leu Asp Glu Pro Lys Ile
            580                 585                 590 aat gtt gaa gat caa cta gaa aca tca tct gat gag gaa gat gtt ata    1824
Asn Val Glu Asp Gln Leu Glu Thr Ser Ser Asp Glu Glu Asp Val Ile
        595                 600                 605 cca gct cca cct atc aat tat gct agg tca ttt tcc aca gtt cca gcc    1872
Pro Ala Pro Pro Ile Asn Tyr Ala Arg Ser Phe Ser Thr Val Pro Ala
    610                 615                 620 act cca ttg aca tat tca ttg cgc tct gtc att gtt cac tac ggt acc    1920
Thr Pro Leu Thr Tyr Ser Leu Arg Ser Val Ile Val His Tyr Gly Thr
625                 630                 635                 640 cat aat tat ggt cat tac att gca ttt cgt aaa tac cgt ggt tgt tgg    1968
His Asn Tyr Gly His Tyr Ile Ala Phe Arg Lys Tyr Arg Gly Cys Trp
                645                 650                 655
```

```
tgg cgt ata tct gat gag act gtg tac gtt gtg gac gaa gct gaa gtc   2016
Trp Arg Ile Ser Asp Glu Thr Val Tyr Val Val Asp Glu Ala Glu Val
            660                 665                 670 ctt tca aca ccc ggt gta ttt atg tta ttt tac gaa tat gac ttt gat   2064
Leu Ser Thr Pro Gly Val Phe Met Leu Phe Tyr Glu Tyr Asp Phe Asp
        675                 680                 685 gaa gaa act ggg aag atg aag gat gat ttg gaa gct att ctg agt aat   2112
Glu Glu Thr Gly Lys Met Lys Asp Asp Leu Glu Ala Ile Leu Ser Asn
690                 695                 700 aat gaa gaa gat gat gaa aaa gag cag gag caa aaa gga gtc cag gag   2160
Asn Glu Glu Asp Asp Glu Lys Glu Gln Glu Gln Lys Gly Val Gln Glu
705                 710                 715                 720 cca aag gaa agc caa gag caa gga gaa ggt gaa gag caa gag gaa ggt   2208
Pro Lys Glu Ser Gln Glu Gln Gly Glu Gly Glu Gln Glu Glu Gly
                725                 730                 735 caa gag cag atg aag ttc gag cgt aca gaa gac cat cgc gat att tct   2256
Gln Glu Gln Met Lys Phe Glu Arg Thr Glu Asp His Arg Asp Ile Ser
            740                 745                 750 ggt aaa gat gta aac gga tcc cat cat cac cat cac cat taa           2298
Gly Lys Asp Val Asn Gly Ser His His His His His His
        755                 760                 765

<210> SEQ ID NO 16
<211> LENGTH: 765
<212> TYPE: PRT
<213> ORGANISM: artificial sequence
<220> FEATURE:
<223> OTHER INFORMATION: UBP1deltaC , based on yeast source

<400> SEQUENCE: 16

Gly Gly Asp His Leu Asn Tyr Ile Val Glu Ser Val Ser Glu Met Thr
1               5                   10                  15

Thr Asn Phe Arg Asn Asn Asn Ser Leu Ser Arg Trp Leu Pro Arg Ser
            20                  25                  30

Lys Phe Thr His Leu Asp Glu Glu Ile Leu Lys Arg Gly Gly Phe Ile
        35                  40                  45

Ala Gly Leu Val Asn Asp Gly Asn Thr Cys Phe Met Asn Ser Val Leu
    50                  55                  60

Gln Ser Leu Ala Ser Ser Arg Glu Leu Met Glu Phe Leu Asp Asn Asn
65                  70                  75                  80

Val Ile Arg Thr Tyr Glu Glu Ile Glu Gln Asn Glu His Asn Glu Glu
                85                  90                  95

Gly Asn Gly Gln Glu Ser Ala Gly Asp Glu Ala Thr His Lys Lys Asn
            100                 105                 110

Thr Arg Lys Gly Gly Lys Val Tyr Gly Lys His Lys Lys Leu Asn
        115                 120                 125

Arg Lys Ser Ser Ser Lys Glu Asp Glu Glu Lys Ser Gln Glu Pro Asp
    130                 135                 140

Ile Thr Phe Ser Val Ala Leu Arg Asp Leu Leu Ser Ala Leu Asn Ala
145                 150                 155                 160

Lys Tyr Tyr Arg Asp Lys Pro Tyr Phe Lys Thr Asn Ser Leu Leu Lys
                165                 170                 175

Ala Met Ser Lys Ser Pro Arg Lys Asn Ile Leu Leu Gly Tyr Asp Gln
            180                 185                 190

Glu Asp Ala Gln Glu Phe Phe Gln Asn Ile Leu Ala Glu Leu Glu Ser
        195                 200                 205

Asn Val Lys Ser Leu Asn Thr Glu Lys Leu Asp Thr Thr Pro Val Ala
    210                 215                 220
```

```
Lys Ser Glu Leu Pro Asp Asp Ala Leu Val Gly Gln Leu Asn Leu Gly
225                 230                 235                 240

Glu Val Gly Thr Val Tyr Ile Pro Thr Glu Gln Ile Asp Pro Asn Ser
            245                 250                 255

Ile Leu His Asp Lys Ser Ile Gln Asn Phe Thr Pro Phe Lys Leu Met
        260                 265                 270

Thr Pro Leu Asp Gly Ile Thr Ala Glu Arg Ile Gly Cys Leu Gln Cys
    275                 280                 285

Gly Glu Asn Gly Gly Ile Arg Tyr Ser Val Phe Ser Gly Leu Ser Leu
290                 295                 300

Asn Leu Pro Asn Glu Asn Ile Gly Ser Thr Leu Lys Leu Ser Gln Leu
305                 310                 315                 320

Leu Ser Asp Trp Ser Lys Pro Glu Ile Ile Glu Gly Val Glu Cys Asn
                325                 330                 335

Arg Cys Ala Leu Thr Ala Ala His Ser His Leu Phe Gly Gln Leu Lys
            340                 345                 350

Glu Phe Glu Lys Lys Pro Glu Gly Ser Ile Pro Glu Lys Pro Ile Asn
        355                 360                 365

Ala Val Lys Asp Arg Val His Gln Ile Glu Glu Val Leu Ala Lys Pro
    370                 375                 380

Val Ile Asp Asp Glu Asp Tyr Lys Lys Leu His Thr Ala Asn Met Val
385                 390                 395                 400

Arg Lys Cys Ser Lys Ser Lys Gln Ile Leu Ile Ser Arg Pro Pro Pro
                405                 410                 415

Leu Leu Ser Ile His Ile Asn Arg Ser Val Phe Asp Pro Arg Thr Tyr
            420                 425                 430

Met Ile Arg Lys Asn Asn Ser Lys Val Leu Phe Lys Ser Arg Leu Asn
        435                 440                 445

Leu Ala Pro Trp Cys Cys Asp Ile Asn Glu Ile Asn Leu Asp Ala Arg
    450                 455                 460

Leu Pro Met Ser Lys Lys Glu Lys Ala Ala Gln Gln Asp Ser Ser Glu
465                 470                 475                 480

Asp Glu Asn Ile Gly Gly Glu Tyr Tyr Thr Lys Leu His Glu Arg Phe
                485                 490                 495

Glu Gln Glu Phe Glu Asp Ser Glu Glu Lys Glu Tyr Asp Asp Ala
            500                 505                 510

Glu Gly Asn Tyr Ala Ser His Tyr Asn His Thr Lys Asp Ile Ser Asn
        515                 520                 525

Tyr Asp Pro Leu Asn Gly Glu Val Asp Gly Val Thr Ser Asp Asp Glu
    530                 535                 540

Asp Glu Tyr Ile Glu Glu Thr Asp Ala Leu Gly Asn Thr Ile Lys Lys
545                 550                 555                 560

Arg Ile Ile Glu His Ser Asp Val Glu Asn Glu Asn Val Lys Asp Asn
                565                 570                 575

Glu Glu Leu Gln Glu Ile Asp Asn Val Ser Leu Asp Glu Pro Lys Ile
            580                 585                 590

Asn Val Glu Asp Gln Leu Glu Thr Ser Ser Asp Glu Gly Asp Val Ile
        595                 600                 605

Pro Ala Pro Pro Ile Asn Tyr Ala Arg Ser Phe Ser Thr Val Pro Ala
    610                 615                 620

Thr Pro Leu Thr Tyr Ser Leu Arg Ser Val Ile Val His Tyr Gly Thr
625                 630                 635                 640

His Asn Tyr Gly His Tyr Ile Ala Phe Arg Lys Tyr Arg Gly Cys Trp
                645                 650                 655
```

```
Trp Arg Ile Ser Asp Glu Thr Val Tyr Val Asp Glu Ala Glu Val
            660                 665                 670

Leu Ser Thr Pro Gly Val Phe Met Leu Phe Tyr Glu Tyr Asp Phe Asp
        675                 680                 685

Glu Glu Thr Gly Lys Met Lys Asp Asp Leu Glu Ala Ile Leu Ser Asn
    690                 695                 700

Asn Glu Glu Asp Asp Gly Lys Glu Gln Glu Gln Lys Gly Val Gln Glu
705                 710                 715                 720

Pro Lys Glu Ser Gln Glu Gln Gly Gly Glu Gln Glu Gly
                725                 730                 735

Gln Glu Gln Met Lys Phe Glu Arg Thr Glu Asp His Arg Asp Ile Ser
        740                 745                 750

Gly Lys Asp Val Asn Gly Ser His His His His His
        755                 760                 765
```

<210> SEQ ID NO 17
<211> LENGTH: 29
<212> TYPE: DNA
<213> ORGANISM: artificial sequence
<220> FEATURE:
<223> OTHER INFORMATION: oligonucleotide primer

<400> SEQUENCE: 17
aaaaccgcgg tggtttcatt gctggttta                                    29

<210> SEQ ID NO 18
<211> LENGTH: 22
<212> TYPE: DNA
<213> ORGANISM: artificial sequence
<220> FEATURE:
<223> OTHER INFORMATION: oligonucleotide primer

<400> SEQUENCE: 18
ggaagaattc ttgcgcgtcc tc                                           22

<210> SEQ ID NO 19
<211> LENGTH: 18
<212> TYPE: PRT
<213> ORGANISM: artificial sequence
<220> FEATURE:
<223> OTHER INFORMATION: 18-amino acid peptide KALA

<400> SEQUENCE: 19

Asp Pro Gly Asp Lys Asp Gly Asp Gly Tyr Ile Ser Ala Ala Glu Ala
1               5                   10                  15

Met Ala

<210> SEQ ID NO 20
<211> LENGTH: 35
<212> TYPE: DNA
<213> ORGANISM: artificial sequence
<220> FEATURE:
<223> OTHER INFORMATION: oligonucleotide primer

<400> SEQUENCE: 20
tatggcacat catcaccatc accactctgg ttctg                             35

<210> SEQ ID NO 21
<211> LENGTH: 37
<212> TYPE: DNA
<213> ORGANISM: artificial sequence
<220> FEATURE:
<223> OTHER INFORMATION: oligonucleotide primer

<400> SEQUENCE: 21
aattcagaac cagagtggtg atggtgatga tgtgcca                                   37

<210> SEQ ID NO 22
<211> LENGTH: 29
<212> TYPE: DNA
<213> ORGANISM: artificial sequence
<220> FEATURE:
<223> OTHER INFORMATION: oligonucleotide primer

<400> SEQUENCE: 22
ggggatcctt aaccaccgcg gagacgtaa                                            29

<210> SEQ ID NO 23
<211> LENGTH: 35
<212> TYPE: DNA
<213> ORGANISM: artificial sequence
<220> FEATURE:
<223> OTHER INFORMATION: oligonucleotide primer

<400> SEQUENCE: 23
ggggaattcc aaattttgt taaaacttta actgg                                      35

<210> SEQ ID NO 24
<211> LENGTH: 35
<212> TYPE: DNA
<213> ORGANISM: artificial sequence
<220> FEATURE:
<223> OTHER INFORMATION: oligonucleotide primer

<400> SEQUENCE: 24
gactccgcgg tggtacccat aattatggtc attac                                     35

<210> SEQ ID NO 25
<211> LENGTH: 33
<212> TYPE: DNA
<213> ORGANISM: artificial sequence
<220> FEATURE:
<223> OTHER INFORMATION: oligonucleotide primer

<400> SEQUENCE: 25
ggggatcctt agtttacatc tttaccagaa ata                                       33

<210> SEQ ID NO 26
<211> LENGTH: 817
<212> TYPE: PRT
<213> ORGANISM: artificial sequence
<220> FEATURE:
<223> OTHER INFORMATION: Figure 2b, UBP1 variant, based on yeast source

<400> SEQUENCE: 26

Met Asp Leu Phe Ile Glu Ser Lys Ile Asn Ser Leu Leu Gln Phe Leu
1               5                   10                  15

Phe Gly Ser Arg Gln Asp Phe Leu Arg Asn Phe Lys Thr Trp Ser Asn
            20                  25                  30

Asn Asn Asn Asn Leu Ser Ile Tyr Leu Leu Ile Phe Gly Ile Val Val
        35                  40                  45

Phe Phe Tyr Lys Lys Pro Asp His Leu Asn Tyr Ile Val Glu Ser Val
    50                  55                  60

Ser Glu Met Thr Thr Asn Phe Arg Asn Asn Ser Leu Ser Arg Trp
65                  70                  75                  80

Leu Pro Arg Ser Lys Phe Thr His Leu Asp Glu Glu Ile Leu Lys Arg
                85                  90                  95

```
Gly Gly Phe Ile Ala Gly Leu Val Asn Asp Gly Asn Thr Cys Phe Met
            100                 105                 110

Asn Ser Val Leu Gln Ser Leu Ala Ser Ser Arg Glu Leu Met Glu Phe
        115                 120                 125

Leu Asp Asn Asn Val Ile Arg Thr Tyr Glu Ile Glu Gln Asn Glu
    130                 135                 140

His Asn Glu Glu Gly Asn Gly Gln Glu Ser Ala Gln Asp Glu Ala Thr
145                 150                 155                 160

His Lys Lys Asn Thr Arg Lys Gly Gly Lys Val Tyr Gly Lys His Lys
                165                 170                 175

Lys Lys Leu Asn Arg Lys Ser Ser Lys Glu Asp Glu Lys Ser
            180                 185                 190

Gln Glu Pro Asp Ile Thr Phe Ser Val Ala Leu Arg Asp Leu Leu Ser
        195                 200                 205

Ala Leu Asn Ala Lys Tyr Tyr Arg Asp Lys Pro Tyr Phe Lys Thr Asn
    210                 215                 220

Ser Leu Leu Lys Ala Met Ser Lys Ser Pro Arg Lys Asn Ile Leu Leu
225                 230                 235                 240

Gly Tyr Asp Gln Glu Asp Ala Gln Glu Phe Gln Asn Ile Leu Ala
                245                 250                 255

Glu Leu Glu Ser Asn Val Lys Ser Leu Asn Thr Glu Lys Leu Asp Thr
            260                 265                 270

Thr Pro Val Ala Lys Ser Glu Leu Pro Asp Asp Ala Leu Val Gly Gln
        275                 280                 285

Leu Asn Leu Gly Glu Val Gly Thr Val Tyr Ile Pro Thr Glu Gln Ile
    290                 295                 300

Asp Pro Asn Ser Ile Leu His Asp Lys Ser Ile Gln Asn Phe Thr Pro
305                 310                 315                 320

Phe Lys Leu Met Thr Pro Leu Asp Gly Ile Thr Ala Glu Arg Ile Gly
                325                 330                 335

Cys Leu Gln Cys Gly Glu Asn Gly Gly Ile Arg Tyr Ser Val Phe Ser
            340                 345                 350

Gly Leu Ser Leu Asn Leu Pro Asn Glu Asn Ile Gly Ser Thr Leu Lys
        355                 360                 365

Leu Ser Gln Leu Leu Ser Asp Trp Ser Lys Pro Glu Ile Ile Glu Gly
    370                 375                 380

Val Glu Cys Asn Arg Cys Ala Leu Thr Ala Ala His Ser His Leu Phe
385                 390                 395                 400

Gly Gln Leu Lys Glu Phe Glu Lys Lys Pro Glu Gly Ser Ile Pro Glu
                405                 410                 415

Lys Pro Ile Asn Ala Val Lys Asp Arg Val His Gln Ile Glu Glu Val
            420                 425                 430

Leu Ala Lys Pro Val Ile Asp Asp Glu Asp Tyr Lys Lys Leu His Thr
        435                 440                 445

Ala Asn Met Val Arg Lys Cys Ser Lys Ser Lys Gln Ile Leu Ile Ser
    450                 455                 460

Arg Pro Pro Leu Leu Ser Ile His Ile Asn Arg Ser Val Phe Asp
465                 470                 475                 480

Pro Arg Thr Tyr Met Ile Arg Lys Asn Asn Ser Lys Val Leu Phe Lys
                485                 490                 495

Ser Arg Leu Asn Leu Ala Pro Trp Cys Cys Asp Ile Asn Glu Ile Asn
            500                 505                 510

Leu Asp Ala Arg Leu Pro Met Ser Lys Lys Glu Lys Ala Ala Gln Gln
```

```
                515                 520                 525
Asp Ser Ser Glu Asp Glu Asn Ile Gly Gly Tyr Tyr Thr Lys Leu
        530                 535                 540

His Glu Arg Phe Glu Gln Glu Phe Glu Asp Ser Glu Glu Lys Glu
545                 550                 555                 560

Tyr Asp Asp Ala Glu Gly Asn Tyr Ala Ser His Tyr Asn His Thr Lys
                565                 570                 575

Asp Ile Ser Asn Tyr Asp Pro Leu Asn Gly Glu Val Asp Gly Val Thr
                580                 585                 590

Ser Asp Asp Glu Asp Glu Tyr Ile Glu Glu Thr Asp Ala Leu Gly Asn
                595                 600                 605

Thr Ile Lys Lys Arg Ile Ile Glu His Ser Asp Val Glu Asn Glu Asn
        610                 615                 620

Val Lys Asp Asn Glu Glu Leu Gln Glu Ile Asp Asn Val Ser Leu Asp
625                 630                 635                 640

Glu Pro Lys Ile Asn Val Glu Asp Gln Leu Glu Thr Ser Ser Asp Glu
                645                 650                 655

Glu Asp Val Ile Pro Ala Pro Pro Ile Asn Tyr Ala Arg Ser Phe Ser
                660                 665                 670

Thr Val Pro Ala Thr Pro Leu Thr Tyr Ser Leu Arg Ser Val Ile Val
                675                 680                 685

His Tyr Gly Thr His Asn Tyr Gly His Tyr Ile Ala Phe Arg Lys Tyr
        690                 695                 700

Arg Gly Cys Trp Trp Arg Ile Ser Asp Glu Thr Val Tyr Val Val Asp
705                 710                 715                 720

Glu Ala Glu Val Leu Ser Thr Pro Gly Val Phe Met Leu Phe Tyr Glu
                725                 730                 735

Tyr Asp Phe Asp Glu Glu Thr Gly Lys Met Lys Asp Asp Leu Glu Ala
                740                 745                 750

Ile Leu Ser Asn Asn Glu Glu Asp Asp Glu Lys Glu Gln Glu Gln Lys
        755                 760                 765

Gly Val Gln Glu Pro Lys Glu Ser Gln Glu Gln Gly Glu Gly Glu Glu
    770                 775                 780

Gln Glu Glu Gly Gln Glu Gln Met Lys Phe Glu Arg Thr Glu Asp His
785                 790                 795                 800

Arg Asp Ile Ser Gly Lys Asp Val Asn Gly Ser His His His His His
                805                 810                 815

His
```

UBP1 PROTEASE MUTANT AND ITS CODING SEQUENCE, THEIR APPLICATIONS AND HETEROGONOUS PROTEIN EXPRESSION SYSTEM

This application is a §371 national stage of PCT International Application No. PCT/PL2005/000002, filed Jan. 10, 2005, the contents of which are hereby incorporated by reference into this application.

Ubiquitin is a protein commonly found in eukaryotic organisms. It has been shown that (R. Baker, Current Opinion in Biotechnology 1996, 7:541-546) it is a convenient carrier of heterologous proteins obtained through expression in *Escherichia coli*. Ubiquitin is made of 76 amino-acid residues with a total molecular mass of 8.8 kDa. This protein is an element of the universal protein modification system. Ubiquitination accompanies almost every metabolic process, from cell division and differentiation up to cellular death. Ubiquitin is involved in the regulation of gene expression, DNA repair, and influences chromatin activity. It also takes part in tumour transformation. It plays a fundamental role in the proteolysis of regulatory proteins with short half-lives, as well as of proteins with longer half-lives which for various reasons must be eliminated from the cell.

Protein ubiquitination does not occur in bacteria. It has been proven that proteins bound to ubiquitin are expressed in *E. coli*, and are more stable. Crystallography studies of ubiquitin using magnetic nuclear resonance have shown that it is a compact, globular molecule both in aqueous solution and in solid state (S. Vijay-Kumar, C. Bugg, W. Cook, J. Mol. Biol. 15 1987, 194:531-544). The hydrophobic core of ubiquitin is composed of five parallel lengths of polypeptide chain, bound with regularly spaced hydrogen bonds which form a so-called β-pleated sheet. The edges of its surface are held by lengths of polypeptide chain containing 3.5 twists of an α-helix. Such a structure gives the ubiquitin molecule uncommonly high resistance to temperature, a wide range of pH and environmental polarity changes (M. M. Harding, D. H. Williams, D. N., Woolfson Biochemistry 1991, 30:3 120-3128).

Protease UBP1 is an enzyme isolated from yeast, which cleaves ubiquitin from proteins fused to its C-end. The enzyme was described in 1991 (J. Tobias, A. Varshaysky, J. Biol. Chem. 1991, 266; 12021-12028) and is the subject of the patent application WO91/17245 (European Patent EP 531 404). Its activity and culture conditions were described in *E. coli*. In accordance to the contents of the description, it is a cysteine protease, which binds ubiquitin with an ester bond during the course of the reaction. UBP1 is 809 amino-acids long. The enzyme's activity is dependent on its ability to cleave the ubiquitin peptide from a polypeptide fused to its C-end, regardless of the amino-acid sequence of the N-end of the polypeptide being digested off.

Application No. WO93/09235 describes other yeast proteins belonging to the same family of proteases, namely UBP2 and UBP3. These proteins exhibit similar activity (see also U.S. Pat. No. 5,494,818, U.S. Pat. No. 5,212,058, U.S. Pat. No. 5,683,904).

There are expression systems known, in which fusion proteins are obtained composed of ubiquitin or its derivative and a polypeptide of interest, and then, using a ubiquitin removing enzyme (e.g. UBP1) the protein of interest is recovered (for examples see: U.S. Pat. No. 5,132,213, U.S. Pat. No. 6,018,102). This method has many advantages such as improved quality and efficiency of obtaining the protein, as well as simplification of purification, which is of great importance in the industrial production of recombinant proteins (for example see: WO03/010204). Using an enzyme which removes ubiquitin and appropriate fusion proteins one may also obtain N-terminally modified polypeptides (for example: U.S. Pat. No. 5,847,097).

The international submission published as WO 2004/097011 describes UBP1 protease deletion mutants, containing a deletion of at least a portion of the initial 54 amino-acids from the amino-acid sequence of the UBP1 protease, and also describes some point mutations, which improve the expression level of such a protease in microbiological expression systems.

The application of an enzyme which removes ubiquitin in technological processes requires large amounts of this protein, which should also exhibit the maximal proteolytic activity level. A majority of known methods do not facilitate the efficient expression of this enzyme, which has greatly limited its applicability, especially in industrial processes. The purity and activity of the enzyme are important, if it is to be used in a subsequent stage of the production of a particular protein. Despite the solutions presented in WO 2004/097011, there is still a need to obtain a protein for cleaving UBP1, which could be produced in an efficient manner, for example through the expression in known microbiological systems, which protein would also exhibit improved specific proteolytic activity characteristics.

The goal of the present invention is provide an efficient method for the production of a protein for removing ubiquitin which could be successfully used in the industrial production of recombinant proteins in bacterial cells, in the form of fusion proteins with ubiquitin, as well as a more efficient method of production of proteins with UBP1 activity. Thus, the goal of the present invention is also to produce a nucleotide sequence facilitating the efficient expression of an enzyme with UBP1 activity. The goal of the present invention is also to produce a new, improved polypeptide producing a protein with UBP1 activity. The next goal of the present invention is to produce a new enzyme which cleaves ubiquitin, which would exhibit specific proteolytic activity of an improved character.

The topic of the present invention is a mutant of the UBP1 protease characterised in that it contains an amino-acid sequence containing the following modifications:

a substitution at position 754 of the amino-acid sequence of UBP1, deletions of amino-acids found at positions 1 to 54 of the UBP1 sequence and at least a portion of the amino-acids found at positions 55 to 98 of the UBP1 sequence.

It was unexpectedly found that glutamine found at position 754 has a significant effect on the UBP1 protein expression, particularly in microbiological expression systems. The introduction of a substitution at position 754 of the amino-acid sequence of UBP1 resulted in the improvement in the expression of the mutant obtained, without an undesirable reduction in its activity level. This effect is presented in the examples below. The mentioned substitution at position 754 may be the result of replacing glutamine at this position with any other amino-acid. In a particular case, this will be a natural amino-acid, and the introduction of the change will consist of introducing an appropriate codon change in the sequence used to express the mutant produced. In a particularly preferential embodiment, the characteristics of the introduced amino-acid are significantly different than those of glutamine. Thus, basic, neutral or hydrophobic amino-acids will be preferred. In a particular embodiment of the present invention, the amino-acid replacing glutamine at position 754 of the amino-acid sequence of UBP1 may be an amino-acid containing a neutral amino-acid residue, for example selected from among Ala, Val, Ile, Leu, or Gly. A mutant was described in an example embodiment, in which the glutamine at position 754 of the UBP1 sequence was replaced with leucine.

Also unexpectedly, it was found that preferential properties of UBP1 deletion mutants can be obtained through the simultaneous contraction of the sequence at the N-end of UBP1. Extensive mutations, in an extreme case encompassing all of the 98 amino-acids found at the N-end of UBP1, yield a protein which is produced faster and more efficiently, while still maintaining the desirable ubiquitin-cleaving enzymatic activity.

Therefore, according to the preferential embodiment of the present invention, the deletion encompasses all amino-acid found at positions 1 to 98 of the UBP1 sequence.

The mutants obtained can also contain additional mutations, published in WO2004/097011, which improve the properties of the mutants obtained. Preferentially, a mutant according to the present invention contains an amino-acid sequence containing at least one of the following modifications:
  replacement of the proline at position 415 of the UBP1 sequence with leucine,
  replacement of the phenylalanine at position 739 of the UBP1 sequence with leucine,
  fusion of the ubiquitin polypeptide to the N-terminal amino-acid with a peptide bond,
  fusion of a marker sequence to the C-terminal amino-acid of the amino-acid sequence,
  attachment with a peptide bond of a fusion polypeptide to the N-terminal aminoacid, where the fusion polypeptide is composed of a peptide containing the marker aminoacid sequence and the ubiquitin fused to its C-end, and preferentially the fusion polypeptide is 6HisUbi whose sequence is represented as SEQ ID NO: 2.

The mentioned amino-acid marker sequence is a sequence which facilitates the isolation of polypeptides containing it, particularly using affinity chromatography. A person skilled in the art would be able to design a series of such sequences based on common knowledge, which could be used to design an isolation system for the protein produced using affinity chromatography. For example, the introduction of a sequence recognized by an antibody facilitates the isolation of the protein using this antibody. Other examples are amino-acid sequences with affinity for particular nucleotide sequences. Yet another example are techniques basing on the well known phenomenon of complex formation between certain amino-acid residues and transition metal atoms. The best known example of such a system are complexes of Zinc and His. All such systems composed of an amino-acid marker sequence and of a substance for which the sequence has a sufficiently strong affinity can be used to design an isolation system for proteins containing the marker sequence. Usually, this will be affinity chromatography in a medium containing the mentioned substance. Due to the above, in one of the preferential embodiments of the present invention, the marker amino-acid sequence contains a sequence of six histidines (His6).

Preferentially, a mutant according to the present invention is selected from among UBI::UBP1ΔC (SEQ ID NO:4), UBP1ΔC2 (SEQ ID NO:6).

Another subject of the present invention is a nucleotide sequence coding the UBP1 protease mutant defined above, characterised in that it contains the following mutations:
  replacement of the glutamine codon at position 754 of the amino-acid sequence of UBP1 for a different amino-acid codon,
  deletion of the initial 54 codons of the sequence coding UBP1 and at least a portion of the codons found at positions to 98 in the sequence coding UBP1. Preferentially, the deletion encompasses the initial 294 nucleotides of the sequence coding UBP1.

Equally preferentially, a nucleotide sequence according to the present invention additionally contains at least one of the following mutations:
  replacement of the proline codon at position 415 of the amino-acid sequence of UBP1 with a leucine codon,
  replacement of the phenylalanine codon at position 739 of the amino-acid sequence of UBP1 with a leucine codon,
  fusion of a ubiquitin-coding sequence, preferentially in the beginning region of the reading frame,
  fusion of a sequence coding a marker amino-acid sequence, preferentially in the end region of the reading frame,
  attachment of a sequence coding a fusion polypeptide to the beginning region of the reading frame, where the sequence coding the fusion polypeptide is composed of a sequence coding the marker amino-acid sequence and a sequence coding ubiquitin, where the sequence coding the fusion polypeptide preferentially is the sequence coding 6HisUbi represented as SEQ ID NO: 2, where the marker amino-acid sequence is a sequence facilitating the isolation of the polypeptide containing it, particularly using affinity chromatography. In one example embodiment of the present invention, the sequence coding the marker amino-acid sequence contains a sequence composed of six consecutive histidine codons.

To improve the expression level in the selected expression system, a nucleotide sequence according to the present invention additionally contains codon changes which account for the preferences of the planned expression system. Preferentially, the planned expression host is *E. coli*, and codon changes encompass a change selected from the following:
  replacement of at least one arginine codons at positions 96, 334, 425, 476, 482, 487, 613, 702, 705, 710, 796, 801 of the amino-acid sequence of UBP1 with either a CGT or CGC codon,
  replacement of at least one leucine codons at positions 354, 356, 258, 367, 369, 372, 373, 479, 480 of the amino-acid sequence of UBP1 with the CTG codon.

In a preferential embodiment of the present invention, the nucleotide sequence contains one of the nucleotide sequences represented as the sequence coding UBP1ΔC (SEQ ID NO:4), or the sequence coding UBP1ΔC2 (SEQ ID NO:6).

The next subject of the present invention is the application of the UBP1 protease mutant according to the present invention defined above to obtain ubiquitin-cleaving enzymatic activity.

In a particular embodiment of this aspect of the present invention, the ubiquitin-cleaving enzyme obtained is used to obtain a protein of interest from a hybrid protein composed of a peptide containing ubiquitin and the protein of interest.

Preferentially, the UBP1 protease mutant and the peptide containing ubiquitin contain an amino-acid marker sequence which facilitates their isolation from a reaction mixture, wherein the protein of interest is a medicinal protein, such as interleukin, interferon, growth hormone, insulin or erythropoietin.

The next subject of the present invention is a heterologous protein expression system in bacterial cells, characterised in that it contains:
  an expression cassette coding a hybrid protein composed of a peptide containing ubiquitin and the heterologous protein sequence, and
  a UBP1 protease mutant, according to the present invention, as defined above.

Preferentially, the UBP1 protease and peptide containing ubiquitin contain a marker amino-acid sequence, and the nucleotide sequence of the expression box contains codon changes taking into account the preferences of the planned expression system.

The next subject of the present invention is an application of the nucleotide sequence according to the present invention, as defined above, to obtain an enzyme cleaving ubiquitin.

The next subject of the present invention is an expression vector, characterised in that it contains a nucleotide sequence coding a UBP1 protease mutant according to the present invention, as defined above. In one of the example embodiments of this aspect of the present invention, the nucleotide sequence coding the UBP1 protease mutant is contained on plasmid pT7-7ArgStop.

The next subject of the present invention is a host cell transformed with an expression vector defined above.

The next subject of the present invention is a method of obtaining a protein cleaving ubiquitin, characterised, in that a host cell is cultured which has been transformed with an expression vector containing with an expression vector containing a nucleotide sequence coding the UBP1 protease mutant according to the present invention defined above, and subsequently the enzyme or the fraction containing it is isolated. In a particular embodiment of the method according to the present invention, the amino-acid sequence of the UBP1 protease mutant contains a sequence of six consecutive histidines (His6), and the proteases mutant produced is isolated using the well known affinity chromatography technique.

The next subject of the present invention is a method of obtaining a heterologous protein, characterised in that a host cell is cultured, transformed with an expression vector containing an expression cassette coding a hybrid protein composed of a peptide containing ubiquitin and a heterologous protein sequence under conditions favourable to the production of the hybrid protein. The hybrid protein or a fraction containing it is isolated, and then the hybrid protein thus obtained is digested with the UBP1 protease mutant according to the present invention, as defined above. Next, the UBP1 protease mutant is removed from the reaction mixture along with the peptide containing ubiquitin and the heterologous protein is isolated. In a particular embodiment of the method according to the present invention, the UBP1 protease mutant and the peptide containing ubiquitin contain a sequence of six consecutive histidines (His6) and are removed from the mixture using the well known affinity chromatography technique.

Unexpectedly, it turned out that the new UBP1 mutants proposed in the present invention retain the fundamental activity of cleaving ubiquitin, and are easier to obtain. The means and methods presented facilitate the easy and efficient expression of an enzyme with UBP1 activity, for example in the well understood system based on E. coli cells. Due to this the mutant according to the present invention is suitable for industrial use, for example in the synthesis of recombinant proteins encompassing the expression of hybrid proteins containing ubiquitin.

A heterologous protein contained in a hybrid protein according to the present invention mentioned above may be an arbitrary known protein, whose coding sequence is known. For example, this may be a medicinal protein, whose production is desirable due to its therapeutic proteins. Based on the instructions contained in the present description common knowledge, a professional will be able to design a sequence coding a hybrid protein containing a sequence coding the desired heterologous protein. Sequences of known heterologous proteins may for example be obtained from the GenBank database, available at the URL www.ncbi.nlm.nih.gov/Genbank/index.html, which contains the sequences of known genes. To increase the expression level of the heterologous protein in a bacterial system, one may use methods which include the use of strong promoters, transcription enhancer sequences or codons preferred by the bacterial cell.

To better illustrate the nature of the present invention, the description includes the following figures:

FIG. 1 (SEQ ID No: 3, SEQ ID No: 4) represents the UB1::UBP1ΔC gene and its various variants and derivatives. The deleted DNA fragment is in bold, whereas primer sequences, the C mutation and histidine residues are in underlined italics.

FIG. 2A (SEQ ID No. 5) represents the nucleotide sequence of UBP1ΔC2 protease (SEQ ID No. 5). FIG. 2B (SEQ ID No: 26) represents the amino-acid sequence of UBP1ΔC2 protease (SEQ ID No: 6) prior to deletion of the 98 N-terminal amino-acids found in the wild-type UBP1. Bold italics delineate mutation C at position 754 and fused histidine residues, the active centre is in italics. The sequence in bold is removed from the N-end.

FIG. 3 represents an image of an SDS-PAGE electrophoresis gel. The lanes contain, in turn: 1—lysate of E. coli BLD3 bacteria transformed with pT7-7ArgStopUBI::UBP1ΔC2, not induced with IPTG (from cultures maintained in 100 ml LB), 2—lysate of E. coli BLD3 bacteria transformed with pT7-7ArgStopUBI::UBP1ΔC2, induced with IPTG (from cultures maintained in 100 ml LB), 3—lysate of E. coli BLD3 bacteria transformed with pT7-7ArgStopUBI::UBP1ΔC2, not induced with IPTG (from cultures maintained in a fermentor containing 3,5 l LB), 4—lysate of E. coli BLD3 bacteria transformed with pT7-7ArgStopUBI::UBP1ΔC2, induced with IPTG (from cultures maintained in a fermentor containing 3,5 l LB), 5—sonicated supernatant (20 μl of samples from cultures maintained in a fermentor), 6—lysate of E. coli BLD3 bacteria transformed with pT7-7ArgStopUBI::UBP1ΔC, not induced with IPTG, 7—lysate of E. coli BLD3 bacteria transformed with pT7-7ArgStopUBI::UBP1ΔC, induced with IPTG, 8—lysate of E. coli BLD3 bacteria transformed with pT7-7ArgStop+ubiquitin, not induced with IPTG, 9—lysate of E. coli BLD3 bacteria transformed with pT7-7ArgStop+ubiquitin, induced with IPTG, 10—molecular mass marker (kDa).

FIG. 4 represents an image of an SDS-PAGE electrophoresis gel. The lanes contain in turn: 1—molecular mass marker (kDa), 2—the substrate, UB1::KALA digested with ubi::UBP1ΔC2 (SEQ ID No. 10), 3—the substrate, UB1::KALA.

FIG. 5 represents an image of an SDS-PAGE electrophoresis gel. The lanes contain in turn: 1—the substrate UB1::ElisaC digested with ubi::UBP1ΔC (SEQ ID No. 4), 2—the substrate UB1::ElisaC digested with ubi::UBP1ΔC2 (SEQ ID No. 10), 3—the undigested substrate UBI::ElisaC, 4—molecular mass marker (kDa), 5—the substrate UB1::KALA digested with ubi::UBP1ΔC2 (SEQ ID No. 10), 6—the substrate UB1::KALA digested with ubi::UBP1ΔC, 7—the undigested substrate UB1::KALA.

FIG. 6 represents the 6HisUbi nucleotide sequence (SEQ ID No. 1) and amino acid sequence (SEQ ID No. 2).

FIG. 8 represents the sequence of 6HisUBI::ElisaC (SEQ ID No. 7, SEQ ID No. 8).

Figure 9:
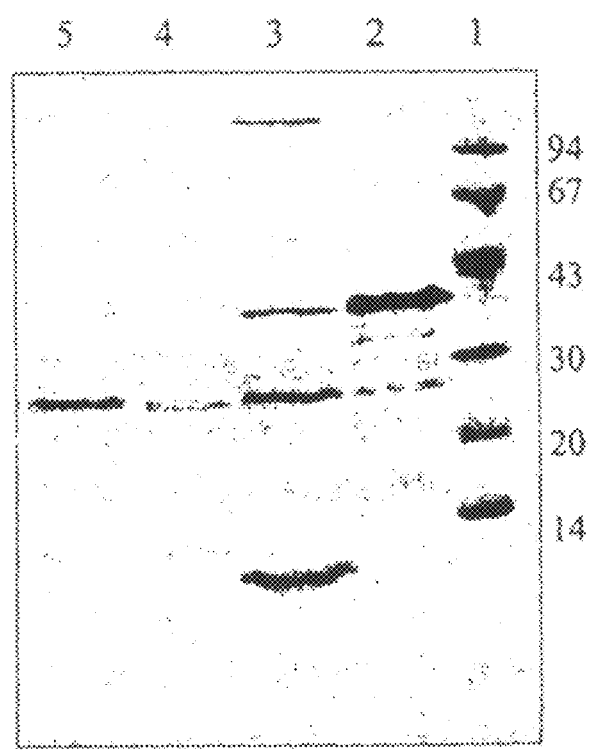

FIG. 9 represents example results of the application the system according to the present invention to express the ElisaC protein (see example 3). An image of an SDS-PAGE gel is presented in which the lanes contain, in turn: 1—molecular mass marker (kDa), 2—6HisUbi::ElisaC (SEQ ID No. 8) purified in a chromatography column containing Ni- NTA medium, 3—6HisUbi::ElisaC (SEQ ID No. 8) digested with protease UBP1ΔC2 (SEQ ID No. 6), 4 and 5—ElisaC protein purified in a chromatography column filled with Ni-NTA medium, with 6HisUbi removed.

The following examples are only meant to present assorted embodiments of the present invention and should not be viewed as the whole of its scope.

EXAMPLE 1

New UBP1 Protease Mutants and their Coding Sequences

It has been determined that the active centre of the enzyme UBP1 probably begins from the amino-acid 102. The removal of amino-acids was planned. The following primers were designed to this end:

```
SKRUT 1
5' AAAACCGCGGTGGTTTCATTGCTGGTTTA 3'
(SEQ ID No. 17)
        Sac II

SKRUT 2
5' GGAAGAATTCTTGCGCGTCCTC 3'
(SEQ ID No. 18)
      Eco RI
```

The location of the primers is shown in bold in FIG. 1.

Primers: SKRUT1 (SEQ ID No. 17) and SKRUT2 (SEQ ID No. 18) were used to amplify a 468 bp fragment using PCR, on a template of pT7-7ArgStopUBI::UBP1ΔC6His. Next, the 468 bp fragment was cloned into the pBluscript (−) vector, between Eco RI and Sac II restriction sites. The UBP1ΔC protease fragment was sequenced and cloned into the pT7-7ArgStopUBI::UBP1ΔC6His plasmid digested with Eco RI and Sac II restrictases. Using this method, a sequence was formed coding the UBP1ΔC2 protease (SEQ ID No. 5) truncated by 294 bp, which corresponds to the UBP1ΔC2 protein (SEQ ID No. 6) truncated by 98 amino-acid. The sequence represents the gene of protease UB1::UBP1ΔC2 (see SEQ ID No. 9 and 10), which contains mutation C, meaning the replacement of a glutamine codon (CAG) with a leucine codon (CTG) at position 754 (see WO2004/097011). The hybrid protein UB1::UBP1ΔC2 (SEQ ID No. 10) is 796 amino-acids long, with a mass of 88.35 kDa. Changes introduced into the amino-acid sequence are also represented in FIG. 2.

The UBP1ΔC protease gene (e.g. SEQ ID No. 15) was additionally modified through the replacement of a portion of arginine codons, unfavourable to *E. coli* (AGA or AGG), for codons favourable to *E. coli* (CGT or CGC). The UBP1ΔC2 protease gene (SEQ ID No. 5) in its final form (vs. UBP1ΔC protease (SEQ ID No. 16)) has had the following arginine codons at positions 334, 425 and 613 replaced. The leucine codon, TTA, was also replaced with CTG at positions 354, 356, 358, 367, 369, 372, 373, 479 and 480. The changes introduced are delineated in FIG. 1 in bold.

EXAMPLE 2

Obtaining New UBP1 Mutants

Figure 3:
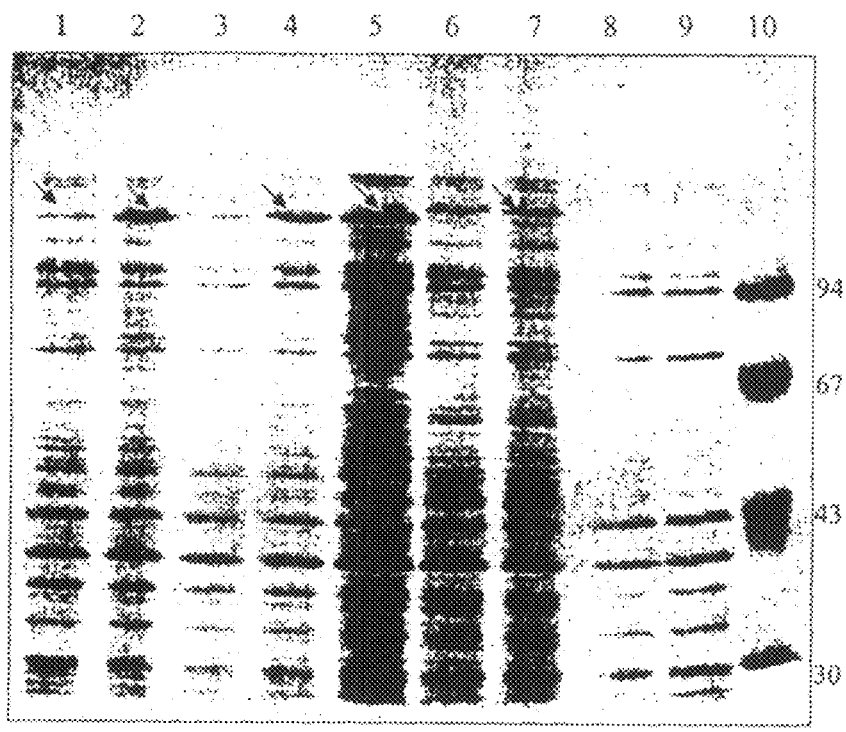

Expression of the UBI::UBP1ΔC2 protease (SEQ ID No. 10) with six histidine residues attached at its C-end was achieved in competent *E. coli* BLD3 and *E. coli* T7ples cells. The results are shown in FIG. 3, in which its expression results are shown along with the expression results of the gene UB1::UBP1ΔC (patent WO2004097011 and SEQ ID No: 3). The culture was maintained until OD=1 (ca. 9h) at 25° C. in LB medium with amphicilin. Following centrifugation, the bacteria were sonicated. The supernatant was cleaned using ion affinity chromatography. The activity of the UBI::UBP1ΔC2 protease (SEQ ID No. 10) was assayed using a standard method using the hybrid protein substrate UBT::KALA (where KALA is an 18-amino-acid peptide with the amino-acid sequence AspProGlyAspLysAspGlyAspGly-TyrIleSerAlaAlaGluAlaMetAla) (SEQ ID No. 19) as well as the substrate His6UBI::ElisaC (SEQ ID No: 8).

The reactions were performed at a volume of 50 μl at 37° C., for min. in a buffer with the following composition: 20 mM phosphate pH 7.5, 2 mM DDT, 1 mM EDTA. 40 μl of the substrate UB1::KALA were digested with a protein concentration of 0.1 mg/ml and 20 μl of substrate His6UBI::ElisaC (SEQ ID No. 8) with a protein concentration of 1 mg/ml, and 3 μl of proteases UBP1ΔC (SEQ ID No. 16) and UBP1ΔC2 (SEQ ID No. 6) with concentrations of 0.5 mg/ml (1.5 μg of enzyme).

Figure 4:
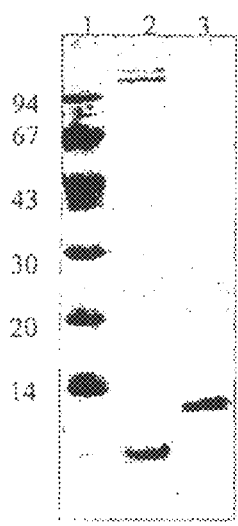
Figure 5:
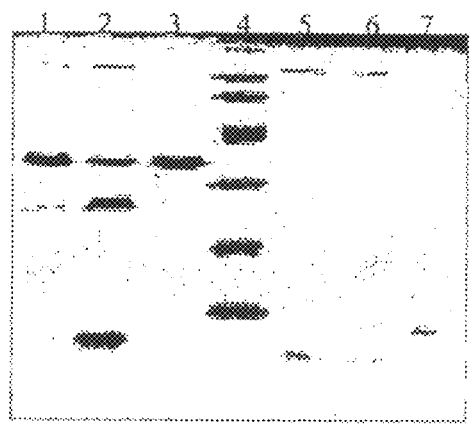

The digestion reactions were stopped by heating to 100° C., and the samples were put on SDS-PAGE gels. SDS-Polyacrylamide gel image analysis showed that the enzyme UBP1ΔC2 (SEQ ID No. 6) is 5-6 times more active than mutant UBP1ΔC (SEQ ID No. 16). The results are shown in FIGS. 4 and 5.

It should be shown that for following truncation, the UBP1 protease gene with mutation C, the time of bacterial cell growth to OD=1 was also shortened in *E. coli* BLD21 (table No. 1).

TABLE NO. 1

| | Protease-mutants | | |
|---|---|---|---|
| | UBP1Δ<br>SEQ ID No: 14 | UBP1ΔC<br>SEQ ID No: 16 | UBP1ΔC2<br>SEQ ID No: 6 |
| Time to OD = 1 (h) | 48 | 12 | 9 |

The level of expression of this gene grew significantly in comparison to the UBP1ΔC protease gene, whereas the UBP1Δ protease gene (SEQ ID No. 13) is expressed at trace levels, (undetectable in SDS-PAGE gel images). Thus the application of unmodified UBP1 protease in laboratory practice and the production of recombinant medicinal proteins is essentially impossible.

EXAMPLE 3

Heterologous Protein Expression System and its Application

UBP1 mutants described in the present invention were used to design an expression system used to efficiently produce heterologous proteins in bacterial cells. According to the present invention, application of the system is based on the production of heterologous proteins in bacterial cells transformed with DNA containing an expression cassette coding a hybrid protein composed of a peptide containing ubiquitin and a heterologous protein sequence. It may be expected that this form of hybrid protein will be produced more efficiently than a heterologous protein. Furthermore, ubiquitin or its derivative contained in the hybrid protein performs the role of a carrier protein, which additionally increases the stability and facilitates the purification of the protein produced. The purification is particularly simplified when the composition of the expressed hybrid protein contains a ubiquitin derivative containing an amino-acid marker sequence. A heterologous protein is freed from the hybrid protein using a UBP1 protease mutant according to the present invention, which is a part of the expression system.

Because earlier examples showed sample variants of UBP1 mutants which may be incorporated into the proposed expression system, the sections below concentrate on describing examples of the remaining means for the production and application of the proposed system according to the present invention.

To perfect the system described in WO03/010204, based on the fusion of the proteins UBI::protein, the gene coding the UB1::protein hybrid protein was modified through the addition of a marker sequence to the ubiquitin sequence, which marker sequence is easy to isolate using affinity chromatography. In the example described, the hybrid protein produced is in the form His6UBI::protein, in which 6 histidine residues have been added to the N-end of ubiquitin. Following digestion with the UBP1ΔC2 protease (SEQ ID No. 6), such a hybrid protein is easily purified using affinity chromatography with a chelating column, such as NI-NTA. If the removal of the modified ubiquitin containing the marker sequence is performed using a UBP1 protease mutant according to the present invention, which contains the same marker sequence, it is possible to separate both the protease as well as the carrier protein (modified ubiquitin) in the same chromatography column. This greatly simplifies the purification of the heterologous protein produced, and limiting the number of purification stages greatly enhances the efficiency of the whole process. In accordance to the present invention, analogous systems containing marker sequences may be proposed, which can be separated from the reaction mixture using affinity chromatography.

In order to obtain a sequence coding the hybrid protein His6UBI::ElisaC (SEQ ID No. 8) the following synthetic nucleotides were designed:

```
6HisG
      Nde I                            EcoRI
5' TATGGCACATCATCACCATCACCACTCTGGTTCTG 3'
(SEQ ID No. 20)

6HisD
      EcoRI                            Nde I
5' AATTCAGAACCAGAGTGGTGATGGTGATGATGTGCCA 3'
(SEQ ID No. 21)
```

The synthetic fragments were kinased and ligated with the pT7-7ArgStop plasmid digested with the EcoRI and NdeI restrictases. The vector pT7-7ArgStop is a derivative of plasmid pT7-7 (Tabor, S. and Richardson, C. C. (1985) Proc. Nat. Sci. USA, 262, 1074-1078).

The ligation mixture was used to transform competent DH5α cells. Plasmid DNA was isolated using the alkaline method. The vector pT7-7RSH was obtained in this fashion.

To amplify the ubiquitin-coding sequence using PCR, the following primers were designed:

```
HisUbiK
      BamHI
5' GGGGATCCTTAACCACCGCGGAGACGTAA 3'
(SEQ ID No. 22)

HisUbiP
      EcoRI
5' GGGGAATTCCAAATTTTTGTTAAAACTTTAACTGG 3'
(SEQ ID No. 23)
```

The plasmid pUC19UBI was used as a template, which contained a cloned sequence coding ubiquitin composed of synthetic oligonucleotide fragments. The PCR product was isolated in a standard fashion in a polyacrylamide gel and digested with the EcoRI and BamHI restrictases, whose recognition sequences were planned in the primers (in bold). The insert prepared was ligated with the pT7-7RSH vector digested with the same enzymes. The ligation mixture was used to transform competent DH5α cells. Plasmid DNA was isolated using the alkaline method, and following restriction analysis it was sequenced. Plasmid pT7-7RSHU was obtained, which contains the ubiquitin gene which contains an N-terminal DNA fragment coding 6 histidine residues, shown in FIG. 6. This is an example sequence coding a peptide containing ubiquitin also encompassing the marker sequence, which may be used to obtain sequences coding hybrid proteins according to the present invention.

The Construction of the Example Hybrid Protein His6UBI::ElisaC

The DNA fragment coding the C-terminal end of the UBP1ΔC protease (SEQ ID No. 4) 360 bp long was amplified. PCR with ubi::UBP1ΔC (SEQ ID No. 3) as a template was performed using the following primers:

```
ELISA P
      SacII
5' GACTCCGCGGTGGTACCCATAATTATGGTCATTAC
(SEQ ID No. 24)

ELISA K
      BamHI
5' GGGGATCCTTAGTTTACATCTTTACCAGAAATA
(SEQ ID No. 25)
```

Figure 7:
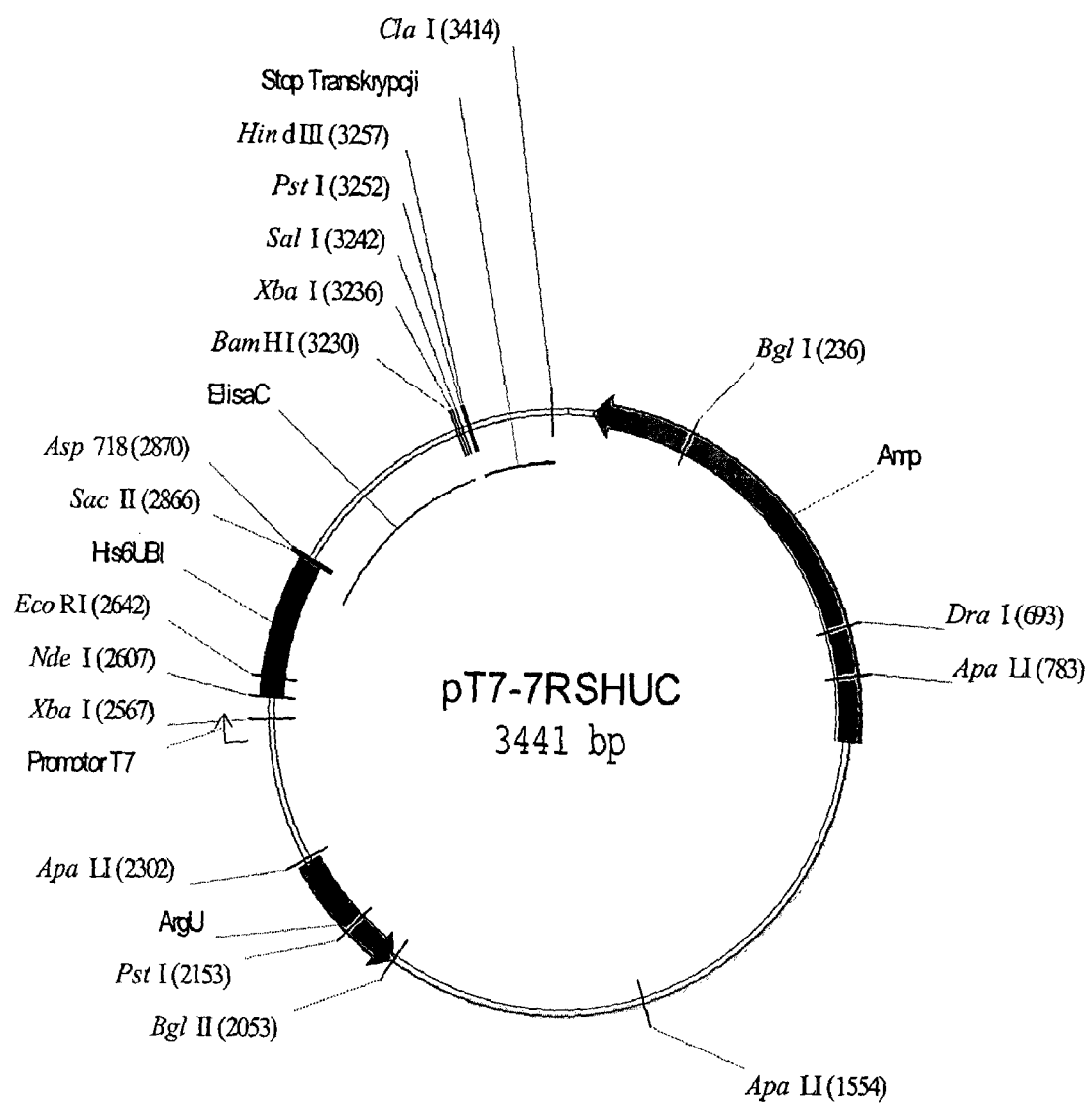
FIG. 7 represents a map of the expression vector pT7-7RHUC.

The 360 bp. (ElisaC) fragment was digested with restriction enzymes SacII and BamHI and ligated with the expression plasmid pT7-7RSH digested with the same enzymes. The ligation mixture was used to transform competent DH5α cells. Plasmid DNA was isolated using the alkaline method and sequenced following restriction analysis. The plasmid pT7-7RSHUC was obtained (FIG. 7). The plasmid DNA was used to transform competent E. coli BLD21 cells. The culture was maintained until $OD_{(\lambda 600)}=1$ in LB medium with ampicillin and a very high expression of 6Hisubi::ElisaC was achieved. The bacteria were sonicated following centrifugation. The supernatant was purified using affinity chromatography on a column of Ni-NTA medium (Qiagen). High purity of the isolated 6HisUBI::ElisaC protein (SEQ ID No. 8) was achieved (the sequence is shown in FIG. 8). The sample was dialised for 16 h against 50 mM phosphate buffer. The hybrid protein was digested with the UBP1ΔC2 protease, which contains 6 histidine residues at its C-end.

The digestion was performed in a volume of 5 ml at 35° C. for 1 h. The reaction was performed in 20 mM phosphate buffer pH 7.5, 2 mM DDT, 1 mM EDTA.

The sample of protein produced was then again applied to a Ni-NTA column and chromatography was performed. High purity ElisaC protein was obtained, cleaved from 6HisUBI. The results are shown in FIG. 9.

The presented hybrid protein expression system facilitates the production of large quantities of hybrid proteins. Using this system of expression-digestion-purification, one may obtain protein of very high purity due to the application of UBP 1 AC2 protease, which contains histidine residues, and due to the fusion of these residues to ubiquitin. Both proteins are retained in a chromatography column containing Ni-NTA medium. The protein digested away from 6His-ubiquitin on the other hand, does not bind to Ni-NTA.

The invention claimed is:

1. A ubiquitin specific protease 1 (UBP1) mutant comprising the following modifications relative to a *Saccharomyces cerevisiae* UBP1 protein:
   - a substitution of the glutamine residue corresponding to position 754 of the amino-acid sequence of *Saccharomyces cerevisiae* UBP1, and
   - a deletion of the amino-acids at positions corresponding to positions 1 to 98 of the amino-acid sequence of *Saccharomyces cerevisiae* UBP1,
   - wherein position numbers of the amino acid sequence of *Saccharomyces cerevisiae* UBP1 are the same as positions of the amino-acid sequence set forth in SEQ ID NO: 26.

2. The mutant according to claim 1, wherein the mutant additionally comprises at least one of the following modifications:
   - a replacement of the proline at a position corresponding to position 415 of the amino-acid sequence of *Saccharomyces cerevisiae* UBP1 with leucine,
   - a replacement of the phenylalanine at a position corresponding to position 739 of the amino-acid sequence of *Saccharomyces cerevisiae* UBP1 with leucine,
   - fusion of a ubiquitin polypeptide to the N-terminal amino-acid of the mutant with a peptide bond,
   - fusion of a marker polypeptide to the C-terminal amino-acid of the mutant with a peptide bond, and/or
   - fusion of a fusion polypeptide to the N-terminal amino-acid of the mutant with a peptide bond, wherein the fusion polypeptide comprises a marker polypeptide and a ubiquitin polypeptide fused to the C-terminal amino acid of the marker polypeptide.

3. The mutant according to claim 2, wherein the marker polypeptide comprises six consecutive histidines ($His_6$).

4. The mutant according to claim 2, wherein the mutant is UBP1ΔC2 (SEQ ID NO:6).

5. The mutant according to claim 2, wherein the fusion polypeptide is 6HisUbi of SEQ ID NO:2.

6. The mutant according to claim 2, wherein the mutant comprises the following modifications:
   a replacement of the proline at a position corresponding to position 415 of the amino-acid sequence of *Saccharomyces cerevisiae* UBP1 with leucine,
   a replacement of the phenylalanine at a position corresponding to position 739 of the amino-acid sequence of *Saccharomyces cerevisiae* UBP1 with leucine,
   fusion of a ubiquitin polypeptide to the N-terminal amino-acid of the mutant with a peptide bond, and
   fusion of a marker polypeptide to the C-terminal amino-acid of the mutant with a peptide bond.

7. A nucleic acid molecule coding a UBP1 mutant comprising the following modifications relative to a nucleic acid molecule coding a *Saccharomyces cerevisiae* UBP1:
   a substitution of the glutamine codon at a position corresponding to position 754 of the amino-acid sequence of *Saccharomyces cerevisiae* UBP1 for another amino-acid codon,
   a deletion of the codons at positions corresponding to positions 1 to 98 of the amino acid sequence of *Saccharomyces cerevisiae* UBP1,
   wherein position numbers of the amino acid sequence of *Saccharomyces cerevisiae* UBP1 are the same as positions of the amino-acid sequence set forth in SEQ ID NO: 26.

8. The nucleic acid molecule according to claim 7, wherein the nucleic acid molecule also comprises at least one of the following modifications:
   a replacement of the proline codon at a position corresponding to position 415 of the amino-acid sequence of *Saccharomyces cerevisiae* UBP1 with a leucine codon,
   a replacement of the phenylalanine codon at a position corresponding to position 739 of the amino-acid sequence of *Saccharomyces cerevisiae* UBP1 with a leucine codon,
   fusion of a polynucleotide coding ubiquitin,
   fusion of a polynucleotide coding a marker polypeptide, and/or
   fusion of a polynucleotide coding a fusion polypeptide, wherein the fusion polypeptide comprises a marker polypeptide and a ubiquitin polypeptide.

9. The nucleic acid molecule according to claim 8, wherein the polynucleotide coding the marker polypeptide comprises six consecutive histidine codons.

10. The nucleic acid molecule according to claim 7, wherein it further comprises codon changes which account for the preferences of a planned expression system.

11. The nucleic acid molecule according to claim 10, wherein the planned expression system is an *E. coli* expression system, and the codon changes comprise:
    a replacement of at least one of the arginine codons at positions corresponding to positions 96, 334, 425, 476, 482, 487, 613, 702, 705, 710, 796, 801 of the amino-acid sequence of *Saccharomyces cerevisiae* UBP1 with either codon CGT or CGC, and/or
    a replacement of at least one of the leucine codons at positions corresponding to positions 354, 356, 258, 367, 369, 372, 373, 469, 470 of the amino-acid sequence of *Saccharomyces cerevisiae* UBP1 with codon CTG.

12. The nucleic acid molecule according to claim 7, wherein the nucleic acid molecule comprises a nucleic acid molecule coding UBP1ΔC2 (SEQ ID NO:6).

13. The nucleic acid molecule according to claim 8, wherein the polynucleotide coding ubiquitin is at the 5' end of the reading frame.

14. The nucleic acid molecule according to claim 8, wherein the polynucleotide coding a marker polypeptide is at the 3' end of the reading frame.

15. The nucleic acid molecule according to claim 8, wherein the fusion polypeptide is 6HisUbi of SEQ ID NO:2.

16. A method of enzymatically cleaving a ubiquitin polypeptide comprising contacting the ubiquitin polypeptide with the UBP1 mutant according to claim 1.

17. A method for obtaining a protein of interest from a hybrid protein comprising contacting the hybrid protein with the UBP1 mutant according to claim 1, wherein the hybrid protein comprises a ubiquitin polypeptide and the protein of interest.

18. The method of claim 17, wherein the protein of interest is selected from the group consisting of interleukin, interferon, growth hormone, insulin, or erythropoietin.

19. A kit comprising:
    an expression cassette coding a hybrid protein, wherein the hybrid protein comprises a ubiquitin polypeptide and a heterologous protein, and
    the UBP1 mutant according to claim 1.

20. An expression vector comprising the nucleic acid molecule according to claim 7.

21. A host cell transformed with the expression vector according to claim 20.

22. A method for obtaining a UBP1 mutant, comprising:
    a. culturing a host cell,
    b. transforming the host cell with an expression vector, wherein the expression vector comprises the nucleic acid molecule according to claim 7, and
    c. isolating the UBP1 mutant or a fraction containing it.

23. The method according to claim 22, wherein the UBP1 mutant comprises six consecutive histindines ($His_6$), and wherein the UBP1 mutant is isolated using affinity chromatography.

24. A method of obtaining a heterologous protein, comprising:
    a. transforming a host cell with an expression vector comprising an expression cassette coding a hybrid protein, wherein the hybrid protein comprises a ubiquitin polypeptide and a heterologous protein,
    b. culturing the transformed host cell under conditions facilitating production of the hybrid protein,
    c. isolating the hybrid protein or a fraction containing it,
    d. digesting said hybrid protein with the UBP1 mutant according to claim 1, and
    e. removing the UBP1 mutant and ubiquitin polypeptide from the reaction mixture,
    thereby obtaining the heterologous protein.

* * * * *